US012385068B2

(12) United States Patent
Bublot et al.

(10) Patent No.: US 12,385,068 B2
(45) Date of Patent: Aug. 12, 2025

(54) RECOMBINANT HVT VECTORS EXPRESSING MULTIPLE ANTIGENS OF AVIAN PATHOGENS AND USES THEREOF

(71) Applicant: BOEHRINGER INGELHEIM VETMEDICA GMBH, Duluth, GA (US)

(72) Inventors: Michel Bublot, Chaponost (FR); Teshome Mebatsion, Watkinsville, GA (US); Joyce Pritchard, Gainesville, GA (US); Perry Linz, Jefferson, GA (US); Aemro Kassa, Watkinsville, GA (US)

(73) Assignee: BOEHRINGER INGELHEIM ANIMAL HEALTH USA INC., Duluth, GA (US)

(*) Notice: Subject to any disclaimer, the term of this patent is extended or adjusted under 35 U.S.C. 154(b) by 0 days.

(21) Appl. No.: 17/812,732

(22) Filed: Jul. 15, 2022

(65) Prior Publication Data

US 2023/0175017 A1 Jun. 8, 2023

Related U.S. Application Data

(63) Continuation of application No. 17/035,109, filed on Sep. 28, 2020, now Pat. No. 11,421,249, which is a continuation of application No. 16/393,743, filed on Apr. 24, 2019, now Pat. No. 10,822,620, which is a continuation of application No. 15/840,764, filed on Dec. 13, 2017, now Pat. No. 10,323,257.

(60) Provisional application No. 62/433,842, filed on Dec. 14, 2016.

(51) Int. Cl.

| | |
|---|---|
| ***C12N 15/869*** | (2006.01) |
| ***A61K 39/12*** | (2006.01) |
| ***A61K 39/155*** | (2006.01) |
| ***A61K 39/245*** | (2006.01) |
| ***A61K 39/295*** | (2006.01) |
| ***C07K 14/03*** | (2006.01) |
| ***C07K 14/08*** | (2006.01) |
| ***C12N 7/00*** | (2006.01) |

(52) U.S. Cl.

CPC ............ *C12N 15/869* (2013.01); *A61K 39/12* (2013.01); *A61K 39/155* (2013.01); *A61K 39/245* (2013.01); *A61K 39/295* (2013.01); *C07K 14/03* (2013.01); *C07K 14/08* (2013.01); *C12N 7/00* (2013.01); *C12N 2710/16311* (2013.01); *C12N 2710/16334* (2013.01); *C12N 2710/16343* (2013.01); *C12N 2710/16363* (2013.01); *C12N 2720/10034* (2013.01); *C12N 2760/16163* (2013.01); *C12N 2760/18134* (2013.01); *C12N 2760/18163* (2013.01); *C12N 2830/20* (2013.01); *C12N 2830/50* (2013.01); *C12N 2840/203* (2013.01)

(58) Field of Classification Search

CPC .. A61K 39/12; A61K 39/295; A61K 2039/53; C12N 2710/16334; C12N 2710/20034; C12N 2760/18134

See application file for complete search history.

(56) References Cited

U.S. PATENT DOCUMENTS

| | | | | |
|---|---|---|---|---|
| 6,306,400 | B1 | 10/2001 | Bublot et al. | |
| 2014/0147457 | A1 | 5/2014 | Bublot et al. | |
| 2016/0375122 | A1* | 12/2016 | Mebatsion ............. | A61K 39/12 424/186.1 |
| 2017/0043006 | A1* | 2/2017 | Reddy ...................... | C12N 7/00 |

FOREIGN PATENT DOCUMENTS

| | | | | |
|---|---|---|---|---|
| CN | 103072306 | A | 5/2013 | |
| CN | 103074306 | A | 5/2013 | |
| CN | 106701693 | A | 5/2017 | |
| JP | H11503009 | A | 3/1999 | |
| JP | 2001513630 | A | 9/2001 | |
| JP | 2006055171 | A | 3/2006 | |
| JP | 2015500631 | A | 1/2015 | |
| JP | 2015500806 | A | 1/2015 | |
| WO | 1996005291 | A1 | 2/1996 | |
| WO | 1996029396 | A1 | 9/1996 | |
| WO | 1998037216 | A1 | 8/1998 | |
| WO | WO-0105988 | A1 * | 1/2001 | ............. A61K 39/12 |
| WO | 2013057235 | A1 | 4/2013 | |
| WO | 2013057236 | A1 | 4/2013 | |
| WO | 2013082317 | A2 | 6/2013 | |
| WO | 2013082327 | A1 | 6/2013 | |
| WO | 2018112051 | A1 | 6/2018 | |

OTHER PUBLICATIONS

Hall RN, Meers J, Fowler EV, Mahony TJ. Identification of non-essential loci within the Meleagrid herpesvirus 1 genome. Virol J. Aug. 27, 2015;12:130. (Year: 2015).*

Zai X, Shi B, Shao H, Qian K, Ye J, Yao Y, Nair V, Qin A. Identification of a Novel Insertion Site HVT-005/006 for the Generation of Recombinant Turkey Herpesvirus Vector. Front Microbiol. May 25, 2022; 13:886873. (Year: 2022).*

Zhang F, Chen W, Ma C, Zhang Z, Zhao P, Du Y, Zhang Y, Duan L, Fang J, et al. Transcriptional activity comparison of different sites in recombinant Marek's disease virus for the expression of the H9N2 avian influenza virus hemagglutinin gene. J Virol Methods. Oct. 2014;207:138-45. Epub Jul. 14, 2014. (Year: 2014).*

(Continued)

*Primary Examiner* — Rachel B Gill

(57) ABSTRACT

The present invention provides recombinant herpesvirus of turkeys (HVT) vectors that contain and express antigens of avian pathogens, compositions comprising the recombinant HVT vectors and polyvalent vaccines comprising the recombinant HVT vectors. The present invention further provides methods of vaccination against a variety of avian pathogens and method of producing the recombinant HVT vectors.

20 Claims, 34 Drawing Sheets

Specification includes a Sequence Listing.

(56) References Cited

OTHER PUBLICATIONS

López de Juan Abad BA, Cortes AL, Correa M, Gimeno IM. Evaluation of Factors That Influence Dose Variability of Marek's Disease Vaccines. Avian Dis. Dec. 2019;63(4):591-598. (Year: 2019).*
Atasoy, MO, 2021. Herpesvirus of Turkeys as a vaccine vector in viral diseases: Pros and cons. Hosts and Viruses, 8(3): 13-20. (Year: 2021).*
Linda Gergen et al., "A double recombinant 1-20 herpesvirus of turkeys for the protection of chicken against Newcastle, infectious laryngotracheitis and Marke's diseases", Avian Pathology, vol. 48, No. 1, Jan. 1, 2019, pp.45-56.
Gimeno Isabel M., Cortes Aneg L., Guy James S., et al. "Replication of recombinant herpesvirus of turkey expressing genes of infectious laryngotracheitis virus in specific pathogen free and broiler chickens following…". Avian pathology 40.4 (Aug. 2011): 395-403.
Johnson (2010); Avian Dis. 54(4):1251-1258.
Zhao (2014); J. Virol. 88(15):8397-8406.
Jin Hee Kim, et al., "High Cleavage Efficiency of a 2A Peptide Derived from Porcine Teschovirus-1 in Human Cell Lines, Zebrafish and Mice", PLos One, 2011, vol. 6, Part 4, e18556.
Kingham et al., The genome of herpesvirus of turkeys: comparative analysis with Marek's disease viruses, Journal of General Virology, 2001, 82(5):1123-1135.
First page of GenBank acc. Nr. NC_002641: genome of HVT strain FC-126 (first seen 2001).
First page of GenBank accession No. NC_003985: genome of porcine Teschovirus-1 (first seen 2002).
Ngoi et al., Current Gene Therapy, vol. 4, 2004, pp. 15-31.
Liu et al., Viruses, vol. 2, 2016, p. 301.
English Abstract of CN103074306A.

* cited by examiner

Figure 1

| SEQ ID NO: | type | Gene Description |
|---|---|---|
| 1 | DNA | Polynucleotide encoding IBDV VP2 |
| 2 | protein | IBDV VP2 |
| 3 | DNA | Polynucleotide encoding NDV-F of NDV strain VIId, codon-optimized in pFSV40VP2 (vHVT309) and pFIRESVP2 (vHVT310) |
| 4 | DNA | Polynucleotide encoding NDV-F of NDV strain VIId, wild-type in pFP2AVP2 (vHVT311), pFwtSV40VP2 (vHVT313), pVP2IRESFwt (vHVT316) and pFwtIRESgD (vHVT322) |
| 5 | protein | NDV-F protein (vHVT309, vHVT310, vHVT311, vHVT313, vHVT316, vHVT322) |
| 6 | DNA | mCMV IE promoter for IBDV VP2 |
| 7 | DNA | SV40 Promoter for NDV F and ILTV gD |
| 8 | DNA | SV40 Poly A |
| 9 | DNA | Synthetic Poly A |
| 10 | DNA | IRES in pFIRESVP2, pVP2IRESgD and pVP2IRESFwt |
| 11 | DNA | Polynucleotide encoding P2A in pFP2AVP2 |
| 12 | DNA | Plasmid pFSV40VP2 for vHVT309 |
| 13 | DNA | Plasmid pFIRESVP2 for vHVT310 |
| 14 | DNA | Plasmid pFP2AVP2 for vHVT311 |
| 15 | DNA | Plasmid pVP2IRESgD for vHVT317 |
| 16 | DNA | Polynucleotide encoding ILTV gD, wild-type in pVP2IRESgD (vHVT317), HVT US2SVgDwtsyn (vHVT407), pHVTIG1gDCaFopt (vHVT308), pFwtIRESgD (vHVT322), and pHVTUS2SVgDwtsyn (vHVT406) |
| 17 | protein | ILTV gD |
| 18 | DNA | Plasmid pFwtSV40VP2 for vHVT313 |
| 19 | DNA | Plasmid pVP2IRESFwt for vHVT316 |
| 20 | DNA | Plasmid HVT US2SVgDwtsyn for vHVT407 |
| 21 | DNA | Polynucleotide encoding NDV-F of genotype V, codon-optimized in pHVTIG1gDCaFopt (vHVT308) |
| 22 | protein | NDV-F of genotype V (vHVT308) |
| 23 | DNA | HHV3gB promoter (reverse direction) |
| 24 | DNA | HHV3gB promoter |
| 25 | DNA | Plasmid pHVTIG1gDCaFopt for vHVT308 |
| 26 | DNA | Plasmid pFwtIRESgD for vHVT322 |
| 27 | DNA | pHVTUS2SVgDwtsyn for vHVT406 |

Genome Structure of HVT and Insertion Sites

Genomic Structure of HVT, ORFs of the *BamHI* fragment, and Insertion/Replacement Locations (GenBank accession number for HVT FC126 sequence: AF291866.1)

pFSV40VP2 plasmid map pFSV40VP2.

7505 bp

Schematic representation of primer binding sites for vHVT309 vHVT309 Identity PCR

| M 1 2 3 | M 1 2 3 | M 1 2 3 | M 1 2 3 | M 1 2 3 |
|---|---|---|---|---|
| MB080+MB081 | MB080+ NDVFVIIdopt.F | MB080+VP2.F | SV40tailR+ mCMVF | syntailR+ SV40promoterF |

Lane 1: no template
Lane 2: Vaxxitek
Lane 3: vHVT309 pFIRESVP2 plasmid map

Schematic representation of primer binding sites for vHVT310 vHVT310 identity PCR

| M 1 2 3 | M 1 2 3 | M 1 2 3 | M 1 2 3 |
|---|---|---|---|
| MB080+MB081 | MB080+ NDVFVIIdopt.F | MB080+ VP2.F | SV40tailR+ mCMVF |

Lane 1:   no template
Lane 2:   Vaxxitek
Lane 3:   vHVT310 pFP2AVP2 plasmid map

Schematic representation of primer binding sites for vHVT311 vHVT311 identity PCR

| M 1 2 3 | M 1 2 3 | M 1 2 3 | M 1 2 3 |
|---|---|---|---|
| MB080+MB081 | MB080+<br>NDVFVIIdwt.F | MB080+<br>VP2.F | SV40tailR+<br>mCMVF |

Lane 1: no template
Lane 2: Vaxxitek
Lane 3: vHVT311 pVP2IRESgD plasmid map pVP2IRESgD in pUC57
6901 bp

Schematic representation of primer binding sites for vHVT317 vHVT317 identity PCR

Lane 1: no template
Lane 2: Vaxxitek
Lane 3: vHVT317 pFwtSV40VP2 plasmid map

Schematic representation of primer binding sites for vHVT313 vHVT313 identity PCR

Lane 1: no template
Lane 2: Vaxxitek
Lane 3: vHVT313 pVP2IRESFwt plasmid map

Schematic representation of primer binding sites for vHVT316

Fragment of vHVT316 with primers
7406 bp (molecule 164411 bp)

Labels: IG1 Arm, MB080, SV40tailR, SV40 Poly A, 312P6, VIId NDV-Fwt, IRES, VP2.F, VP2, MCMV, mCMVF, MB081, IG1 Arm vHVT316 identity PCR Lane 1: no template
Lane 2: Vaxxitek
Lane 3: vHVT316

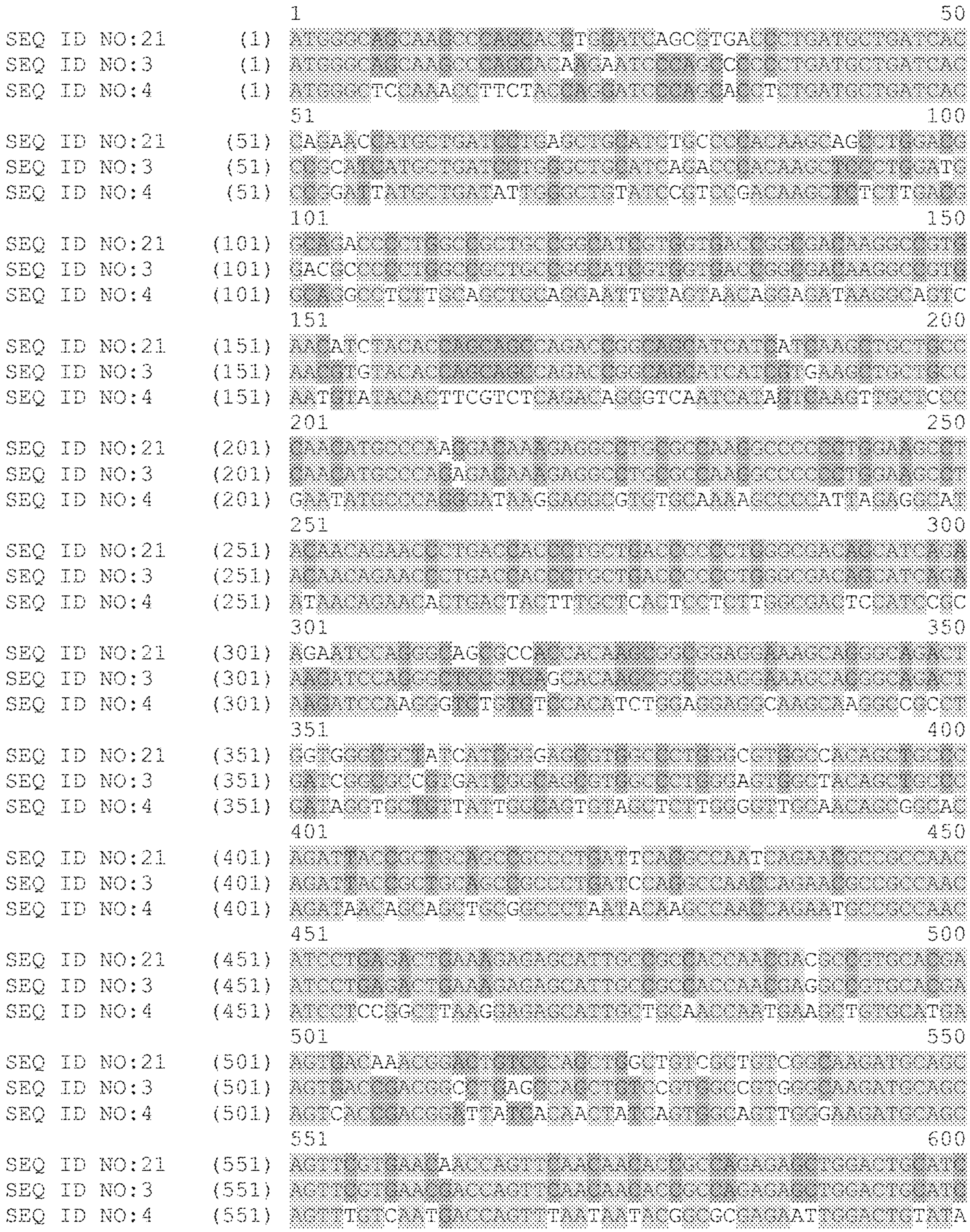

Figure 21A

Sequence alignments of NDV F polynucleotides

```
                        1                                                  50
SEQ ID NO:21    (1)     ATGGGC..CAA..C...ACT..ATCAGCTGA..T..TGCTGAT.AC
SEQ ID NO:3     (1)     ATGGGC..CAA..C...CAA.AAT...GCC...TGATGCTGATCAC
SEQ ID NO:4     (1)     ATGG.TCCAAA.TTCTA...AT...GA..T.TGATGCTGATCAC
                        51                                                 100
SEQ ID NO:21    (51)    AGAA.C.ATG.TGAT..T.GA..TGA.T.TCCC..CAA.CAG..T..A.
SEQ ID NO:3     (51)    ..CA..AATG.TGAT..T..GCTC.ATCAGA..CAGAA..C..T.CAT.
SEQ ID NO:4     (51)    ..GA.TATG.TGATATT..GCTTA..CCT..GACAAG..TCTTGA.
                        101                                                150
SEQ ID NO:21    (101)   ..AC.............GGAT..T.TC...............AAGGC..
SEQ ID NO:3     (101)   GACGC..T..GC.T..T..GGAT..T....A..GG.CGA.AAGGC.T.
SEQ ID NO:4     (101)   ..GGCT.TT..AG.TG.AG.AATT..AC..AA.A.GA.TAAGGCATC
                        151                                                200
SEQ ID NO:21    (151)   AA.AT.T.AC...............AGA..GG...TCAT.AT.AAG.TGT.GC.
SEQ ID NO:3     (151)   AA..TG.AC...........CAGA..GG.C.A.TCAT..TGAAG.T.C.GC.
SEQ ID NO:4     (151)   AAT..A.A..ACTTCGTCT.AGA.ACGGTCAA.CA.A..T.AAGT..C.CC.
                        201                                                250
SEQ ID NO:21    (201)   ..A.ATC.CA.G..A.AA.G.AGC..G.C.AAACC.C..T.CAAC.T
SEQ ID NO:3     (201)   AA.ATC.CA.GACAA.A.GAGCG.G.C.AAACC.C..T.CAA.C.T
SEQ ID NO:4     (201)   GA.T.TC..CA..GAT.AAG.AGGG..TCAAAC.C..AT.A.AGC.A.
                        251                                                300
SEQ ID NO:21    (251)   ..AA.AGAAC..TGA.TA..TCCT...C.T.T..G.GCCAC..A.T..
SEQ ID NO:3     (251)   A.AA.AGAAC..TGA.CA..TCCT.AG.C.T.A.G.GCCAC..A.T.C.
SEQ ID NO:4     (251)   .TAA.AGAACA.TGA.TAGTTT.GCTCA.TCT.T.T.GGAGTCATC.C
                        301                                                350
SEQ ID NO:21    (301)   .GAAT.CA..GG.AG..GCC...ACA...G.GAGG.AA.C.AG.GC.T.
SEQ ID NO:3     (301)   ...AT.CA.C..T...G.ACA..G..G.AACC.AG.GC.T.
SEQ ID NO:4     (301)   ...AT.CAACGG.T..T..T.CACATCT.GAG.AG.CAA..AGCCC.CT
                        351                                                400
SEQ ID NO:21    (351)   .G.GC...TA.CA.T..GAG.CT..C.T..CCT..GCAC.AAG.T.
SEQ ID NO:3     (351)   G..CCG.GCC..GAT.GC..GT..C.T..GAG..CTACAG.C.T.
SEQ ID NO:4     (351)   G..ACGT.C.T.TATTC..AGTCTA..T.TTGG.T.C.AAC.AGCGCAC
                        401                                                450
SEQ ID NO:21    (401)   .GAT...AGCC..G..GG...GGT.TT.A.CCAAT..GAA.GC.C.AA.
SEQ ID NO:3     (401)   .GAT..GAGC..G..GG...ATCCA..C.CAA.A.AA.G.C.AAC.
SEQ ID NO:4     (401)   .GATAA.AC.AC.T.CGGG...AA.A.AA.CAA..AGA.T.C.GC.AAC
                        451                                                500
SEQ ID NO:21    (451)   ATCCT.C...G.T.AAG.AGG.CATTG...GCA.AA.GAC.C.TGCA.A
SEQ ID NO:3     (451)   ATCCT.C...G.T.AAG.AGG.CATTG...GCA.AA.GAG.C.TGCA.A
SEQ ID NO:4     (451)   ATCCTCCG.CT.AAG.AG.CATTG.TCAA.CAATGAA.T.TGCAT.A
                        501                                                550
SEQ ID NO:21    (501)   AGT.A.AAACC...T.AG..AC.TG.CT.C.T.CC..AGATC.AGC
SEQ ID NO:3     (501)   AGT.AC.AAC.GC.T.AG..AC.TG..CCT.GCC..GCA.AGATC.AGC
SEQ ID NO:4     (501)   AGTCAC..AGC..GT.AA..AACTA..AGT.AC.AGTT.GAAGATCAGC
                        551                                                600
SEQ ID NO:21    (551)   AGTT..T.AA.AA..ACT.GAA.AA.AC..C..GAG.T..GACTGAT
SEQ ID NO:3     (551)   AGTT..T.AA.GAC.GT.GAA.AA.AC..C..GAG.T..GACTGAT
SEQ ID NO:4     (551)   AGT.T.TCCAAT.ACACT.TAAT.AT.CG.GCAG.AAT..GACTGTATA
```

Figure 21B

```
                          601                                               650
SEQ ID NO:21    (601)     AAGATCGCCCAGCAGGTGGCGCTGGAGCTGAACCTGTACCTGACCCAGGT
SEQ ID NO:3     (601)     AAGATCACCCAGCAGGTGGCGCTGGAGCTGAACCTGTACCTGACCCAGGT
SEQ ID NO:4     (601)     AAAATCACACAACAGGTTGGTGTAGAACTCAACCTATACCTAACTGAATT
                          651                                               700
SEQ ID NO:21    (651)     GACCACAGTGTTCGCGCCGCAGATCACGAGCCCCGCTGTGACCCAGCTGA
SEQ ID NO:3     (651)     GACCACAGTGTTCGCGCCGCAGATCACGAGCCCACCCGTGACACAGCTGA
SEQ ID NO:4     (651)     GACTACAGTATTCGGGCCACAGATCACCTCCCCTGCATTAACTCAGCTGA
                          701                                               750
SEQ ID NO:21    (701)     CAATCCAGGCGCTGTACAAGGTGGCTGGCGGCAAGATGGAGTACGTGGTG
SEQ ID NO:3     (701)     CCATCCAGGCGCTGTACAAGGTGGCTGGCGGCAAGATGGAGTACGTGGTG
SEQ ID NO:4     (701)     CCATCCAGGCACTTTATAATTTAGCTGGTGGCAATATGGATTACTTATTA
                          751                                               800
SEQ ID NO:21    (751)     ACGAAGCTGGCGAGTGGGCAACAAGCAGCTGGGCAGGCTGATGGGTCCGG
SEQ ID NO:3     (751)     ACAAAGCTGGCGAATCGGCAACAAGCAGCTGGGCAGGCTGATGGAGGCGG
SEQ ID NO:4     (751)     ACGAAGTTACGTGTAGGGAACAATCAACTCAGCTCGTTAATTGGTGGCGG
                          801                                               850
SEQ ID NO:21    (801)     GCTGATCACAGGCAACCCCATGCTGTACGACGAGCAGACCCAGCTGGTGG
SEQ ID NO:3     (801)     GCTGATCACCGGCAACCCCATGCTGTACGACGAGCAGACCCAGCTGGTGG
SEQ ID NO:4     (801)     GCTGATCACTGGTAACCCTATACTGTATGACTCACAGACTCAACTCTGGG
                          851                                               900
SEQ ID NO:21    (851)     GCATGCAGATCAAGCTGCCAGAGCTGGAAGCGCTGAAGAAGATGACAGCC
SEQ ID NO:3     (851)     GCATGCAGGTGAAGCTGCCAGCGCTGGCCAGCCTGAAGAAGATCGCCGCC
SEQ ID NO:4     (851)     GCATACAAGTGAATTTACCTGCAGTCGGGAACTTAAATAATATCGATGCC
                          901                                               950
SEQ ID NO:21    (901)     ACCTACGTGCAGACCGTGAGCGTGCCCACCACCAAGGCGCTGGCCCAGGC
SEQ ID NO:3     (901)     ACCTACGTGCAGACCGTGAGCGTGCCCACCACCAAGGCGCTGGCCCAGGC
SEQ ID NO:4     (901)     ACCTATTTGCAGACCTTATCTGTAAGTACAACCAAAGGATCTGCCTCAGC
                          951                                              1000
SEQ ID NO:21    (951)     GCTGCTGCCCAAGCTGGTGACACAGCTGCCGAGCCTGATCGAGGCAGCTG
SEQ ID NO:3     (951)     GCTGCTGCCCAAGCTGGTCACACAGCTGCCGAGCCTGATCGAGGCAGCTG
SEQ ID NO:4     (951)     ACTTGTCCGGAAACTAGTCACACAAGTCGGTTCCCTGATAGAAGAGCTTG
                          1001                                             1050
SEQ ID NO:21   (1001)     ACACCGAGTACTGCATGGACGAGCGCGACATCGAGGTGTACGTGGACGTG
SEQ ID NO:3    (1001)     ACACCGAGTACTGCATGGACGAGCGCGAGCTGGAGGTGTACGTGCACATC
SEQ ID NO:4    (1001)     ACACCTCATACTGTATACAGTCCGATGTGATTTATATTGTACTAGAAATA
                          1051                                             1100
SEQ ID NO:21   (1051)     GTGACCTTCCCGATCGAGCCGCGCATGTACGAGCTCGTCAGCGGCAACAC
SEQ ID NO:3    (1051)     GTGACCTTCCCGATCGAGCCGCGCATGTACGAGCTCGTCAGCGGCAACAC
SEQ ID NO:4    (1051)     GTGACATTCCCCATGTCCCCAGGTATTTATTCCTGTTTCAGCGGCAACAC
                          1101                                             1150
SEQ ID NO:21   (1101)     GGCGCCCTGCATGTACGAGAAGACCGCAAGCAGCACTGACCACCCCTACA
SEQ ID NO:3    (1101)     GGCGCCCTGCATGTACGAGAAGACCGCAAGCGGCACTGACCACCCCTACA
SEQ ID NO:4    (1101)     ATCAGCTTGCATGTATTCAAAGACTGAAGCGGCACTCACTACGGCGGATA
                          1151                                             1200
SEQ ID NO:21   (1151)     TGGCCCTGAAGGCGAGGCTGATCGCCAAGTCGAAGATGACCACCTGCACA
SEQ ID NO:3    (1151)     TGGCCCTGAAGGCGAGGCTGATCGCCAAGTCGAAGATCACCACCTGCACA
SEQ ID NO:4    (1151)     TGGCCCTTAAGGCTCACTTATTGCCAATTGTAAAATAACAACATGTACA
                          1201                                             1250
SEQ ID NO:21   (1201)     TCGGCGCACCCGCCAGGCATCATCGAGCAGAAGTACGGCGAGCGCGCGGC
SEQ ID NO:3    (1201)     TCGGCGCACCCGCCAGGCATCATCGAGCAGAAGTACGGCGAGCGCGCGGC
SEQ ID NO:4    (1201)     TGTGCACACCCTGCTGGTATCATATCGCAAAATTATGCAGAAGCTGCATC
```

Figure 21C

```
                           1251                                              1300
SEQ ID NO:21   (1251)  CCTGATGGACCAAGCATTCGTGTAGGCTGTTGTCCTTGCATGCGATGACAC
SEQ ID NO:3    (1251)  CCTGATGGATCCCCATTCTTGTAAGGTGTTGTCCTTGGAGGCGATGACAC
SEQ ID NO:4    (1251)  CCTGATAGAGCAACATTCGTGCAATGTCTTATCATTAGAAGGGATAACTC
                           1301                                              1350
SEQ ID NO:21   (1301)  TGAGACTGACGGCGCAGTTGGACGCGACCTAGCAGAAGAACATCAGCATG
SEQ ID NO:3    (1301)  TGAGACTGACGGCGCAGTTGGAGCGCACCTAGCAGAAGAACATCAGCATG
SEQ ID NO:4    (1301)  TAAGGCTCAGTGGGCAATTTGAGGCAACTTATCAAAAGAACATCTCAATA
                           1351                                              1400
SEQ ID NO:21   (1351)  CTGGAGGAGCAGCTGATCCTGACGGGCAAGCTGGAGATGGAGACGCAGCT
SEQ ID NO:3    (1351)  CTGGAGGAGCAGCTGATCCTGACGGGCAAGCTGGAGATGGAGACGCAGCT
SEQ ID NO:4    (1351)  CTAGATTCTCAAGTCATCCTGACAGGCAATCTTGATATATCAACTGAACT
                           1401                                              1450
SEQ ID NO:21   (1401)  GCGGAACGTGAAGAAGGAGATCAGCAGGACCGTGGAGAAGGTGGCGGAGT
SEQ ID NO:3    (1401)  GCGGAACGTGAATAAGGAGATCAGCAGGGCCGTGGAGAAGATGGCGGAGG
SEQ ID NO:4    (1401)  TCGAAACGTCAAGAATTCAATCAGCAATGCCTTGGATAGGTTGGCACAAG
                           1451                                              1500
SEQ ID NO:21   (1451)  CCAACAACAAGCTGAACAAAGTGAAGCTGGAGCTGACGGAGTACGAGGCC
SEQ ID NO:3    (1451)  GCAACAGCAAGCTGGAGAAAGTGAAGCTGCAGCTGACATCCACTGAGGCG
SEQ ID NO:4    (1451)  GCAACAGCAACCTAGAGAAAGTCAATCTCGAACTAACGGGCACGAGTGCG
                           1501                                              1550
SEQ ID NO:21   (1501)  CTGATGACCTAGATGGTGCTGGCGATGGTGGAGGCTGGCCTTCGGGGTGAT
SEQ ID NO:3    (1501)  CTGATGACCTAGATGGTGCTGACGGTGATCAGGCTGGGGTTCGGGGCGT
SEQ ID NO:4    (1501)  CTCATTACCTATATTGTTCTAGCTGGGATTGTTCTAGGTTTCGGTGGAGT
                           1551                                              1600
SEQ ID NO:21   (1551)  CAGGCTGGTGGTGGCGTCGTACCTGATGTACAAGCAGAGACGGCAGCAGA
SEQ ID NO:3    (1551)  GAGGCTGGTGGTGGCGTCGTACCTGATGTACAAGCAGAAGCGGCAGCAGA
SEQ ID NO:4    (1551)  TAGTCTGGTGTTAGCGTGTTACCTGATGTACAAACAGAAGGCACAACAAA
                           1601                                              1650
SEQ ID NO:21   (1601)  AGACCGTGCTGTGGCTGGCGAAGAAGACCCTGGAGCAGATGAGGCCACG
SEQ ID NO:3    (1601)  AGACCGTGCTGTGGCTGGCGAACAAGACCCTGGAGCAGATGAGGCCACG
SEQ ID NO:4    (1601)  AGACCTTGCTATGGCTTGGGAAGAATACCCTCGATCAGATGAGGCCACT
                           1651
SEQ ID NO:21   (1651)  ACGAGAACG
SEQ ID NO:3    (1651)  ACGAGAACG
SEQ ID NO:4    (1651)  ACAAGAGCA
```

Sequence identity between SEQ ID NO:3 and SEQ ID NO:4 is 72.2%.
Sequence identity between SEQ ID NO:21 and SEQ ID NO:3 is 92.1%
Sequence identity between SEQ ID NO:21 and SEQ ID NO:4 is 69.4%

Figure 21D

Sequence alignments of NDV F proteins

| | | |
|---|---|---|
| | | 1 50 |
| SEQ ID NO:22 | (1) | MGSKPSTWISVTLMLITRTMLILSCICPTSSLDGRPLAAAGIVVTGDKAV |
| SEQ ID NO:5 | (1) | MGSKPSTRIPAPLMLITRIMLILGCIRPTSSLDGRPLAAAGIVVTGDKAV |
| | | 51 100 |
| SEQ ID NO:22 | (51) | NIYTSSQTGSIIVKLLPNMPKDKEACAKAPLEAYNRTLTTLLTPLGDSIR |
| SEQ ID NO:5 | (51) | NVYTSSQTGSIIVKLLPNMPKDKEACAKAPLEAYNRTLTTLLTPLGDSIR |
| | | 101 150 |
| SEQ ID NO:22 | (101) | RIQGSAVTSGGGKQGRLVGAIIGSVALGVATAAQITAAAALIQANQNAAN |
| SEQ ID NO:5 | (101) | KIQGSVVTSGGGKQGRLIGAVIGSVALGVATAAQITAAAALIQANQNAAN |
| | | 151 200 |
| SEQ ID NO:22 | (151) | ILRLKESIAATNQAVHEVTNGLSQLAVAVGKMQQFVNNQFNNTARELDCI |
| SEQ ID NO:5 | (151) | ILRLKESIAATNEAVHEVTDGLSQLAVAVGKMQQFVNDQFNNTARELDCI |
| | | 201 250 |
| SEQ ID NO:22 | (201) | KIAQQVGVELNLYLTELTTVFGPQITSPALTQLTIQALYNLAGGNMDYLL |
| SEQ ID NO:5 | (201) | KITQQVGVELNLYLTELTTVFGPQITSPALTQLTIQALYNLAGGNMDYLL |
| | | 251 300 |
| SEQ ID NO:22 | (251) | TKLGVGNNQLSSLIGSGLITGNPILYDSQTQLLGIQVNLPSVGSLNNMRA |
| SEQ ID NO:5 | (251) | TKLGIGNNQLSSLIGSGLITGYPILYDSQTQLLGIQVNLPSVGNLNNMRA |
| | | 301 350 |
| SEQ ID NO:22 | (301) | TYLETLSVSTTKGFASALVPKVVTQVGSVIEELDTSYCIESDLDLYCTRI |
| SEQ ID NO:5 | (301) | TYLETLSVSTTKGFASALVPKVVTQVGSVIEELDTSYCIESDLDLYCTRI |
| | | 351 400 |
| SEQ ID NO:22 | (351) | VTFPMSPGIYSCLSGNTSACMYSKTEGALTTPYMALKGSVIANCKMTTCR |
| SEQ ID NO:5 | (351) | VTFPMSPGIYSCLSGNTSACMYSKTEGALTTPYMALKGSVIANCKMTTCR |
| | | 401 450 |
| SEQ ID NO:22 | (401) | CADPFGIISQNYGEAVSLIDKHSCSVLSLDGITLRLSGEFDATYQKNISI |
| SEQ ID NO:5 | (401) | CTDPFGIISQNYGEAVSLIDKHSCNVLSLDGITLRLSGEFDATYQKNISI |
| | | 451 500 |
| SEQ ID NO:22 | (451) | LDSQVIVTGNLDISTELGNVNNSISSTLDKLAESNNKLNKVNVNLTSTSA |
| SEQ ID NO:5 | (451) | LDSQVIVTGNLDISTELGNVNNSISNALDKLAESNSKLEKVNVRLTSTSA |
| | | 501 550 |
| SEQ ID NO:22 | (501) | LITYIVLAIISLAFGVISLVLACYLMYKQKAQQKTLLWLGNNTLDQMRAT |
| SEQ ID NO:5 | (501) | LITYIVLTIISLVFGAISLVLACYLMYKQKAQQKTLLWLGNNTLDQMRAT |
| | | 551 |
| SEQ ID NO:22 | (551) | TRT |
| SEQ ID NO:5 | (551) | TRA |

SEQ ID NO:5 and SEQ ID NO:22 is 91.9% identical.

HVT US2SVgDwtsyn plasmid map pHVTIG1gDCaFopt map

HVTIG1gDCaFopt
9331 bp

Labels: Intergene 1 arm, SV40 polyA, ILTgD, HHV3 gB, SV40 Promoter, NDV-F-CA02-CSmut, Syn Poly a tail, Intergene 1 arm, amp Schematic representation of primer binding sites for vHVT308 vHVT308 Identity PCR

Lane 1: no template
Lane 2: HVT FC126
Lane 3: vHVT308 pre-MSV
Lane 4: vHVT308 pre-MSV+13 passages pFwtIRESgD plasmid pFwtIRESgD 10138 bp Schematic representation of primer binding sites for vHVT322

Fragment of vHVT322 with primers
6762 bp (molecule 164341 bp)

Labels: IG1 Arm, MB080, SV40PolyA.R1, SV40 Poly A, ILTV gD wildtype, ILTgDwtF, IRES, 312P6, NDV-F VIId wt, pMCMV, mCMVF, MB081, IG1 Arm vHVT322 Identity PCR Lane 1: no template
Lane 2: vHVT13
Lane 3: vHVT322 pre-MSV
Lane 4: vHVT322 pre-MSV+13 pHVTUS2SVgDwtsyn plasmid map

Schematic representation of primer binding sites for vHVT406 vHVT406 Identity PCR

Lane 1: no template

Lane 2: FC126

Lane 3: donor plasmid pHVTUS2SVgDwtsyn

Lane 4: vHVT406 pre-MSV

Lane 5: vHVT406 pre-MSV+13

RECOMBINANT HVT VECTORS EXPRESSING MULTIPLE ANTIGENS OF AVIAN PATHOGENS AND USES THEREOF

CROSS-REFERENCE TO RELATED APPLICATIONS

This application is a continuation of U.S. patent application Ser. No. 16/393,743, filed Apr. 24, 2019, now U.S. Pat. No. 10,822,620, which is a continuation of U.S. patent application Ser. No. 15/840,764, filed Dec. 13, 2017, now U.S. Pat. No. 10,323,257, which claims the benefit of U.S. Application No. 62/433,842, filed Dec. 14, 2016, the entire contents of which are hereby incorporated by reference herein.

SEQUENCE LISTING

This application contains a sequence listing which has been submitted electronically in XML format. The sequence listing accompanying this application is hereby incorporated by reference in its entirety. Said XML copy, created on Feb. 8, 2023, is named MER16-307-US-5_SL.xml and is 94,243 bytes in size.

FIELD OF THE INVENTION

The invention relates to recombinant viral vectors for the insertion and expression of foreign genes for use as safe immunization vehicles to protect against a variety of pathogens. It also relates to multivalent composition or vaccine comprising one or more recombinant viral vectors for protection against a variety of pathogens. The present invention relates to methods of making and using the recombinant viral vectors.

BACKGROUND OF THE INVENTION

Poultry vaccination is widely used to protect poultry flocks against devastating diseases including Newcastle disease (ND), infectious bursal disease (IBD), Marek's disease (MD), infectious bronchitis (IB), infectious laryngotracheitis (ILT) and avian influenza (AI). ND is caused by the avian paramyxovirus 1 (APMV-1) also designated ND virus (NDV) belonging to the Paramyxoviridae family. MD is caused by Gallid herpesvirus 2 (Herpesviridae family) also designated as MD virus serotype 1 (MDV1). IB is caused by IB virus (IBV) belonging to the Coronaviridae family, ILT is caused by Gallid herpesvirus 1 (Herpesviridae family) also designated ILT virus (ILTV) and AI is caused by AI virus (AIV) belonging to the Orthomyxoviridae family.

A number of recombinant avian viral vectors have been proposed with a view to vaccinating birds against these avian pathogens. The viral vectors used comprise avipox viruses, especially fowlpox (EP-A-0,517,292), Marek's virus, such as serotypes 1, 2 and 3 (HVT) (WO87/04463; WO2013/082317), or alternatively the ITLV, NDV and avian adenovirus. When some of these recombinant avian viral vectors were used for vaccination, they display variable levels of protection.

Several recombinant herpesvirus of turkeys (HVT, also designated Meleagrid herpesvirus 1 or MDV serotype 3) vectors expressing antigens from various pathogens (U.S. Pat. Nos. 5,980,906, 5,853,733, 6,183,753, 5,187,087) including IBDV, NDV, ILTV and AIV have been developed and licensed. Of particular interest is a HVT vector-expressing IBDV VP2 protective gene that has shown clear advantages over classical IBD vaccines (Bublot et al J. Comp. Path. 2007, Vol. 137, S81-S84; U.S. Pat. No. 5,980,906). Other HVT vectors of interest are those expressing either NDV (Morgan et al 1992, Avian dis. 36, 858-70; U.S. Pat. Nos. 6,866,852; 5,650,153), ILTV (Johnson et al, 2010 Avian Dis 54, 1251-1259; U.S. Pat. Nos. 6,299,882; 5,853,733, EP 1801204), or NDV and IBDV (U.S. Pat. No. 9,114,108; WO2016102647, WO2013/057235, WO2015032910, WO2013144355) protective gene(s). US2016/0158347 reported the use of the oligodeoxynucleotide TLR21 agonist to increase the immune response against the antigen that expressed by HVT vector.

One of the practical problems of using several HVT-based recombinant vaccines together is their interference. Lower protection is induced at least against one of the disease when two HVT recombinants expressing different antigens are mixed (Rudolf Heine 2011; Issues of the Poultry Recombinant Viral Vector Vaccines which May Cause an Effect on the Economic Benefits of those Vaccines; paper presented at the XVII World Veterinary Poultry Association (WVPA) Congress in Cancun, Mexico, Aug. 14-18, 2011; Slacum G, Hein R. and Lynch P., 2009, The compatibility of HVT recombinants with other Marek's disease vaccines, $58^{th}$ Western Poultry Disease Conference, Sacramento, CA, USA, March $23^{rd}$-$25^{th}$, p 84).

Considering the potential effect of animal pathogens, such as NDV and IBDV on veterinary public health and the economy, efficient methods of preventing infection and protecting animals are needed. There is a need for a solution of combined effective vector vaccines and a suitable method for making the vaccine that could alleviate the problem of interference observed between two HVT-based vector vaccines.

SUMMARY OF THE INVENTION

The present invention showed surprising result when polyvalent compositions or vaccines comprising recombinant HVT vector were effective to protect animals against a variety of avian pathogens without interference. Surprising results were also observed when various combinations of promoters/linkers, codon-optimized gene, polyA tails and insertion sites conferred different levels of efficacy and stability to the expression of one or more heterologous genes in vivo and in vitro. The present invention provides stable HVT vectors which are able to efficiently express multiple genes and overcomes the well-known problem that HVT vectors with multiple inserts are less stable.

The present invention relates to a recombinant HVT vector comprising one, two or more heterologous polynucleotides coding for and expressing at least one antigen of an avian pathogen.

The present invention provides a composition or vaccine comprising one or more recombinant HVT vectors comprising one, two or more heterologous polynucleotides coding for and expressing at least one antigen of an avian pathogen.

The present invention relates to a method of vaccinating an animal, or inducing an immunogenic or protective response in an animal, comprising at least one administration of the composition or vector of the present invention.

BRIEF DESCRIPTION OF THE DRAWINGS

The following detailed description, given by way of example, and which is not intended to limit the invention to specific embodiments described, may be understood in conjunction with the accompanying figures, incorporated herein by reference, in which:

FIG. 1 is a table showing the SEQ ID NO assigned to each DNA and protein sequence.

FIG. 21A-21D depict DNA and protein sequence alignments.

DETAILED DESCRIPTION OF THE INVENTION

Figure 2:
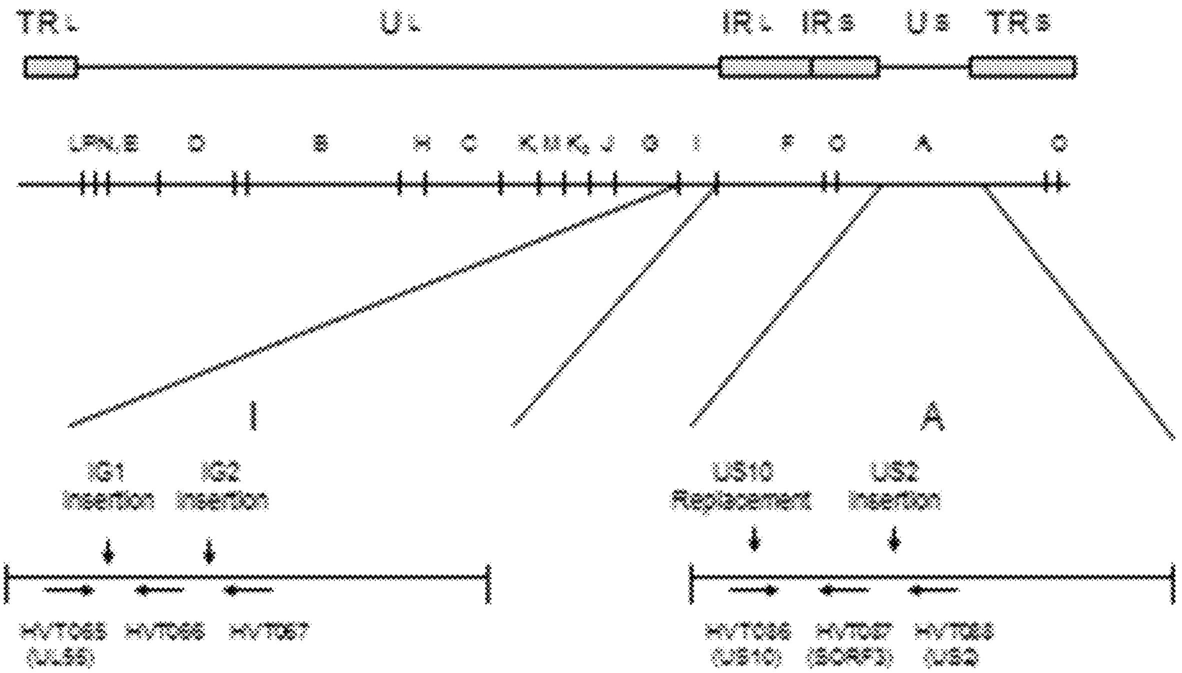
FIG. 2 depicts the genome structure of HVT and its insertion sites.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims. This invention includes all modifications and equivalents of the subject matter recited in the aspects or claims presented herein to the maximum extent permitted by applicable law.

It is noted that in this disclosure and particularly in the claims, terms such as “comprises”, “comprised”, “comprising” and the like can have the meaning attributed to it in U.S. Patent law; e.g., they can mean “includes”, “included”, “including”, and the like; and that terms such as “consisting essentially of” and “consists essentially of” have the meaning ascribed to them in U.S. Patent law, e.g., they allow for elements not explicitly recited, but exclude elements that are found in the prior art or that affect a basic or novel characteristic of the invention.

The singular terms “a,” “an,” and “the” include plural referents unless context clearly indicates otherwise. Similarly, the word “or” is intended to include “and” unless the context clearly indicate otherwise. The word “or” means any one member of a particular list and also includes any combination of members of that list.

It will also be understood that, although the terms first, second, etc. may be used herein to describe various elements, these elements should not be limited by these terms. These terms are only used to distinguish one element from another. For example, a first gesture could be termed a second gesture, and, similarly, a second gesture could be termed a first gesture, without departing from the scope of the present invention. All methods or processes described herein can be performed in any suitable order unless otherwise indicated herein or otherwise clearly contradicted by context.

The term “animal” is used herein to include all mammals, birds and fish. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle), swine (e.g., pig), ovine (e.g., sheep, goats, lamas, bisons), avian (e.g., chicken, duck, goose, turkey, quail, pheasant, parrot, finches, hawk, crow, ostrich, emu and cassowary), primate (e.g., prosimian, tarsier, monkey, gibbon, ape), humans, and fish. The term “animal” also includes an individual animal in all stages of development, including embryonic and fetal stages.

The term “about” as used herein, means approximately, in the region of, roughly, or around. When the term “about” is used in conjunction with a numerical range, it modifies that range by extending the boundaries above and below the numerical values set forth. In general, the term “about” is used herein to modify a numerical value above and below the stated value by a variance of 10%. In one aspect, the term “about” means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term “about.”

The terms “polypeptide” and “protein” are used interchangeably herein to refer to a polymer of consecutive amino acid residues.

The term “nucleic acid”, “nucleotide”, and “polynucleotide” are used interchangeably and refer to RNA, DNA, cDNA, or cRNA and derivatives thereof, such as those containing modified backbones. It should be appreciated that the invention provides polynucleotides comprising sequences complementary to those described herein. The “polynucleotide” contemplated in the present invention includes both the forward strand (5' to 3') and reverse complementary strand (3' to 5'). Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "genomic DNA" or "genome" is used interchangeably and refers to the heritable genetic information of a host organism. The genomic DNA comprises the DNA of the nucleus (also referred to as chromosomal DNA) but also the DNA of the plastids (e.g., chloroplasts) and other cellular organelles (e.g., mitochondria). The genomic DNA or genome contemplated in the present invention also refers to the RNA of a virus. The RNA may be a positive strand or a negative strand RNA. The term "genomic DNA" contemplated in the present invention includes the genomic DNA containing sequences complementary to those described herein. The term "genomic DNA" also refers to messenger RNA (mRNA), complementary DNA (cDNA), and complementary RNA (cRNA).

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene; Doree S M et al.; Pandher K et al.; Chung J Y et al.), transcription terminators (in general the terminator is located within approximately 50 nucleotides downstream of the stop codon of the coding sequence or gene; Ward C K et al.). Gene or polynucleotide also refers to a nucleic acid fragment that expresses mRNA or functional RNA, or encodes a specific protein, and which includes regulatory sequences.

The term "heterologous DNA" as used herein refers to the DNA derived from a different organism, such as a different cell type or a different species from the recipient. The term also refers a DNA or fragment thereof on the same genome of the host DNA wherein the heterologous DNA is inserted into a region of the genome which is different from its original location.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The term "immunogenic protein or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. For example, linear epitopes may be determined by e.g., concurrently synthesizing large numbers of peptides on solid supports, the peptides corresponding to portions of the protein molecule, and reacting the peptides with antibodies while the peptides are still attached to the supports. Similarly, conformational epitopes are readily identified by determining spatial conformation of amino acids such as by, e.g., x-ray crystallography and 2-dimensional nuclear magnetic resonance.

The term "immunogenic protein or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The terms "recombinant" and "genetically modified" are used interchangeably and refer to any modification, alteration or engineering of a polynucleotide or protein in its native form or structure, or any modification, alteration or engineering of a polynucleotide or protein in its native environment or surrounding. The modification, alteration or engineering of a polynucleotide or protein may include, but is not limited to, deletion of one or more nucleotides or amino acids, deletion of an entire gene, codon-optimization of a gene, conservative substitution of amino acids, insertion of one or more heterologous polynucleotides.

The terms "polyvalent vaccine or composition", "combination or combo vaccine or composition" and "multivalent vaccine or composition" are used interchangeably to refer to a composition or vaccine containing more than one composition or vaccines. The polyvalent vaccine or composition may contain two, three, four or more compositions or vaccines. The polyvalent vaccine or composition may comprise recombinant viral vectors, active or attenuated or killed wild-type viruses, or a mixture of recombinant viral vectors and wild-type viruses in active or attenuated or killed forms.

One embodiment of the invention provides a recombinant HVT viral vector comprising one, two or more heterologous polynucleotides coding for and expressing at least one antigen or polypeptide of an avian pathogen. The HVT strains used for the recombinant viral vector may be any HVT strains, including, but not limited to, the HVT strain FC126 (Igarashi T. et al., J. Gen. Virol. 70, 1789-1804, 1989).

The genes coding for antigen or polypeptide may be those coding for Newcastle Disease Virus fusion protein (NDV-F), Newcastle Disease Virus hemagglutinin neuraminidase (NDV-HN), Marek's Disease Virus glycoprotein C (gC), Marek's Disease Virus glycoprotein B (gB), Marek's Disease Virus glycoprotein E (gE), Marek's Disease Virus glycoprotein I (gI), Marek's Disease Virus glycoprotein H (gH) or Marek's Disease Virus glycoprotein L (gL), Infectious Bursal Disease Virus (IBDV) VP2, IBDV VPX, IBDV VP3, IBDV VP4, ILTV glycoprotein B, ILTV glycoprotein I, ILTV UL32, ILTV glycoprotein D, ILTV glycoprotein E, ILTV glycoprotein C, influenza hemagglutinin (HA), influenza neuraminidase (NA), protective genes derived from *Mycoplasma gallisepticum* (MG), or *Mycoplasma synoviae* (MS), or combinations thereof. The antigen or polypeptide may be any antigen from the poultry pathogen selected form the group consisting of avian encephalomyelitis virus, avian reovirus, avian paramyxovirus, avian metapneumovirus, avian influenza virus, avian adenovirus, fowl pox virus, avian coronavirus, avian rotavirus, chick anemia virus, avian astrovirus, avian parvovirus, avian retrovirus, avian picornavirus, coccidiosis (*Eimeria* sp.), *Campylobacter* sp., *Salmonella* sp., *Pasteurella* sp., *Avibacterium* sp., *Mycoplasma gallisepticum, Mycoplasma synoviae, Clostridium* sp., and *Escherichia coli.*

Moreover, homologs of aforementioned antigen or polynucleotides are intended to be within the scope of the present invention. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type polypeptide can differ from the wild-type polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the polynucleotide or polypeptide sequences of antigens described above, and will exhibit a similar function.

In one embodiment, the present invention provides a recombinant HVT viral vector comprising one, two or more heterologous polynucleotides coding for and expressing the NDV-F antigen or polypeptide, the IBDV VP2 antigen or polypeptide, the ILTV gD antigen or polypeptide, or a combination thereof. In one aspect of the embodiment, the NDV-F antigen or polypeptide has at least 70%, 75%, 80%, 85%, 90%, 95%, 96%, 97%, 98% or 99% sequence identity to a polypeptide having the sequence as set forth in SEQ ID NO:5 or 22, or a conservative variant, an allelic variant, a homolog or an immunogenic fragment comprising at least eight or at least ten consecutive amino acids of one of these polypeptides, or a combination of these polypeptides. In another aspect of the embodiment, the heterologous polynucleotide encodes an NDV-F antigen or polypeptide having at least 70%, 75%, 80%, 85%, 90%, 95%, 96%, 97%, 98% or 99% sequence identity to a polypeptide having the sequence as set forth in SEQ ID NO:5. In yet another aspect of the embodiment, the heterologous polynucleotide has at least 70%, 75%, 80%, 85%, 90%, 95%, 96%, 97%, 98% or 99% sequence identity to a polynucleotide having the sequence as set forth in SEQ ID NO:3, 4 or 21.

In another aspect of the embodiment, the IBDV VP2 antigen or polypeptide has at least 70%, 75%, 80%, 85%, 90%, 95%, 96%, 97%, 98% or 99% sequence identity to a polypeptide having the sequence as set forth in SEQ ID NO:2, or a conservative variant, an allelic variant, a homolog or an immunogenic fragment comprising at least eight or at least ten consecutive amino acids of one of these polypeptides, or a combination of these polypeptides. In another aspect of the embodiment, the heterologous polynucleotide encodes an IBDV VP2 antigen or polypeptide having at least 70%, 75%, 80%, 85%, 90%, 95%, 96%, 97%, 98% or 99% sequence identity to a polypeptide having the sequence as set forth in SEQ ID NO:2. In yet another aspect of the embodiment, the heterologous polynucleotide has at least 70%, 75%, 80%, 85%, 90%, 95%, 96%, 97%, 98% or 99% sequence identity to a polynucleotide having the sequence as set forth in SEQ ID NO:1.

In another aspect of the embodiment, the ILTV gD antigen or polypeptide has at least 70%, 75%, 80%, 85%, 90%, 95%, 96%, 97%, 98% or 99% sequence identity to a polypeptide having the sequence as set forth in SEQ ID NO:17, or a conservative variant, an allelic variant, a homolog or an immunogenic fragment comprising at least eight or at least ten consecutive amino acids of one of these polypeptides, or a combination of these polypeptides. In another aspect of the embodiment, the heterologous polynucleotide encodes an ILTV gD antigen or polypeptide having at least 70%, 75%, 80%, 85%, 90%, 95%, 96%, 97%, 98% or 99% sequence identity to a polypeptide having the sequence as set forth in SEQ ID NO:17. In yet another aspect of the embodiment, the heterologous polynucleotide has at least 70%, 75%, 80%, 85%, 90%, 95%, 96%, 97%, 98% or 99% sequence identity to a polynucleotide having the sequence as set forth in SEQ ID NO:16.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

The term "identity" with respect to sequences can refer to, for example, the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman). The sequence identity or sequence similarity of two amino acid sequences, or the sequence identity between two nucleotide sequences can be determined using Vector NTI software package (Invitrogen, 1600 Faraday Ave., Carlsbad, CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for NDV-F, IBDV VP2 or ILTV gD polypeptides, the DNA sequence of these genes can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of NDV F, IBDV VP2 or ILTV gD protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the NDV-F, IBDV VP2 or ILTV gD polypeptide encoded by the nucleotide sequence is functionally unchanged.

Successful expression of the heterologous polynucleotides by the recombinant/modified infectious virus requires two conditions. First, the heterologous polynucleotides must be inserted or introduced into a region of the genome of the virus in order that the modified virus remains viable. The second condition for expression of inserted heterologous polynucleotides is the presence of a regulatory sequences allowing expression of the gene in the viral background (for instance: promoter, enhancer, donor and acceptor splicing sites and intron, Kozak translation initiation consensus sequence, polyadenylation signals, untranslated sequence elements).

The insertion site may be any non-essential region of the HVT genome, including, but not limited to, the region between the STOP codon of ORF UL55 and the junction of UL with the adjacent repeat region (intergenic region 1, the IG1 locus, U.S. Pat. No. 5,980,906), the IG2 (intergenic region 2) locus, the IG3 (intergenic region 3) locus, the UL43 locus, the US10 locus, the US2 locus, the SORF3/US2 locus (see FIG. 2)

In general, it is advantageous to employ a strong promoter functional in eukaryotic cells. The promoters include, but are not limited to, an immediate early (IE) human cytomegalovirus (CMV) (hCMV) promoter, mouse CMV (mCMV) IE promoter, guinea pig CMV (gpCMV) IE promoter, an SV40 promoter, Pseudorabies Virus promoters such as that of glycoprotein X promoter, Herpes Simplex Virus-1 such as the alpha 4 promoter, Marek's Disease Viruses (including MDV-1, MDV-2 and HVT) promoters such as those driving glycoproteins gC, gB, gE, or gI expression, HHV3gB promoter (Human Herpesvirus Type 3 glycoprotein B promoter), Infectious Laryngotracheitis Virus promoters such as those of glycoprotein gB, gE, gI, gD, gC genes, or other herpesvirus promoters.

One embodiment of the invention provides a recombinant HVT vector comprising a first heterologous polynucleotide coding for and expressing the IBDV VP2 antigen or polypeptide and a second polynucleotide coding for and expressing the NDV-F antigen or polypeptide. In one aspect of the embodiment, the NDV-F antigen or polypeptide has at least 70%, 75%, 80%, 85%, 90%, 95%, 96%, 97%, 98% or 99% sequence identity to a polypeptide having the sequence as set forth in SEQ ID NO:5. In another aspect of the embodiment, the IBDV VP2 antigen or polypeptide has at least 70%, 75%, 80%, 85%, 90%, 95%, 96%, 97%, 98% or 99% sequence identity to a polypeptide having the sequence as set forth in SEQ ID NO:2. In another aspect, the polynucleotide encoding the NDV-F polypeptide is operably linked to the SV40 promoter having the sequence as set forth in SEQ ID NO:7 and the expression of NDV-F antigen or polypeptide is regulated by the SV40 promoter. In yet another aspect, the expression of NDV-F antigen or polypeptide is regulated by the SV40 polyA signal having the sequence as set forth in SEQ ID NO:8, or the synthetic polyA signal having the sequence as set forth in SEQ ID NO:9. In another aspect, the expression of IBDV VP2 antigen or polypeptide is regulated by the mCMV-IE promoter having the sequence as set forth in SEQ ID NO:6 and the SV40 polyA signal having the sequence as set forth in SEQ ID NO:8, or the synthetic polyA signal having the sequence as set forth in SEQ ID NO:9.

Another embodiment of the invention provides a recombinant HVT vector comprising a first heterologous polynucleotide coding for and expressing the IBDV VP2 antigen or polypeptide and a second polynucleotide coding for and expressing the NDV-F antigen or polypeptide, and further comprising a sequence which regulates the expression of the second polynucleotide. The regulatory sequences or linkers may be an internal ribosome entry site (IRES), an RNA sequence derived from Encephalomyocarditis virus (EMCV), or a sequence encoding a self-cleaving porcine teschovirus-1 2A or foot and mouth disease virus (FMDV) peptide (P2A).

In one aspect of the embodiment, the recombinant HVT vector comprises a first polynucleotide encoding the IBDV VP2 antigen and a second polynucleotide encoding the NDV-F antigen, and further comprises the IRES having the sequence as set forth in SEQ ID NO:10. In another aspect of the embodiment, the recombinant HVT comprises a first polynucleotide encoding the IBDV VP2 antigen and a second polynucleotide encoding the NDV-F antigen, and further comprises the P2A encoding polynucleotide having the sequence as set forth in SEQ ID NO:11.

One embodiment of the invention provides a recombinant HVT vector comprising a first heterologous polynucleotide coding for and expressing the NDV F antigen or polypeptide and a second polynucleotide coding for and expressing the ILTV gD antigen or polypeptide, and further comprising a sequence which regulates the expression of the second polynucleotide. The regulatory sequences or linkers may be an internal ribosome entry site (IRES), an RNA sequence derived from Encephalomyocarditis virus (EMCV), or a sequence encoding a self-cleaving porcine teschovirus-1 2A or foot and mouth disease virus (FMDV) peptide (P2A). In one aspect of the embodiment, the ILTV gD antigen or polypeptide has at least 70%, 75%, 80%, 85%, 90%, 95%, 96%, 97%, 98% or 99% sequence identity to a polypeptide having the sequence as set forth in SEQ ID NO:17. In another aspect of the embodiment, the NDV F antigen or polypeptide has at least 70%, 75%, 80%, 85%, 90%, 95%, 96%, 97%, 98% or 99% sequence identity to a polypeptide having the sequence as set forth in SEQ ID NO:5 or 22. In yet another aspect of the embodiment, the recombinant HVT vector comprises a first polynucleotide encoding the NDV F antigen and a second polynucleotide encoding the ILTV gD antigen, and further comprises the IRES having the sequence as set forth in SEQ ID NO:10.

Another embodiment of the invention provides a recombinant HVT vector comprising a first heterologous polynucleotide coding for and expressing the NDV F antigen or polypeptide and a second polynucleotide coding for and expressing the ILTV gD antigen or polypeptide. In one aspect of the embodiment, the ILTV gD antigen or polypeptide has at least 70%, 75%, 80%, 85%, 90%, 95%, 96%, 97%, 98% or 99% sequence identity to a polypeptide having the sequence as set forth in SEQ ID NO:17. In another aspect of the embodiment, the NDV F antigen or polypeptide has at least 70%, 75%, 80%, 85%, 90%, 95%, 96%, 97%, 98% or 99% sequence identity to a polypeptide having the sequence as set forth in SEQ ID NO:5 or 22. In one aspect, the polynucleotide encoding the NDV F polypeptide is operably linked to the SV40 promoter and the expression of NDV F antigen or polypeptide is regulated by the SV40 promoter. In another aspect, the polynucleotide encoding the ILTV gD polypeptide is operably linked to the HHV3gB promoter and the expression of ILTV gD antigen or polypeptide is regulated by the HHV3gB promoter. In yet another aspect, the HHV3gB promoter is in the reverse direction. In yet another aspect, the expressions of the NDV F antigen and ILTV gD antigen are regulated by SV40 promoter and reverse HHV3gB promoter, and are in opposite directions.

Another embodiment of the invention provides a recombinant HVT vector comprising a first heterologous polynucleotide coding for and expressing the IBDV VP2 antigen or polypeptide and a second polynucleotide coding for and expressing the ILTV gD antigen or polypeptide. In one aspect of the embodiment, the ILTV gD antigen or polypeptide has at least 70%, 75%, 80%, 85%, 90%, 95%, 96%, 97%, 98% or 99% sequence identity to a polypeptide having the sequence as set forth in SEQ ID NO:17. In another aspect of the embodiment, the IBDV VP2 antigen or polypeptide has at least 70%, 75%, 80%, 85%, 90%, 95%, 96%, 97%, 98% or 99% sequence identity to a polypeptide having the sequence as set forth in SEQ ID NO:2. In yet another aspect of the embodiment, the recombinant HVT vector comprises a first polynucleotide encoding the IBDV VP2 antigen and a second polynucleotide encoding the ILTV gD antigen, and further comprises the IRES having the sequence as set forth in SEQ ID NO:10.

Another embodiment of the invention provides a recombinant HVT vector comprising a heterologous polynucleotide coding for and expressing the ILTV gD antigen or polypeptide. In one aspect of the embodiment, the ILTV gD antigen or polypeptide has at least 70%, 75%, 80%, 85%, 90%, 95%, 96%, 97%, 98% or 99% sequence identity to a polypeptide having the sequence as set forth in SEQ ID NO:17. In another aspect of the embodiment, the polynucleotide encoding the ILTV gD polypeptide is operably linked to the SV40 promoter and the expression of ILTV gD antigen or polypeptide is regulated by the SV40 promoter.

In one embodiment, the polynucleotides encoding the IBDV VP2 antigen, and/or NDV-F antigen, and/or ILTV gD antigen may be inserted in one or more locus regions selected from the group consisting of IG1, IG2, US10, US2, SORF3-US2 and gD of HVT genome. In another embodiment, the polynucleotides encoding the IBDV VP2 antigen, and/or NDV-F antigen, and/or ILTV gD antigen are inserted in the same locus, such as IG1 of HVT genome.

In one embodiment, the present invention relates to a pharmaceutical composition or vaccine comprising one or more recombinant HVT vectors of the present invention and a pharmaceutically or veterinarily acceptable carrier, excipient, vehicle or adjuvant. The HVT vector may comprise two heterologous polynucleotides, and wherein the first polynucleotide comprises a polynucleotide encoding a polypeptide selected from the group consisting of an Infectious Bursal Disease Virus (IBDV) VP2 antigen, an Infectious Laryngotracheitis Virus (ILTV) glycoprotein D (gD) antigen and a Newcastle Disease Virus F (NDV-F) antigen, and wherein the second polynucleotide comprises a polynucleotide encoding a polypeptide selected from the group consisting of an Infectious Bursal Disease Virus (IBDV) VP2 antigen, an Infectious Laryngotracheitis Virus (ILTV) glycoprotein D (gD) antigen and a Newcastle Disease Virus F (NDV-F) antigen.

In another embodiment, the present invention provides a composition or vaccine comprising an HVT viral vector comprising: i) a first heterologous polynucleotide coding for and expressing an IBDV VP2 antigen or an NDV-F antigen; ii) a second polynucleotide coding for and expressing an NDV-F antigen or an IBDV VP2 antigen; and iii) optionally a pharmaceutically or veterinarily acceptable carrier, excipient, vehicle or adjuvant. In yet another embodiment, the present invention provides a composition or vaccine comprising an HVT viral vector comprising: i) a first heterologous polynucleotide coding for and expressing an IBDV VP2 antigen or an ILTV gD antigen; ii) a second polynucleotide coding for and expressing an ILTV gD antigen or an IBDV VP2; and iii) optionally a pharmaceutically or veterinarily acceptable carrier, excipient, vehicle or adjuvant. In yet another embodiment, the present invention provides a composition or vaccine comprising an HVT viral vector comprising: i) a first heterologous polynucleotide coding for and expressing an NDV-F antigen or an ILTV gD antigen; ii) a second polynucleotide coding for and expressing an ILTV gD antigen or an NDV-F antigen; and iii) optionally a pharmaceutically or veterinarily acceptable carrier, excipient, vehicle or adjuvant. In yet another embodiment, the present invention provides a composition or vaccine comprising an HVT viral vector comprising a heterologous polynucleotide coding for and expressing an ILTV gD antigen, and optionally a pharmaceutically or veterinarily acceptable carrier, excipient, vehicle or adjuvant. In yet another embodiment, the present invention provides a composition or vaccine comprising an HVT comprising a polynucleotide having at least 70%, 75%, 80%, 85%, 90%, 95%, 96%, 97%, 98% or 99% sequence identity to a polynucleotide having the sequence as set forth in SEQ ID NO:1, 3, 4, 12, 13, 14, 15, 16, 18, 19, 20, 21, 25, 26 or 27. In one embodiment, it is shown that insertion of two or more heterologous polynucleotides in one locus confers better protection and efficacy then insertion in multiple loci. In another embodiment, it is shown that expressing more than one heterologous polynucleotide from a single mRNA through an IRES or P2A provides better protection and efficacy against avian diseases. In yet another embodiment, the experimental data provided by the present invention disclose that constructs comprising IRES elements provided better protection than constructs comprising P2A elements.

The pharmaceutically or veterinarily acceptable carriers or adjuvant or vehicles or excipients are well known to the one skilled in the art. For example, a pharmaceutically or veterinarily acceptable carrier or adjuvant or vehicle or excipient can be Marek's disease vaccine diluent used for MD vaccines. Other pharmaceutically or veterinarily acceptable carrier or adjuvant or vehicle or excipients that can be used for methods of this invention include, but are not limited to, 0.9% NaCl (e.g., saline) solution or a phosphate buffer, poly-(L-glutamate), the Lactated Ringer's Injection diluent (sodium chloride, sodium lactate, potassium chloride and calcium chloride), or polyvinylpyrrolidone. The pharmaceutically or veterinarily acceptable carrier or vehicle or adjuvant or excipients may be any compound or combination of compounds facilitating the administration of the vector (or protein expressed from an inventive vector in vitro), or facilitating transfection or infection and/or improve preservation of the vector (or protein). Doses and dose volumes are herein discussed in the general description and can also be determined by the skilled artisan from this disclosure read in conjunction with the knowledge in the art, without any undue experimentation.

Optionally other compounds may be added as pharmaceutically or veterinarily acceptable carriers or adjuvants or vehicles or excipients, including, but not limited to, alum; CpG oligonucleotides (ODN), in particular ODN 2006, 2007, 2059, or 2135 (Pontarollo R. A. et al., Vet. *Immunol. Immunopath,* 2002, 84: 43-59; Wernette C. M. et al., Vet. *Immunol. Immunopath,* 2002, 84: 223-236; Mutwiri G. et al., *Vet. Immunol. Immunopath,* 2003, 91: 89-103); polyA-polyU, dimethyldioctadecylammonium bromide (DDA) ("Vaccine Design The Subunit and Adjuvant Approach", edited by Michael F. Powell and Mark J. Newman, *Pharmaceutical Biotechnology,* 6: p. 03, p. 157); N,N-dioctadecyl-N',N'-bis(2-hydroxyethyl) propanediamine (such as AVRIDINE®) (*Ibid*, p. 148); carbomer, chitosan (see U.S. Pat. No. 5,980,912).

The pharmaceutical compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

In one embodiment, the adjuvant may include TS6 TS7, TS8 and TS9 (U.S. Pat. No. 7,371,395), LR2, LR3 and LR4 (U.S. Pat. No. 7,691,368), TSAP (US20110129494), TRIGEN™ (Newport Labs), synthetic dsRNAs (e.g. poly-IC, poly-ICLC [HILTONOL®]), and MONTANIDE™ adjuvants (W/O, W/O/W, O/W, IMS and Gel; all produced by SEPPIC).

In another embodiment, the invention provides for the administration of a therapeutically effective amount of a vaccine or composition for the delivery of recombinant HVT vectors in a target cell. Determination of the therapeutically effective amount is routine experimentation for one of ordinary skill in the art.

Another aspect of the invention relates to a method for inducing an immunological response in an animal against one or more antigens or a protective response in an animal against one or more avian pathogens, which method comprises inoculating the animal at least once with the vaccine or pharmaceutical composition of the present invention. Yet another aspect of the invention relates to a method for inducing an immunological response in an animal to one or more antigens or a protective response in an animal against one or more avian pathogens in a prime-boost administration regimen, which is comprised of at least one primary administration and at least one booster administration using at least one common polypeptide, antigen, epitope or immunogen. The immunological composition or vaccine used in primary administration may be same, may be different in nature from those used as a booster.

The avian pathogens may be Newcastle Disease Virus (NDV), Infectious Bursal Disease Virus (i.e., IBDV or Gumboro Disease virus), Marek's Disease Virus (MDV), Infectious Laryngotracheitis Virus (ILTV), avian encephalomyelitis virus, avian reovirus, avian paramyxovirus, avian metapneumovirus, avian influenza virus, avian adenovirus, fowl pox virus, avian coronavirus, avian rotavirus, avian parvovirus, avian astrovirus and chick anemia virus coccidiosis (*Eimeria* sp.), *Campylobacter* sp., *Salmonella* sp., *Mycoplasma gallisepticum, Mycoplasma synoviae, Pasteurella* sp., *Avibacterium* sp., *E. coli* or *Clostridium* sp.

Usually, one administration of the vaccine in avian is performed either at one day-of-age by the subcutaneous or intramuscular route or in ovo in 17-19 day-old embryo. A second administration can be done within 0-30 days after the first administration.

A variety of administration routes in day-old chicks may be used such as subcutaneously or intramuscularly, intradermally, transdermally. The in ovo vaccination can be performed in the amniotic sac and/or the embryo. Commercially available in ovo and SC administration devices can be used for vaccination.

The composition or vaccine may contain a dose from about $10^2$ to about $10^{20}$, about $10^3$ to about $10^{18}$, about $10^4$ to about $10^{16}$, about $10^5$ to about $10^{12}$ VLPs (virus like particles) produced in vitro or in vivo from a viral vector, a plasmid, or baculovirus. The viral vector may be titrated based on any virus titration methods including, but not limited to, FFA (Focus Forming Assay) or FFU (Focus Forming Unit), $TCID_{50}$ (50% Tissue Culture Infective Dose), PFU (Plaque Forming Units), and $FAID_{50}$ (50% Fluorescent Antibody Infectious Dose), and the VLPs produced in vitro can be titrated by hemagglutination assay, ELISA, and electron microscopy. Other methods may also be applicable depending on the type of VLP.

The composition or vaccine may contain from about $10^{2.0}$ to about $10^{7.0}$ $TCID_{50}$ or PFU/dose, from about $10^{2.0}$ to about $10^{7.0}$ $TCID_{50}$ or PFU/dose, and from about $10^{2.0}$ to about $10^{6.5}$ $TCID_{50}$ or PFU/dose.

The dose volumes can be between about 0.01 and about 10 ml, between about 0.01 and about 5 ml.

The invention will now be further described by way of the following non-limiting examples.

EXAMPLES

Construction of DNA inserts, plasmids and recombinant viral vectors was carried out using the standard molecular biology techniques described by J. Sambrook et al. (Molecular Cloning: A Laboratory Manual, 4th edition, Cold Spring Harbor Laboratory, Cold Spring Harbor, New York., 2014).

Example 1 Construction of Recombinant HVT Vectors Expressing Two Genes

Example 1.1 Construction of Recombinant vHVT309 Expressing IBDV-VP2 and NDV-F The objective of the study is to construct a recombinant HVT in which an expression cassette containing a mouse cytomegalovirus promoter (mCMV), a gene encoding an infectious bursal disease virus viral protein 2 (VP2), Simian virus 40 poly A tail (SV40 poly A), Simian virus 40 promoter (SV40 promoter), a gene encoding a Newcastle disease virus fusion protein (NDV-F) and synthetic poly A tail (syn poly A tail) is integrated in the intergenic site 1 (IG1).

The parental virus used in the construct is vHVT13 (an HVT vector expressing the IBDV VP2 gene, active ingredient of Merial's VAXXITEK® (HVT+IBD) Vaccine, also known as vHVT17 in U.S. Pat. No. 5,980,906). The vHVT13 vector contains an expression cassette composed of mCMV IE promoter (SEQ ID NO:6), IBDV VP2 gene (SEQ ID NO:1 encoding SEQ ID NO:2), and SV40 poly A tail (SEQ ID NO:8) inserted into the IG1 insertion site. A Newcastle disease virus Fusion Protein (NDV-F) corresponding to genotype VIId sequence was chemically synthesized and codon optimized (GenScript). The F protein cleavage site of this synthetic gene was altered to match a lentogenic F cleavage site sequence and the resultant NDV-F gene sequence has 99% amino acid sequence identity to NDV-F sequence deposited in GenBank (AY337464). Mouse CMV IE promoter was used for IBD-VP2, and SV40 promoter was used for NDV-F. The insertion locus is intergenic site 1 (IG1) in HVT (FIG. 2). Donor plasmid pFSV40VP2 (an insertion plasmid containing the VP2/SV40 poly A and flanking arm of IG1+SV40 promoter+NDV-F+synthetic poly A) was constructed as described below. Chicken embryo fibroblast cells (CEF) were used for in vitro recombination.

Donor Plasmid Construction

Figure 3:
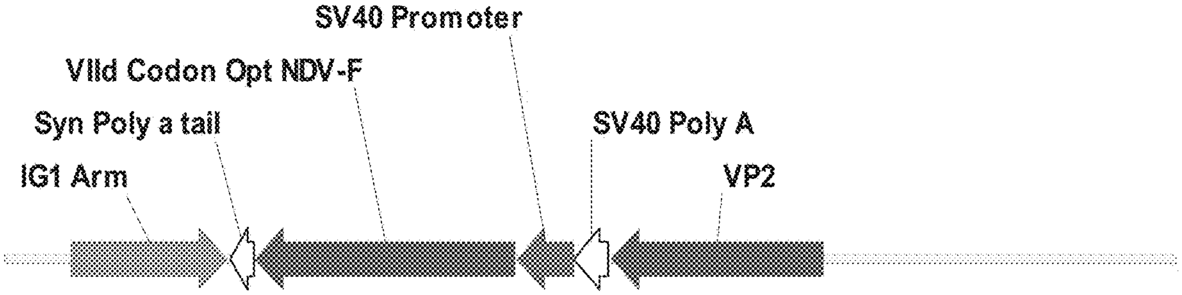
FIG. 3 depicts pFSV40VP2 plasmid map.

Synthetic DNA in pUC57 containing the IBDV VP2 gene (SEQ ID NO:1 encoding SEQ ID NO:2), SV40 poly A tail (SEQ ID NO:8), SV40 promoter (SEQ ID NO:7), NDV-F gene (SEQ ID NO:3 encoding SEQ ID NO:5), and synthetic poly A tail (SEQ ID NO:9) was synthesized by GeneScript (FIG. 3). The plasmid, pFSV40VP2 was transformed using Top10 Oneshot kit (cat #C404002, Invitrogen) and a large scale culture was grown and plasmid extraction was done using Qiagens Maxi Prep kit. Transient expression of the maxi prep was verified using Fugene Transfection Reagent in Chicken Embryo Fibroblast Cells (CEF's) and chicken polyclonal sera against NDV.

Recombinant Generation

A standard homologous recombination procedure was followed by co-electroporation of secondary CEF cells using pFSV40VP2 plasmid and viral DNA isolated from vHVT13 Vaccine. Co-electroporation was performed using $1\times10^7$ 2° CEF in 300 μl Opti-MEM and shocked at 150 volts with 950 capacitance in a 2 mm electroporation cuvette. The transfected cells were seeded into 96-well plate and incubated for 4 days. The cells grown in the 96-well plate were then duplicated into two 96-well plates and incubated for 3 more days. One set of 96-well plates was used for IFA using chicken polyclonal sera against NDV-F to identify positive wells containing recombinants and another set of 96-well plates was used for recovering the infected cells from the positive wells.

The recombinant viral purification methods were performed first by 96-well plate duplication and IFA selection for the wells containing the most IFA positive plaques with the least amount of IFA negative plaques. Wells matching those criteria were then harvested and adjusted to 1 ml in DMEM+2% FBS. From the 1 ml stock, 5-20 ul were removed and mixed with $1\times10^7$ CEFs in 10 ml DMEM+2% FBS and aliquoted onto a new 96-well plate to have single virus plaques per well. The 96-well plates were duplicated after 5 days of incubation and wells that contained plaques were tested for the presence of double recombinant and absence of vHVT13 parental virus by IFA and PCR. Again the wells that appeared to have more recombinant virus, by comparing the PCR banding results, were harvested and adjusted to 1 ml and aliquoted onto new 96-well plates. After two rounds of purification of virus infected cells, recombinant virus expressing NDV-F protein was isolated and the purity of the recombinant virus was tested by IFA and PCR to confirm the absence of parental virus.

Analysis of Recombinant by PCR

Figure 4:
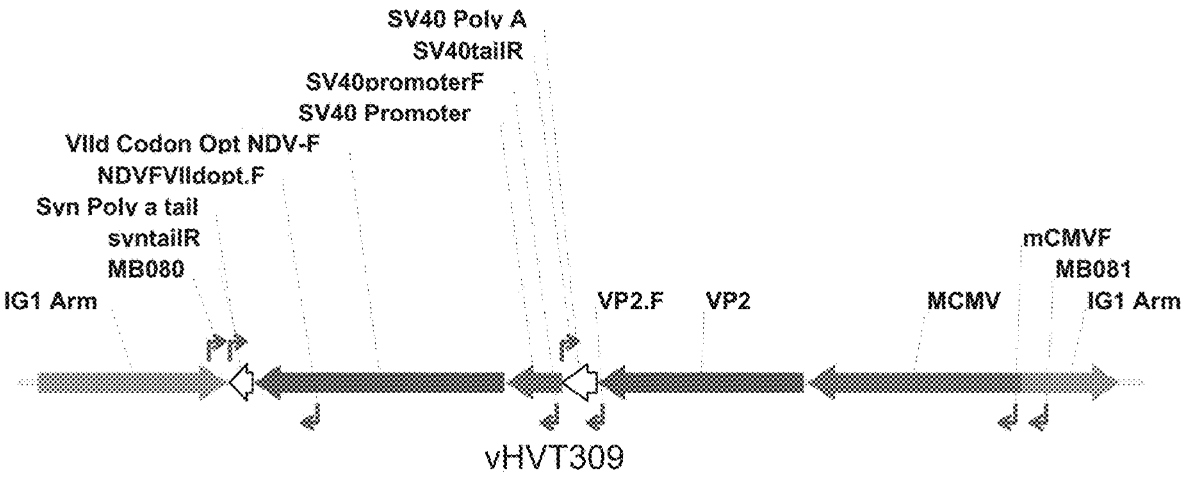
FIG. 4 depicts schematic representation of primer binding sites for vHVT309.

DNA was extracted from a stock virus by phenol/chloroform extraction, ethanol precipitation, and resuspended in 20 mM HEPES. PCR primers (Table 1) were designed to specifically identify the IBDV-VP2 and NDV-F VIId gene, the promoters, the poly As, as well as, the purity of the recombinant virus from Vaxxitek parental virus. The locations of the primer binding sites are shown in FIG. 4. PCR was performed using 200 μg of DNA template along with the specified primer pairs indicted in Table 1. PCR cycling conditions are as follows: 94° C.-2 min; 30 cycles of 94° C.-30 sec, 60° C.-45 sec, 68° C.-3 min (5 min for MB080+MB081 primer set); 68° C.-5 min (7 min for MB080+MB081 primer set).

TABLE 1

Expected PCR bands using specific primer sets

| Primer set | Vaxxitek | vHVT309 |
|---|---|---|
| MB080 + MB081 | 3350 | 5577 |
| MB010 + NDVFVlldopt.F | — | 737 |
| MB080 + VP2.F | 405 | 2632 |
| SV40tailR + mCMVF | 3021 | 3021 |
| syntailR + SV40promoterF | — | 2184 |

Expression Analysis

For immunofluorescence testing, the recombinant material was diluted 1:100 in media. Approximately 50 μl of the diluted virus was added to 20 ml of DMEM+2% FBS with $2\times10^7$ CEFs and then aliquoted onto two 96 well plates (100 μl/well). The plates were incubated for 4 days at 37° C.+5% $CO_2$ until viral plaques were visible. The plates were fixed with 95% ice-cold acetone for three minutes, allowed to air dry for ten minutes and washed three times with water. Dual immunofluorescent staining was performed for plate #1 using chicken anti-sera against Newcastle Disease virus (NDV Pab) (lot #C0117A, Charles Rivers Laboratories) at 1:500 and HVT L78 monoclonal antibody (HVT Mab) (Lee et al. 1983, J. Immunol. 130 (2) 1003-6; Merial batch) at 1:3000 and the plate was incubated at 37° C. for 1 hour. Dual Immunofluorescent was performed for plate #2 using chicken anti-sera against Infectious Bursal Disease virus (IBDV Pab) at 1:500 (lot #G0117, Charles Rivers Laboratories) and HVT L78 monoclonal antibody (HVT Mab) (Merial) at 1:3000 and the plate was incubated at 37° C. for 1 hour. After one hour incubation, the plates were washed three times with PBS. To both plate #1 and #2 FITC labeled anti-chicken IgG (cat #F8888, Sigma) at 1:500 and TRITC labeled Alex Fluor donkey anti-mouse (cat #A10037, Invitrogen) at 1:300 was added. Again the plates were incubated at 37° C. for 1 hour. After one hour incubation the cells were rinsed three times with PBS and visualized with a fluorescent microscope using fluorescein isothiocyanate (FITC) filter and tetramethyl rhodamine iso-thiocyanate (TRITC) filter.

Results

The nucleotide and amino acid sequences of the donor plasmid pFSV40VP2 are assigned SEQ ID NO as shown in FIG. 1.

Recombinant Generation and Expression Analyses

Genomic DNA of vHVT13 virus was co-electroporated with pFSV40VP2 donor plasmid to generate recombinant using homologous recombination technique. Recombinant virus was separated from parental Vaxxitek virus by immunofluorescent positive well selection and PCR screening in multiple rounds of plaque purification. A plaque purified recombinant virus expressing the NDV-F protein, designated vHVT309, was scaled up from tissue culture flasks to $5\times850$ $cm^2$ roller bottles. After about 72 hrs post infection the infected CEFs were harvested. Aliquots were frozen in liquid nitrogen, each aliquot contained 10% FBS and 10% DMSO. Titrations were performed in triplicate on CEFs and a titer of $1.5\times10^5$ pfu/ml was obtained for vHVT309.

Dual immunofluorescent staining was performed using chicken anti-sera (Pab) at 1:500 and HVT L78 monoclonal antibody (Mab) at 1:3000 followed by a FITC labeled anti-chicken IgG at 1:500 and TRITC labeled Alex Fluor donkey anti-mouse at 1:300. Plate #1 compares the expression of Newcastle Disease virus with HVT and plate #2 compares the expression of Infectious Bursal Disease virus with HVT. All examined HVT TRITC positive plaques of vHVT309 were found to express NDV-F and IBDV-VP2 proteins.

PCR Analysis of vHVT309

Figure 5:
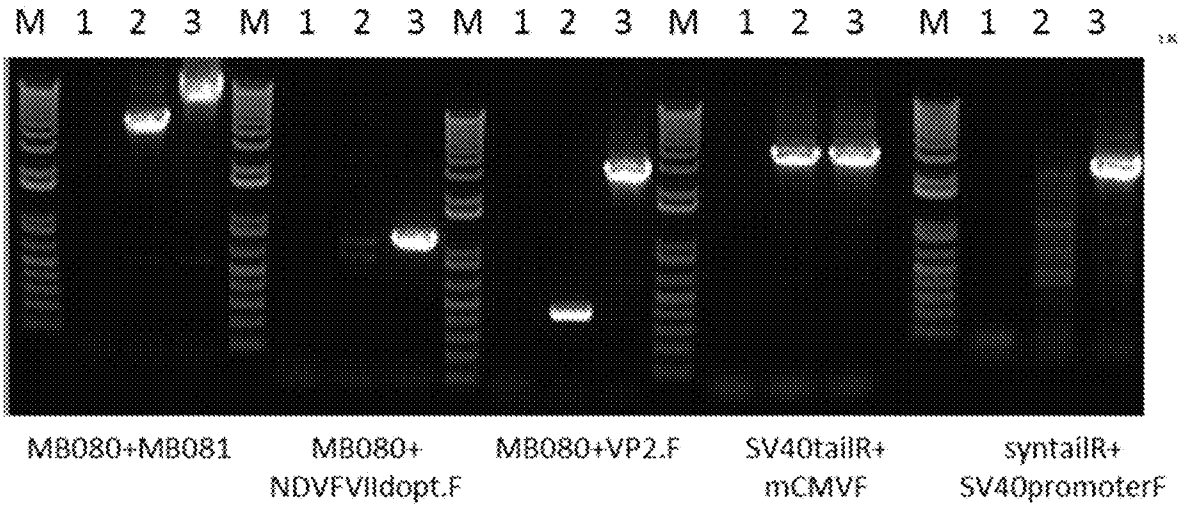
FIG. 5 depicts PCR identity result of vHVT309.

Purity of recombinant virus was verified by PCR using primer pairs that are specific to the HVT flanking arms, the promoters, the NDV-F and IBDV-VP2 genes, and the poly A tails. The PCR results demonstrate that recombinant virus vHVT309 carries the intended expression cassette and the virus stock is free from detectable amounts of parental Vaxxitek virus (Table 1 and FIG. 5).

Conclusion

Based on PCR testing and immunofluorescence analysis, vHVT309 is a recombinant virus containing an IBDV-VP2 gene under the control of mCMV promoter and a NDV-F gene under the control of an SV40 promoter. The newly generated vHVT309 is free of any detectable parental vHVT13 virus.

Example 1.2 Construction of Recombinant vHVT310 Expressing IBDV-VP2 and NDV-F The objective of the study is to construct a recombinant HVT in which an expression cassette containing a mouse cytomegalovirus promoter (mCMV), a gene encoding an infectious bursal disease virus viral protein 2 (VP2), internal ribosome entry site (IRES), a gene encoding a Newcastle Disease virus fusion protein (NDV-F), and Simian virus 40 poly A tail (SV40 poly A) is integrated in the intergenic site 1 (IG1) (FIG. 2).

The parental virus used in the construct is vHVT13. A Newcastle disease virus Fusion Protein (NDV-F) corresponding to genotype VIId sequence was chemically synthesized and codon optimized (GenScript). The F protein cleavage site of this synthetic gene was altered to match a lentogenic F cleavage site sequence and the resultant NDV-F gene sequence has 99% amino acid sequence identity to NDV-F sequence deposited in GenBank (AY337464). Mouse CMV IE promoter was used for IBD-VP2 (in the parental Vaxxitek virus). IRES, an RNA sequence derived from Encephalomyocarditis virus (EMCV), that allows the initiation of translation within an mRNA immediately downstream from where the IRES is located, was inserted at the end of the VP2 gene to initiate translation of a downstream NDV-F gene. This was the first time that IRES was used in an HVT vector.

The insertion locus is intergenic site 1 (IG1) in HVT (FIG. 2). Donor plasmid pFIRESVP2 (an insertion plasmid containing the VP2 gene+IRES+NDV-F and SV40 poly A/flanking arm of IG1) was constructed as described below. Chicken embryo fibroblast cells (CEF) were used for in vitro recombination.

Figure 6:
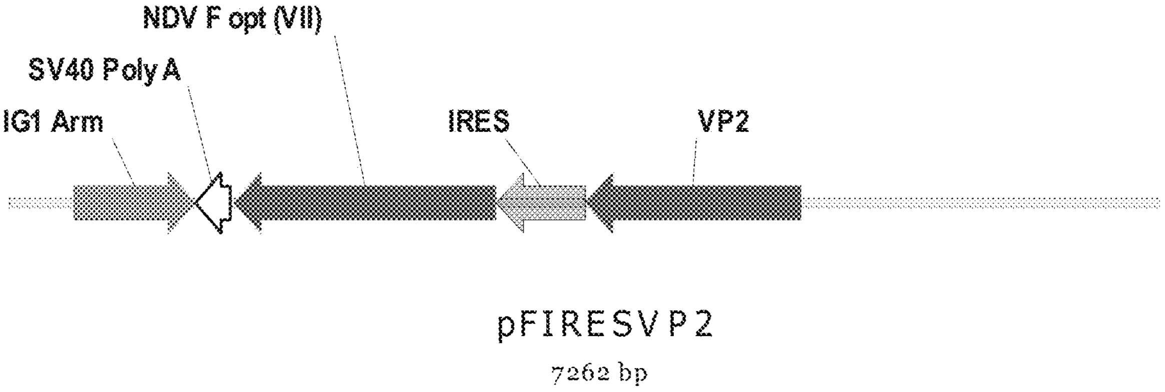
FIG. 6 depicts pFIRESVP2 plasmid map.

Donor Plasmid Construction:

Synthetic DNA in pUC57 containing the IBDV VP2 gene (SEQ ID NO:1 encoding SEQ ID NO:2), IRES (SEQ ID NO:10), NDV-F gene (SEQ ID NO:3 encoding SEQ ID NO:5), and SV40 poly A tail (SEQ ID NO:8) was synthesized by GeneScript (FIG. 6). The plasmid, pFIRESVP2 was transformed using Top10 Oneshot kit (cat #C404002, Invitrogen) and a large scale culture was grown and plasmid extraction was done using Qiagens Maxi Prep kit.

Recombinant Generation

The homologous recombination procedure as described in Example 1.1 was followed to make recombinant vHVT310.

Analysis of Recombinant by PCR

The PCR analysis procedure as described in Example 1.1 was performed to verify vHVT310.

Expression Analysis

The expression analysis described in Example 1.1 was performed to analyze the expression of vHVT310.

Results

The nucleotide and amino acid sequence of the donor plasmid pFIRESVP2 are assigned SEQ ID NO as shown in FIG. 1.

Recombinant Generation and Expression Analyses

Genomic DNA of Vaxxitek virus was co-electroporated with pFIRESVP2 donor plasmid to generate recombinant virus using homologous recombination technique. Recombinant virus was separated from parental vHVT13 virus by immunofluorescent positive well selection and PCR screening in multiple rounds of plaque purification. A plaque purified recombinant virus expressing the NDV-F protein, designated vHVT310, was scaled up from tissue culture flasks to 5×850 $cm^2$ roller bottles. After about 72 hrs post infection the infected CEFs were harvested. Aliquots were frozen in liquid nitrogen, each aliquot contained 10% FBS and 10% DMSO. Titrations were performed in triplicate on CEFs and a titer of 2.0×$10^6$ pfu/ml was obtained for vHVT310.

Dual Immunofluorescent staining was performed using chicken anti-sera (Pab) at 1:500 and HVT L78 monoclonal antibody (Mab) at 1:3000 followed by a FITC labeled anti-chicken IgG at 1:500 and TRITC labeled Alex Fluor donkey anti-mouse at 1:300. Plate #1 compares the expression of Newcastle Disease virus with HVT and plate #2 compares the expression of Infectious Bursal Disease virus with HVT. All examined HVT TRITC positive plaques of vHVT310 were found to express NDV-F and IBDV-VP2 proteins.

PCR Analysis of vHVT310

Figure 7:
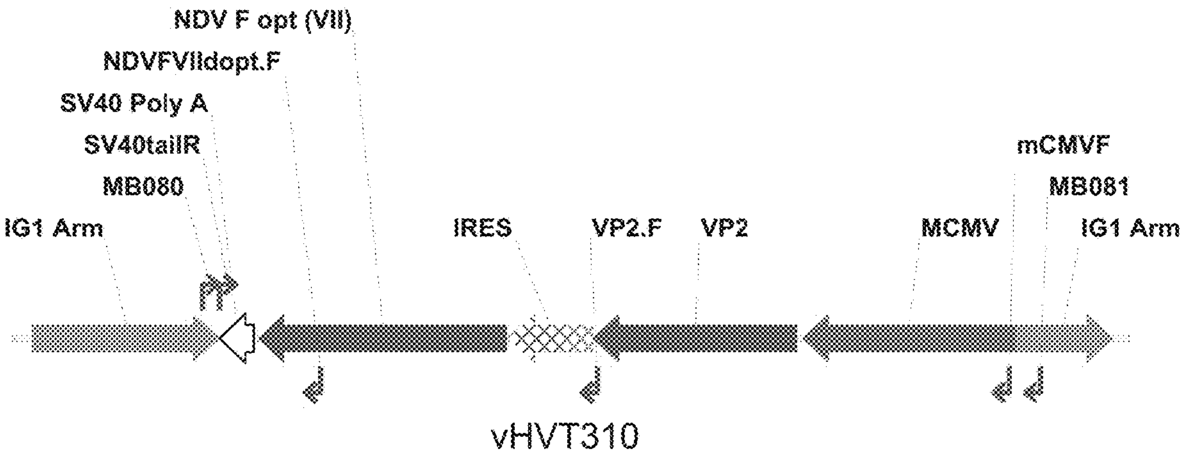
FIG. 7 depicts schematic representation of primer binding sites for vHVT310.
Figure 8:
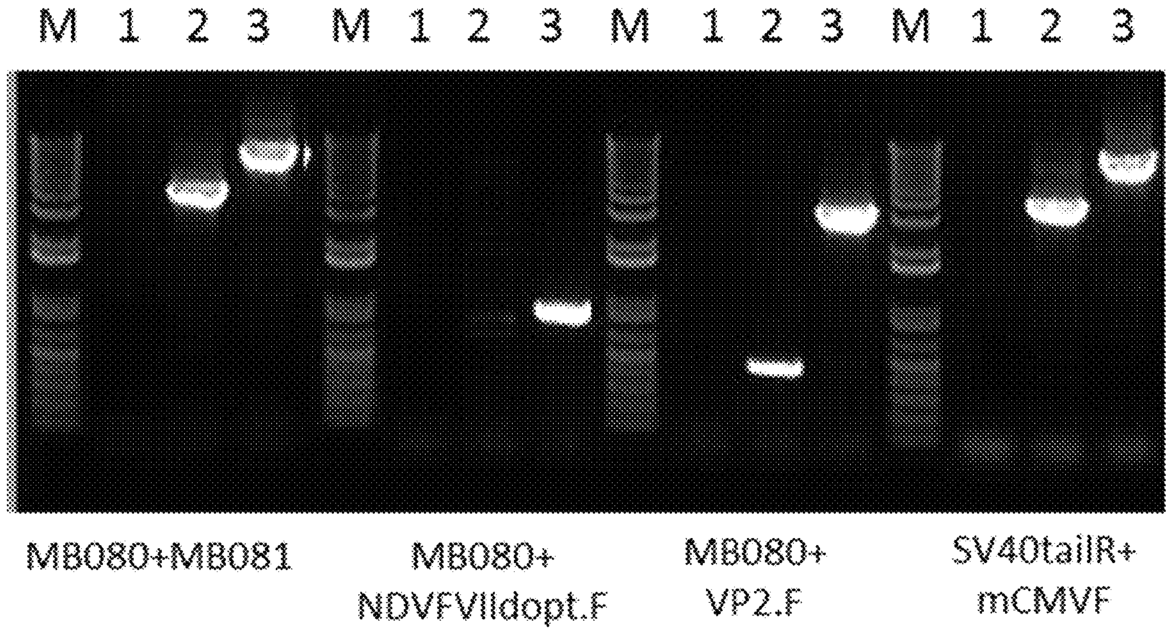
FIG. 8 depicts PCR identity result of vHVT310.

Purity of recombinant virus was verified by PCR using primer pairs that are specific to the HVT flanking arms, the promoter, the NDV-F and IBDV-VP2 genes, and the polyA tail. The PCR results demonstrate that recombinant virus vHVT310 carries the intended expression cassette and the virus stock is free from detectable amounts of parental Vaxxitek virus (Table 2 and FIG. 7-8).

TABLE 2

Expected PCR bands using specific primer sets

| Primer set | Vaxxitek | vHVT310 |
|---|---|---|
| MB080 + MB081 | 3350 | 5586 |
| MB080 + NDVFVIIdopt.F | — | 798 |
| MB080 + VP2.F | 405 | 2641 |
| SV40tailR + mCMVF | 3021 | 5257 |

Conclusion

Based on PCR testing and immunofluorescence analysis, vHVT310 is a recombinant virus containing an IBDV-VP2 and NDV-F gene under the control of mCMV promoter, where the translation of NDV-F gene is initiated by IRES from EMCV. The newly generated recombinant vHVT310 is free of any detectable parental vHVT13 virus.

Example 1.3 Construction of Recombinant vHVT311 Expressing IBDV-VP2 and NDV-F

The objective of the study is to construct a recombinant HVT in which an expression cassette containing a mouse cytomegalovirus promoter (mCMV), a gene encoding an infectious bursal disease virus viral protein 2 (VP2), self-cleaving porcine teschovirus-1 2A peptide (P2A), a gene encoding a Newcastle Disease virus fusion protein (NDV-F), and Simian virus 40 poly A tail (SV40 poly A) is integrated in the intergenic site 1 (IG1) (FIG. 2).

The parental virus used in the construct is vHVT13 (an HVT vector expressing the IBDV VP2 gene, Merial's VAXXITEK® (HVT+IBD) Vaccine). The polynucleotide corresponding to wild-type genotype VIId Newcastle disease virus Fusion Protein (NDV-F) sequence was chemically synthesized (GenScript). The F protein cleavage site of this synthetic gene was altered to match a lentogenic F cleavage site sequence and the resultant NDV-F gene sequence has 99% amino acid sequence identity to NDV-F sequence deposited in GenBank (AY337464). Mouse CMV IE promoter was used for IBD-VP2 (in the parental Vaxxitek virus). A self-cleaving porcine teschovirus-1 2A peptide (P2A) that allows co-translational 'cleavage' of the upstream and downstream genes, VP2 and F, respectively from a single promoter mCMV, was inserted at the end of the VP2 gene. This is the first time that P2A was used in HVT vectors.

The insertion locus is intergenic site 1 (IG1) in HVT (FIG. 2). Donor plasmid pFP2AVP2 (an insertion plasmid containing the VP2+P2A+NDV-F and SV40 poly A/flanking arm of IG1) was constructed as described below. Chicken embryo fibroblast cells (CEF) were used for in vitro recombination.

Donor Plasmid Construction

Figure 9:
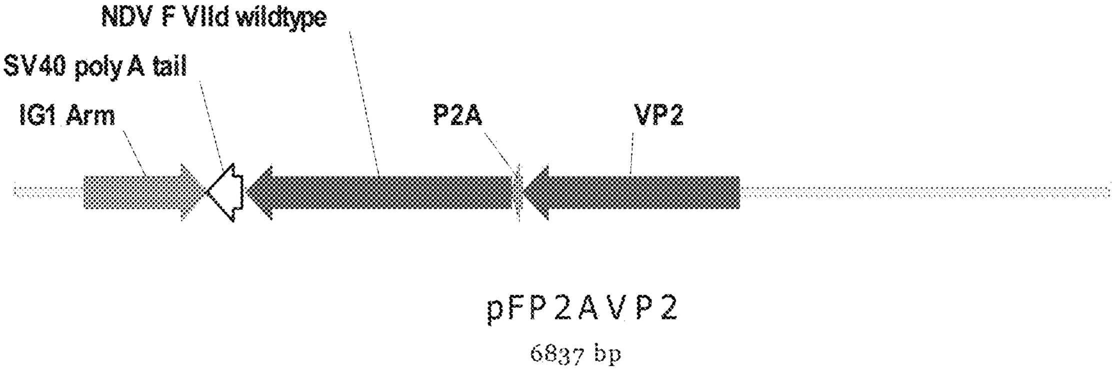
FIG. 9 depicts pFP2AVP2 plasmid map.

Synthetic DNA in pUC57 containing the IBDV VP2 gene (SEQ ID NO:1 encoding SEQ ID NO:2), P2A encoding DNA (SEQ ID NO:11), NDV-F gene (SEQ ID NO:4 encoding SEQ ID NO:5), and SV40 poly A tail (SEQ ID NO:8) was synthesized by GeneScript (FIG. 9). The plasmid, pFP2AVP2 was transformed using Top10 Oneshot kit (cat #C404002, Invitrogen) and a large scale culture was grown and plasmid extraction was done using Qiagens Maxi Prep kit.

Recombinant Generation

The homologous recombination procedure as described in Example 1.1 was followed to make recombinant vHVT311.

Analysis of Recombinant by PCR

The PCR analysis procedure as described in Example 1.1 was performed to verify vHVT311.

Expression Analysis

The expression analysis described in Example 1.1 was performed to analyze the expression of vHVT311.

Results

The nucleotide and amino acid sequences of the donor plasmid pFP2AVP2 are assigned SEQ ID NO as shown in FIG. 1.

Recombinant Generation and Expression Analyses

Genomic DNA of Vaxxitek virus was co-electroporated with pFP2AVP2 donor plasmid to generate recombinant virus using homologous recombination technique. Recombinant virus was separated from parental Vaxxitek virus by immunofluorescent positive well selection and PCR screening in multiple rounds of plaque purification. A plaque purified recombinant virus expressing the NDV-F protein, designated vHVT311, was scaled up from tissue culture flasks to 5×850 $cm^2$ roller bottles. After about 72 hrs post infection the infected CEFs were harvested. Aliquots were frozen in liquid nitrogen, each aliquot contained 10% FBS and 10% DMSO. Titrations were performed in triplicate on CEFs and a titer of 2.5×$10^6$ pfu/ml was obtained for vHVT311.

Dual Immunofluorescents was performed using chicken anti-sera (Pab) at 1:500 and a monoclonal antibody (Mab) at 1:3000 followed by a FITC labeled anti-chicken IgG at 1:500 and TRITC labeled Alex Fluor donkey anti-mouse at 1:300. Plate #1 compares the expression of Newcastle Disease virus with HVT and plate #2 compares the expression of Infectious Bursal Disease virus with Newcastle Disease virus. All examined HVT TRITC positive plaques of vHVT311 were found to express NDV-F and all NDV TRITC positive plaques were found to express IBDV-VP2 proteins.

PCR Analysis of vHVT311

Figure 10:
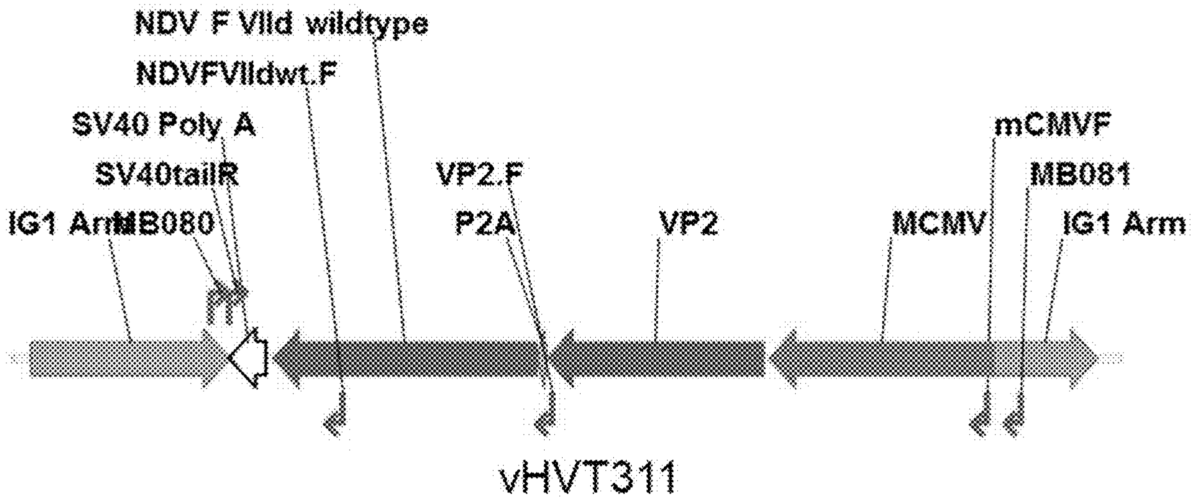
FIG. 10 depicts schematic representation of primer binding sites for vHVT311.
Figure 11:
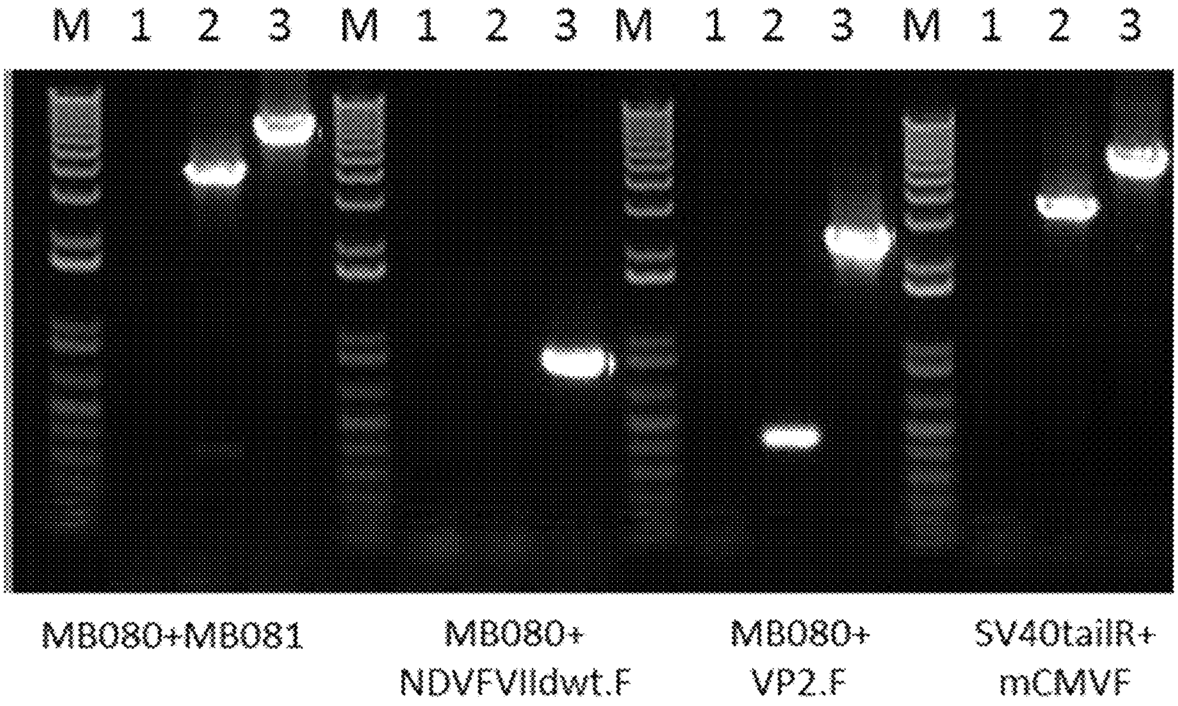
FIG. 11 depicts PCR identity result of vHVT311.

Purity of recombinant virus was verified by PCR using primer pairs that are specific to the HVT flanking arms, the promoter, the NDV-F and IBDV-VP2 genes, and the poly A tail. The PCR results demonstrate that recombinant virus vHVT311 carries the intended expression cassette and the virus stock is free from detectable amounts of parental Vaxxitek virus (Table 3 and FIG. 10-11).

TABLE 3

| Expected PCR bands using specific primer sets | | |
|---|---|---|
| Primer set | Vaxxitek | vHVT311 |
| MB080 + MB081 | 3350 | 5101 |
| MB080 + NDVFVIIdwt.F | — | 840 |
| MB080 + VP2.F | 405 | 2156 |
| SV40tailR + mCMVF | 3021 | 4772 |

Conclusion

Based on PCR testing and immunofluorescence analysis, vHVT311 is a recombinant virus containing an IBDV-VP2 and NDV-F gene under the control of mCMV promoter in which the 2A peptide-mediated cleavage result in co-expression of VP2 and F proteins. The newly generated recombinant vHVT311 is free of any detectable parental vHVT13 virus.

Example 1.4 Construction of Recombinant vHVT317 Expressing IBDV-VP2 and ILTV-gD The objective of the study is to construct a recombinant HVT in which an expression cassette containing a mouse cytomegalovirus promoter (mCMV), a gene encoding an infectious bursal disease virus viral protein 2 (VP2), internal ribosome entry site (IRES), a gene encoding an Infectious Laryngotracheitis glycoprotein D protein (ILTV-gD), and Simian virus 40 poly A tail (SV40 poly A) is integrated in the intergenic site 1 (IG1) (FIG. 2).

The parental virus used in the construct is vHVT13. An Infectious Laryngotracheitis virus glycoprotein D (ILTV gD) sequence which was chemically synthesized (GenScript) was used in the construct. Mouse CMV IE promoter was used for IBD-VP2 (in the parental vHVT13 virus). An RNA sequence (IRES) derived from Encephalomyocarditis virus (EMCV), that allows the initiation of translation within an mRNA immediately downstream from where the IRES is located, was inserted at the end of the VP2 gene to initiate translation of a downstream ILTV-gD gene.

The insertion locus is intergenic site 1 (IG1) in HVT (FIG. 2). Donor plasmid pVP2IRESgD (an insertion plasmid containing the VP2 gene+IRES+ILTV-gD and SV40 poly A/flanking arm of IG1) was constructed as described below. Chicken embryo fibroblast cells (CEF) were used for in vitro recombination.

Donor Plasmid Construction

Figure 12:
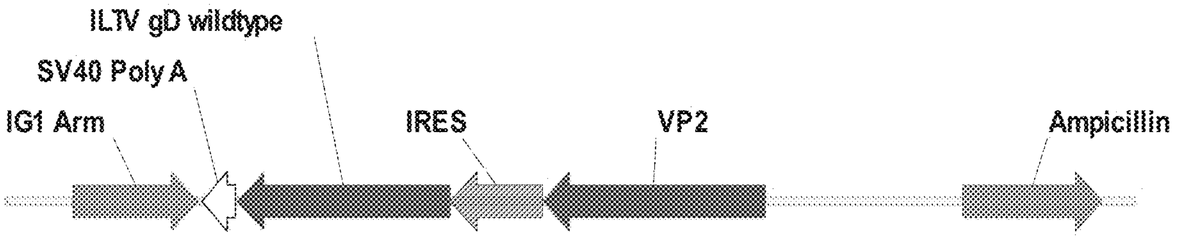
FIG. 12 depicts pVP2IRESgD plasmid map.

Synthetic DNA in pUC57 containing the IBDV VP2 gene (SEQ ID NO:1 encoding SEQ ID NO:2), IRES (SEQ ID NO:10), ILTV-gD gene (SEQ ID NO:16 encoding SEQ ID NO:17), and SV40 poly A tail (SEQ ID NO:8) was synthesized by GenScript. The plasmid, pFIRESVP2 was transformed into dcm-/dam-competent cells (New England Biolabs, cat #C2925I) then digested with HindIII/SalI. The 5 kb fragment was gel extracted. A synthetic DNA in pUC57 containing a partial IRES, ILTV-gD wildtype, and SV40 poly A tail was synthesized by GenScript. The plasmid, Sal-Fse gD-IRES was digested with HindIII/SalI. The 1.9 kb fragment was gel extracted. The two fragments were ligated and transformed using Top10 Oneshot kit (cat #C404002, Invitrogen). Colonies were screen by HindIII/SalI for the correct pattern. The final donor plasmid was sequenced verified and designated pVP2IRESgD (see FIG. 12).

Recombinant Generation

The homologous recombination procedure as described in Example 1.1 was followed to make recombinant vHVT317.

Analysis of Recombinant by PCR

The PCR analysis procedure as described in Example 1.1 was performed to verify vHVT317.

Expression Analysis

The expression analysis described in Example 1.1 was performed to analyze the expression of vHVT317.

Results

The nucleotide and amino acid sequence of the donor plasmid pVP2IRESgD are assigned SEQ ID NO as shown in FIG. 1.

Recombinant Generation and Expression Analyses

Dual Immunofluorescents was performed using chicken anti-sera (Polyclonal antibody) at 1:500 and a monoclonal antibody (Mab) at 1:3000 followed by a FITC labeled anti-chicken IgG at 1:500 and TRITC labeled Alex Fluor donkey anti-mouse at 1:300. All examined plaques of vHVT317 were found to express IBDV-VP2 proteins compared to HVT positive plaques and all and plaques were found to express ILTV-gD proteins when compared to IBDV positive plaques.

PCR Analysis of vHVT317

Figure 13:
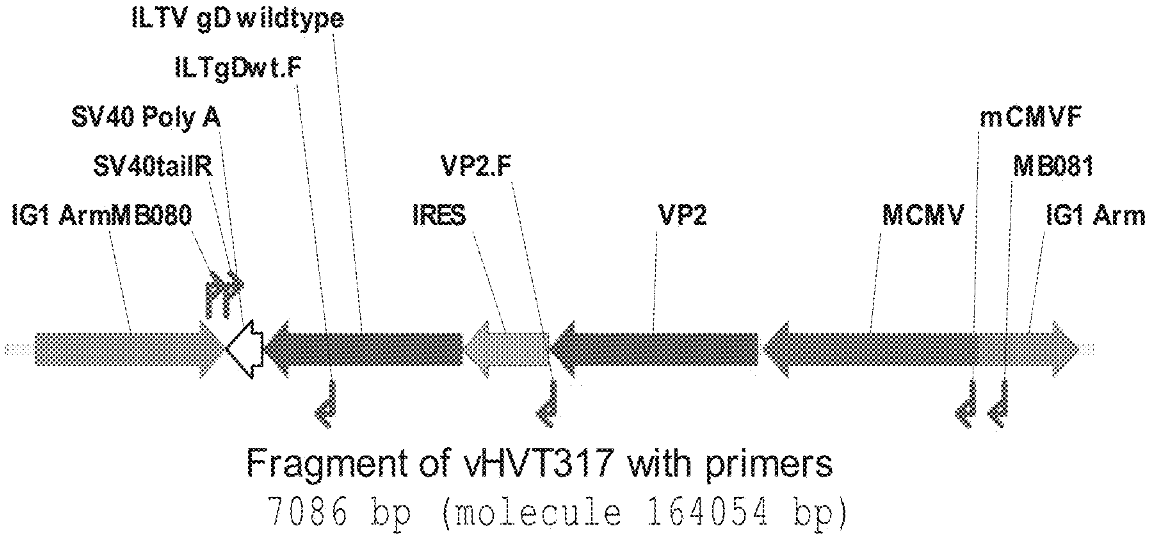
FIG. 13 depicts schematic representation of primer binding sites for vHVT317.
Figure 14:
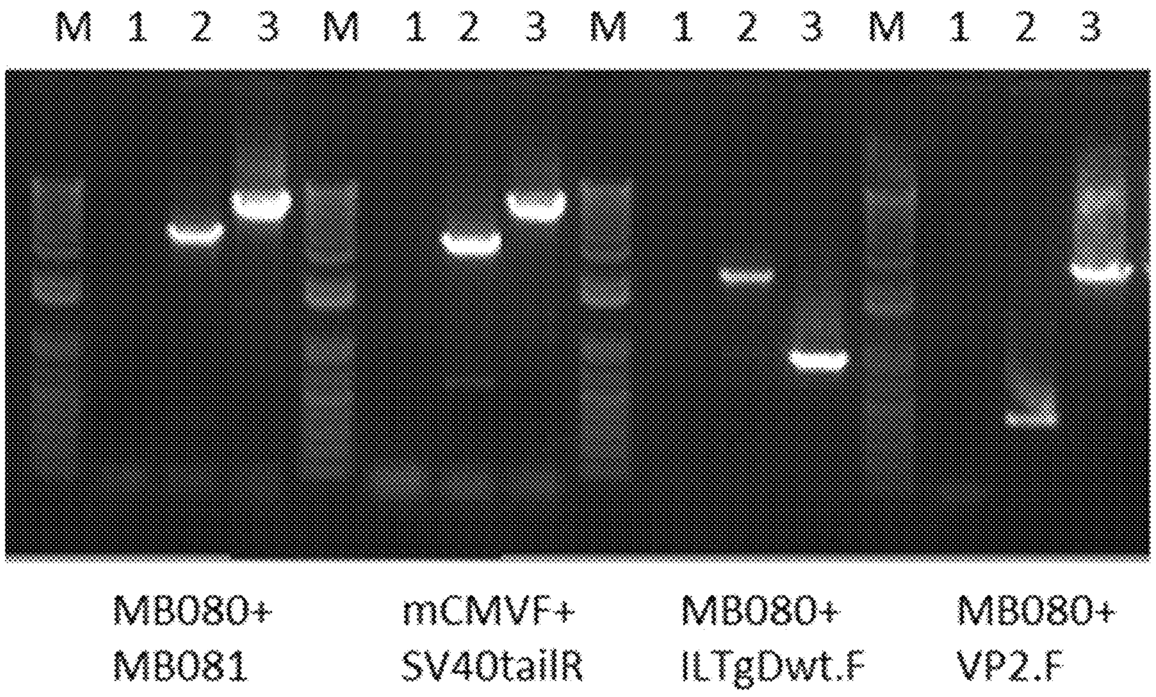
FIG. 14 depicts PCR identity result of vHVT317.

Purity of recombinant virus was verified by PCR using primer pairs that are specific to the HVT flanking arms, the promoter, the ILTV-gD and IBDV-VP2 genes, and the poly A tail. The PCR results demonstrate that recombinant virus vHVT317 carries the intended expression cassette and the virus stock is free from detectable amounts of parental Vaxxitek virus (Table 4 and FIG. 13-14).

TABLE 4

| Expected PCR bands using specific primer sets | | |
|---|---|---|
| Primer set | Vaxxitek | vHVT317 |
| MB080 + MB081 | 3350 | 5101 |
| MB080 + ILTgDwt.F | — | 825 |
| MB080 + VP2.F | 405 | 2272 |
| SV40tailR + mCMVF | 3021 | 4888 |

Conclusion

Based on PCR testing and immunofluorescence analysis, vHVT317 is a recombinant virus containing an IBDV-VP2 and ILTV-gD gene under the control of mCMV promoter, where the translation of ILTV-gD gene is initiated by IRES from EMCV. The newly generated recombinant vHVT317 is free of any detectable parental vHVT13 virus.

Example 1.5 Construction of Recombinant vHVT313 Expressing IBDV-VP2 and NDV-F The objective of the study is to construct a recombinant HVT in which an expression cassette containing a mouse cytomegalovirus promoter (mCMV), a gene encoding an infectious bursal disease virus viral protein 2 (VP2), Simian virus 40 poly A tail (SV40 poly A), Simian virus 40 promoter (SV40 promoter), a gene encoding a wildtype Newcastle disease virus fusion protein (NDV-F) and synthetic poly A tail (syn poly A tail) is integrated in the intergenic site 1 (IG1) (FIG. 2).

The parental virus used in the construct is vHVT13. A Newcastle disease virus Fusion Protein (NDV-F) corresponding to genotype VIId wildtype sequence chemically synthesized (GenScript). The F protein cleavage site of this synthetic gene was altered to match a lentogenic F cleavage site sequence and the resultant NDV-F gene sequence has 99% amino acid sequence identity to NDV-F sequence deposited in GenBank (AY337464). Mouse CMV IE promoter for IBD-VP2 (in the parental Vaxxitek virus) and SV40 promoter for NDV-F were used.

The insertion locus is intergenic site 1 (IG1) (FIG. 2). Donor plasmid pFwtSV40VP2 (an insertion plasmid containing the VP2/SV40 poly A and flanking arm of IG1+SV40 promoter+NDV-F+synthetic poly A) was constructed as described below. Chicken embryo fibroblast cells (CEF) were used for in vitro recombination.

Donor Plasmid Construction

Synthetic DNA in pUC57 containing the IBDV VP2 gene (SEQ ID NO:1 encoding SEQ ID NO:2), SV40 poly A tail (SEQ ID NO:8), SV40 promoter (SEQ ID NO:7), NDV-F gene (SEQ ID NO:4 encoding SEQ ID NO:5), and synthetic poly A tail (SEQ ID NO:9) was synthesized by GeneScript.

Figure 15:
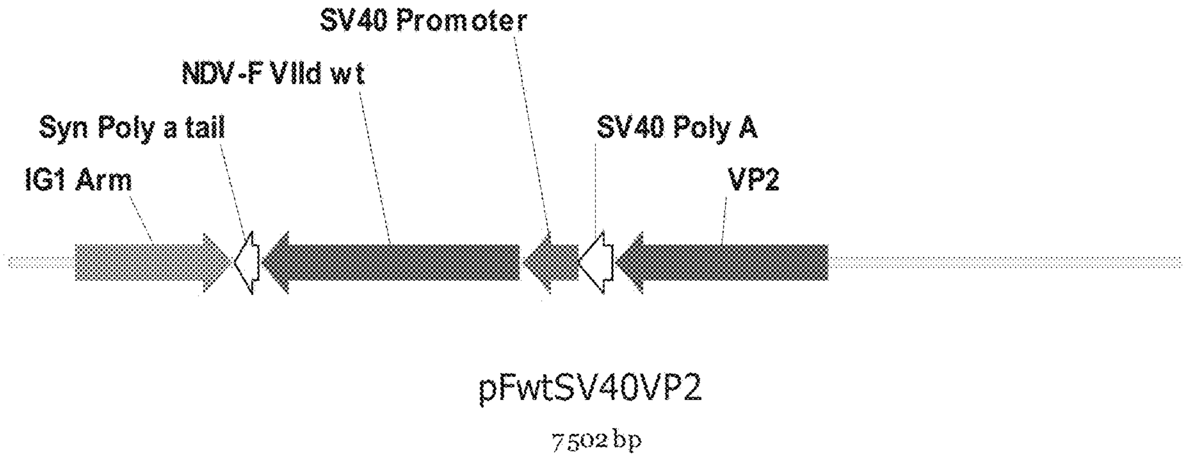
FIG. 15 depicts pFwtSV40VP2 plasmid map.

The plasmid, pFSV40VP2 was then digested with SbfI/AvrII and the 5.6 kb fragment was gel extracted. A plasmid, pHM103NDVFwtsyn was also digested with SbfI/AvrII and the 1.9 kb fragment was gel extracted. The fragments were then ligated together and transformed using Top10 Oneshot kit (cat #C404002, Invitrogen). Colonies were screened with PstI for the correct pattern. Transient expression of the maxi prep was verified using Fugene Transfection Reagent in Chicken Embryo Fibroblast Cells (CEF's) and chicken polyclonal sera against NDV. The final donor plasmid was sequenced verified and designated pFwtSV40VP2 (see FIG. 15).

Recombinant Generation

The homologous recombination procedure as described in Example 1.1 was followed to make recombinant vHVT313.

Analysis of Recombinant by PCR

The PCR analysis procedure as described in Example 1.1 was performed to verify vHVT313.

Expression Analysis

The expression analysis described in Example 1.1 was performed to analyze the expression of vHVT313.

Results

The nucleotide and amino acid sequence of the donor plasmid pFwtSV40VP2 are assigned SEQ ID NO as shown in FIG. 1.

Recombinant Generation and Expression Analyses

Dual Immunofluorescents was performed using chicken anti-sera (Pab) and an anti-HVT monoclonal antibody (Mab) followed by a FITC labeled anti-chicken IgG and TRITC labeled Alex Fluor donkey anti-mouse. All examined TRITC positive plaques of vHVT313 were found to express NDV-F and IBDV-VP2 proteins.

PCR Analysis of vHVT313

Figure 16:
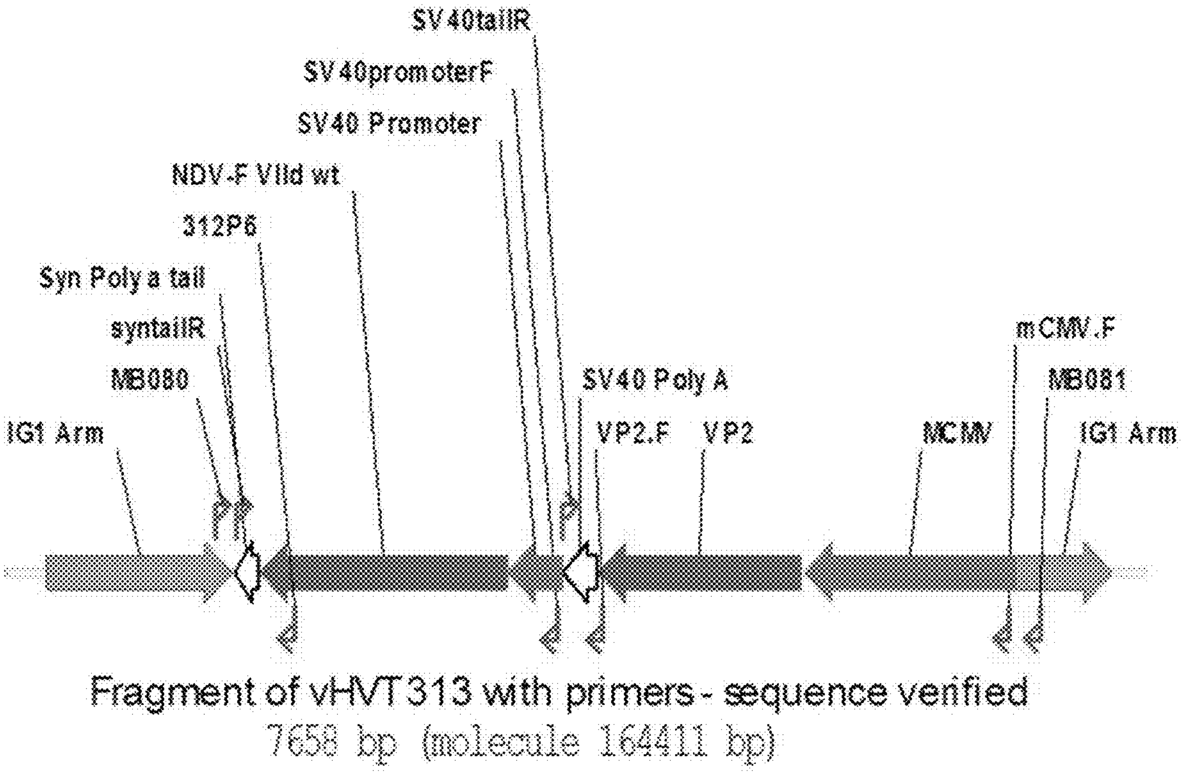
FIG. 16 depicts schematic representation of primer binding sites for vHVT313.
Figure 17:
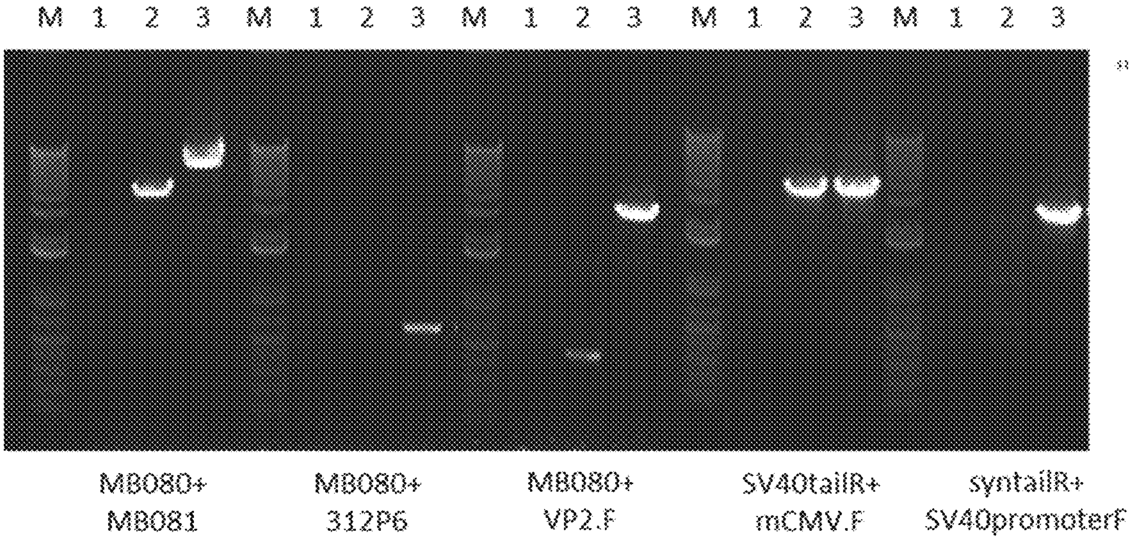
FIG. 17 depicts PCR identity result of vHVT313.

Purity of recombinant virus was verified by PCR using primer pairs that are specific to the HVT flanking arms, the promoters, the NDV-F and IBDV-VP2 genes, and the poly A tails. The PCR results demonstrate that recombinant virus vHVT313 carries the intended expression cassette and the virus stock is free from detectable amounts of parental Vaxxitek virus (Table 5 and FIG. 16-17).

TABLE 5

Expected PCR bands using specific primer sets

| Primer set | Vaxxitek | vHVT313 |
|---|---|---|
| MB080 + MB081 | 3350 | 5574 |
| MB080 + 312P6 | — | 556 |
| MB080 + VP2.F | 405 | 2629 |
| SV40tailR + mCMVF | 3021 | 3021 |
| SyntailR + SV40promoterF | — | 2181 |

Conclusion

Based on PCR testing and immunofluorescence analysis, vHVT313 is a recombinant virus containing an IBDV-VP2 gene under the control of mCMV promoter and a NDV-F wildtype gene under the control of an SV40 promoter. The newly generated vHVT313 is free of any detectable parental Vaxxitek virus.

Example 1.6 Construction of Recombinant vHVT316 Expressing IBDV-VP2 and NDV-F

The objective of the study is to construct a recombinant HVT in which an expression cassette containing a mouse cytomegalovirus promoter (mCMV), a gene encoding an infectious bursal disease virus viral protein 2 (VP2), internal ribosome entry site (IRES), a gene encoding a wildtype Newcastle Disease virus fusion protein (NDV-F), and Simian virus 40 poly A tail (SV40 poly A) is integrated in the IG1 locus (FIG. 2).

The parental virus used in the construct is vHVT13. A Newcastle disease virus Fusion Protein (NDV-F) corresponding to genotype VIId wildtype sequence chemically synthesized (GenScript). The F protein cleavage site of this synthetic gene was altered to match a lentogenic F cleavage site sequence and the resultant NDV-F gene sequence has 99% amino acid sequence identity to NDV-F sequence deposited in GenBank (AY337464). Mouse CMV IE promoter was used for IBD-VP2 (in the parental Vaxxitek virus). IRES was inserted at the end of the VP2 gene to initiate translation of a downstream NDV-F gene.

The insertion locus is IG1 (FIG. 2). Donor plasmid pVP2IRESFwt (an insertion plasmid containing the VP2 gene+IRES+NDV-F and SV40 poly A/flanking arm of IG1) was constructed as described below. Chicken embryo fibroblast cells (CEF) were used for in vitro recombination.

Donor Plasmid Construction

Figure 18:
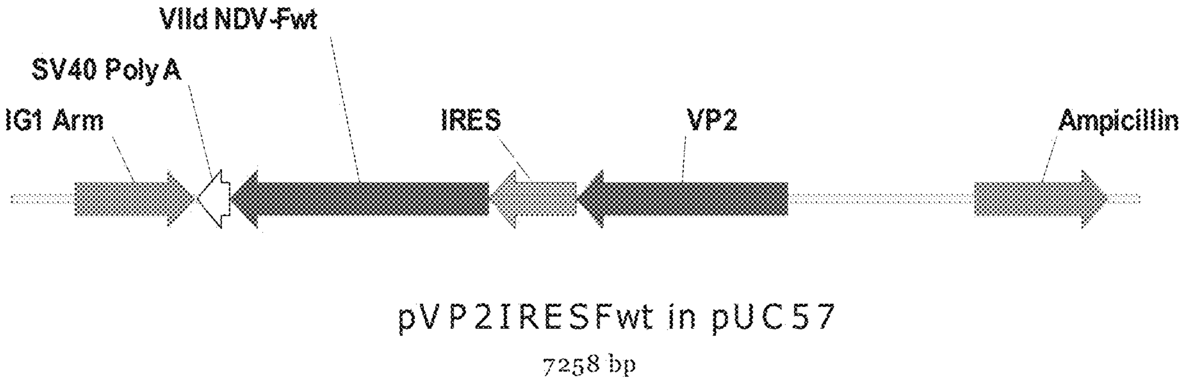
FIG. 18 depicts pVP2IRESFwt plasmid map.

Synthetic DNA in pUC57 containing the IBDV VP2 gene (SEQ ID NO:1 encoding SEQ ID NO:2), IRES(SEQ ID NO:10), NDV-F gene (SEQ ID NO:4 encoding SEQ ID NO:5), and SV40 poly A tail (SEQ ID NO:8), was synthesized by GenScript. The plasmid, pFIRESVP2 was transformed into dcm-/dam-competent cells (New England Biolabs, cat #C2925I) then digested with HindIII/SalI. The 5 kb fragment was gel extracted. A synthetic DNA in pUC57 containing a partial IRES, NDV-F wildtype, and SV40 poly A tail was synthesized by GenScript. The plasmid, Sal-Hind-Fwt+ was digested with HindIII/SalI. The 2.2 kb fragment was gel extracted. The two fragments were ligated and transformed using Top10 Oneshot kit (cat #C404002, Invitrogen). The final donor plasmid was sequenced verified and designated pVP2IRESFwt (see FIG. 18).

Recombinant Generation

The homologous recombination procedure as described in Example 1.1 was followed to make recombinant vHVT316.

Analysis of Recombinant by PCR

The PCR analysis procedure as described in Example 1.1 was performed to verify vHVT316.

Expression Analysis

The expression analysis described in Example 1.1 was performed to analyze the expression of vHVT316.

Results

The nucleotide and amino acid sequence of the donor plasmid pVP2IRESFwt are assigned SEQ ID NO as shown in FIG. 1.

Recombinant Generation and Expression Analyses

Dual Immunofluorescent staining was performed using chicken anti-sera (Pab) and a monoclonal antibody (Mab) followed by a FITC labeled anti-chicken IgG and TRITC labeled Alex Fluor donkey anti-mouse. All examined plaques of vHVT316 were found to express IBDV-VP2 proteins compared to HVT positive plaques and all and plaques were found to express IBDV-VP2 proteins when compared to NDV positive plaques.

PCR Analysis of vHVT316

Figure 19:
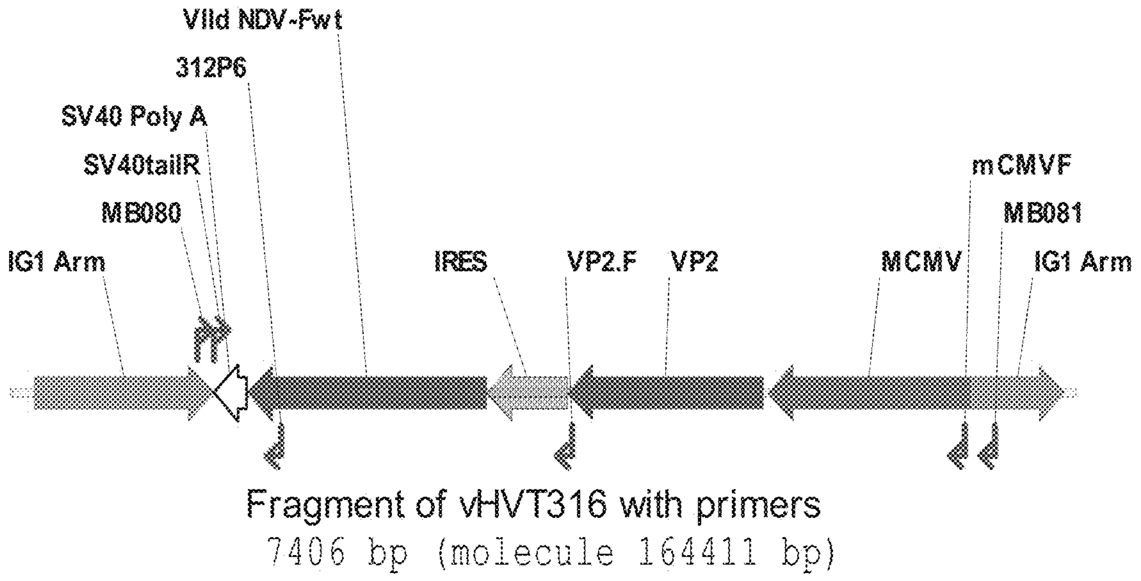
FIG. 19 depicts schematic representation of primer binding sites for vHVT316.
Figure 20:
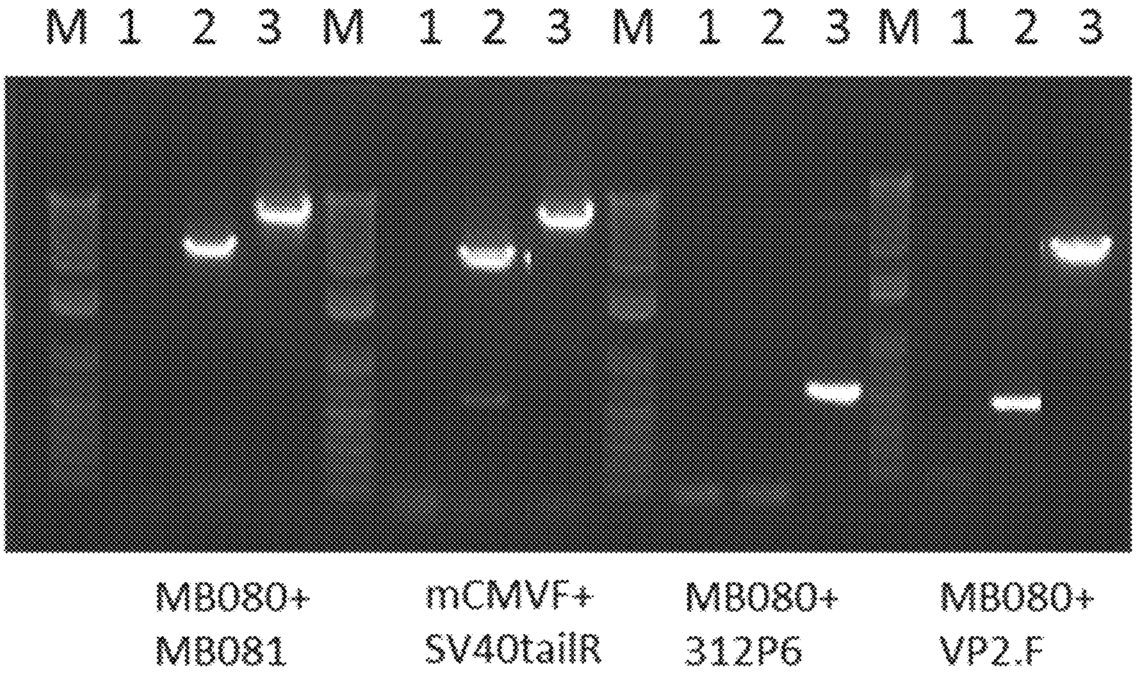
FIG. 20 depicts PCR identity result of vHVT316.

Purity of recombinant virus was verified by PCR using primer pairs that are specific to the HVT flanking arms, the promoter, the NDV-F and IBDV-VP2 genes, and the poly A tail. The PCR results demonstrate that recombinant virus vHVT316 carries the intended expression cassette and the virus stock is free from detectable amounts of parental Vaxxitek virus (Table 6 and FIG. 19-20).

TABLE 6

Expected PCR bands using specific primer sets

| Primer set | Vaxxitek | vHVT316 |
|---|---|---|
| MB080 + MB081 | 3350 | 5574 |
| MB080 + 312P6 | — | 604 |
| MB080 + VP2.F | 405 | 2629 |
| SV40tailR + mCMVF | 3021 | 5245 |

Conclusion

Based on PCR testing and immunofluorescence analysis, vHVT316 is a recombinant virus containing an IBDV-VP2 and NDV-F gene under the control of mCMV promoter, where the translation of NDV-F gene is initiated by IRES from EMCV. The newly generated recombinant vHVT316 is free of any detectable parental Vaxxitek virus.

Example 1.7 Construction of Recombinant vHVT407 Expressing IBDV-VP2 and ILTV-gD The objective of the study is to construct a recombinant HVT in which an expression cassette containing an SV40 promoter, ILTV glycoprotein D, and synthetic poly A into the SORF3-US2 site of vHVT13.

Figure 22:
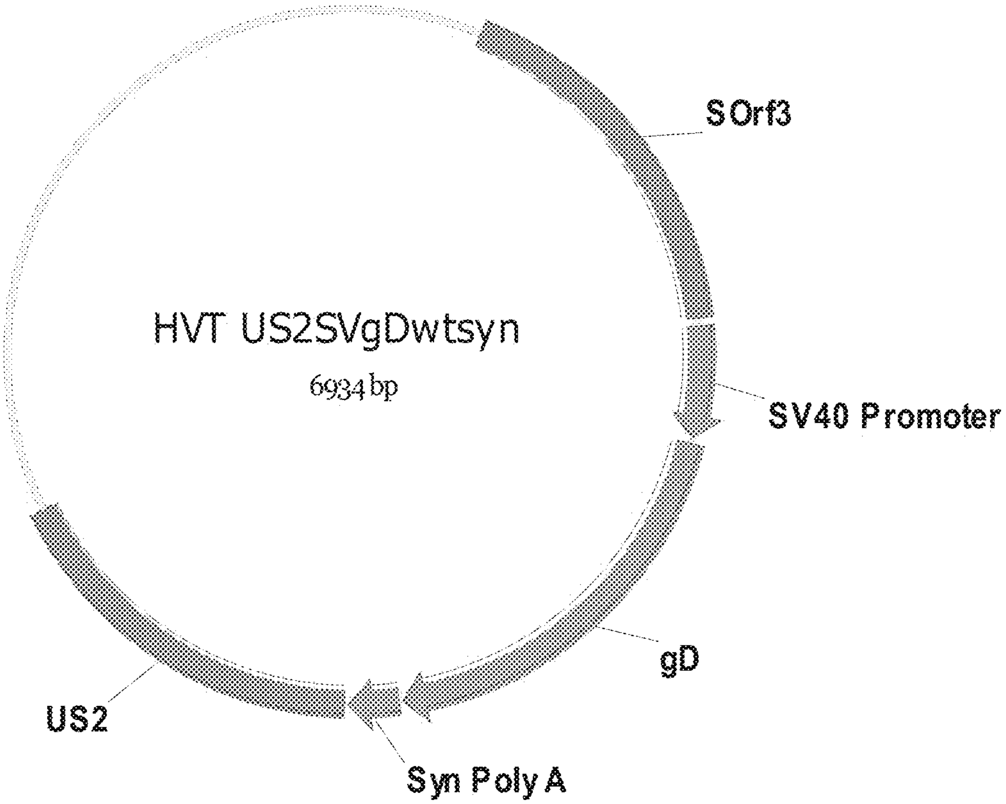
FIG. 22 depicts HVT US2SVgDwtsyn plasmid map.

The parental virus used in the construct is vHVT13. An Infectious Laryngotracheitis virus glycoprotein D (ILTV gD) sequence which was chemically synthesized (GenScript) was used in the construct. SV40 promoter was used for ILTV gD. The insertion locus is SORF3-US2 for ILTV gD and IG1 for IBDV VP2 from vVHT13 (FIG. 2). Donor plasmid HVT US2SVgDwtsyn containing SORF3-US2 arms, SV40 promoter (SEQ ID NO:7), gene encoding ILTV wild-type gD (SEQ ID NO:16 encoding SEQ ID NO:17), and synthetic polyA (SEQ ID NO:9) was constructed (see FIG. 22). Chicken embryo fibroblast cells (CEF) were used for in vitro recombination.

Recombinant Generation

The homologous recombination procedure as described in Example 1.1 was followed to make recombinant vHVT407.

Analysis of Recombinant by PCR

The PCR analysis procedure as described in Example 1.1 was performed to verify vHVT407.

Expression Analysis

The expression analysis described in Example 1.1 was performed to analyze the expression of vHVT407.

Results

The nucleotide and amino acid sequence of the donor plasmid HVT US2SVgDwtsyn are assigned SEQ ID NO as shown in FIG. 1.

Recombinant Generation and Expression Analyses

Dual Immunofluorescent staining was performed using chicken anti-sera (Pab) and a monoclonal antibody (Mab) followed by a FITC labeled anti-chicken IgG and TRITC labeled Alex Fluor donkey anti-mouse. All examined plaques of vHVT407 were found to express IBDV-VP2 and ILTV gD proteins.

PCR Analysis of vHVT407

Purity of recombinant virus was verified by PCR using primer pairs that are specific to the HVT flanking arms, the promoter, the ILTV gD and IBDV-VP2 genes, and the poly A tail. The PCR results demonstrate that recombinant virus vHVT407 carries the intended expression cassette and the virus stock is free from detectable amounts of parental vHVT13 virus.

Conclusion

Based on PCR testing and immunofluorescence analysis, vHVT407 is a recombinant virus containing IBDV-VP2 and ILTV gD genes. The newly generated recombinant vHVT407 is free of any detectable parental vHVT13 virus.

Example 1.8 Construction of Recombinant vHVT308 Expressing NDV-F and ILTV-gD in Opposite Directions The objective of the study is to construct an insertion plasmid for the Intergenic region I site that will contain a Synthetic poly A tail, NDV F, SV40 promoter, HHV3gB promoter, ILTV gD, and SV40 poly A tail for homologous recombination into HVT FC126.

Figure 23:
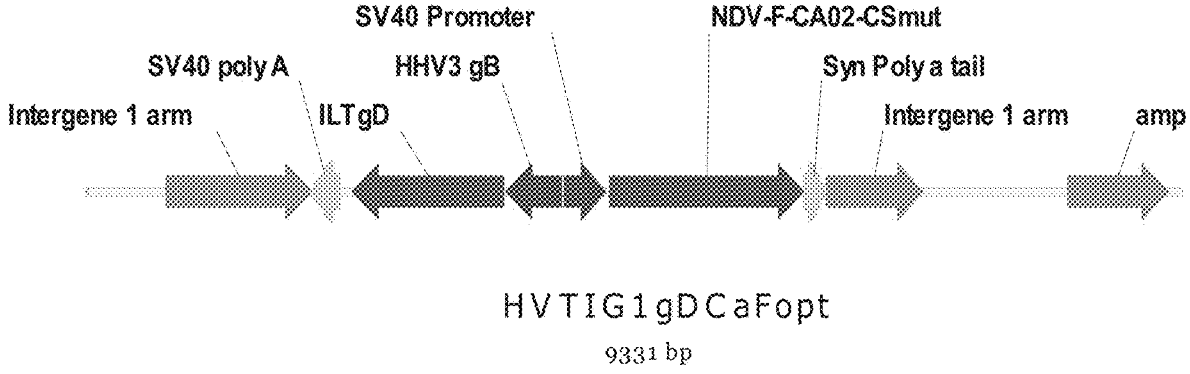
FIG. 23 depicts pHVTIG1gDCaFopt plasmid map.

The parental virus used in the construct is HVT FC126. A synthetic Newcastle disease virus Fusion Protein (NDV-F) (SEQ ID NO:21 encoding SEQ ID NO:22) corresponding to genotype V sequence was chemically synthesized and codon optimized (GenScript). The F protein cleavage site of this synthetic gene was altered to match a lentogenic F cleavage site sequence. A synthetic wildtype ILTV glycoprotein D (SEQ ID NO:16 encoding SEQ ID NO:17) was chemically synthesized. Donor plasmid pHVTIG1gDCaFopt containing the HHV3gB promoter (Human Herpesvirus Type 3 glycoprotein B promoter) in the reverse orientation driving ILTV-gD+SV40 poly A tail, and SV40 promoter driving Newcastle fusion protein+synthetic poly A tail was constructed (see FIG. 23). Chicken embryo fibroblast cells (CEF) were used for in vitro recombination.

Recombinant Generation

The homologous recombination procedure as described in Example 1.1 was followed to make the recombinant vHVT308. Serial passaging was performed to pre-MSV+13.

Analysis of Recombinant by PCR

The PCR analysis procedure as described in Example 1.1 was performed to verify the recombinant vHVT308.

Expression Analysis

The expression analysis described in Example 1.1 was performed to analyze the expression of the recombinant vHVT308.

Results

The nucleotide and amino acid sequence of the donor plasmid pHVTIG1gDCaFopt are assigned SEQ ID NO as shown in FIG. 1.

Recombinant Generation and Expression Analyses

Dual Immunofluorescent staining was performed using chicken anti-sera (Pab) and a monoclonal antibody (Mab) followed by a FITC labeled anti-chicken IgG and TRITC labeled Alex Fluor donkey anti-mouse. All examined plaques of vHVT308 were found to express NDV-F and ILTV-gD proteins.

PCR Analysis of vHVT308

Figure 24:
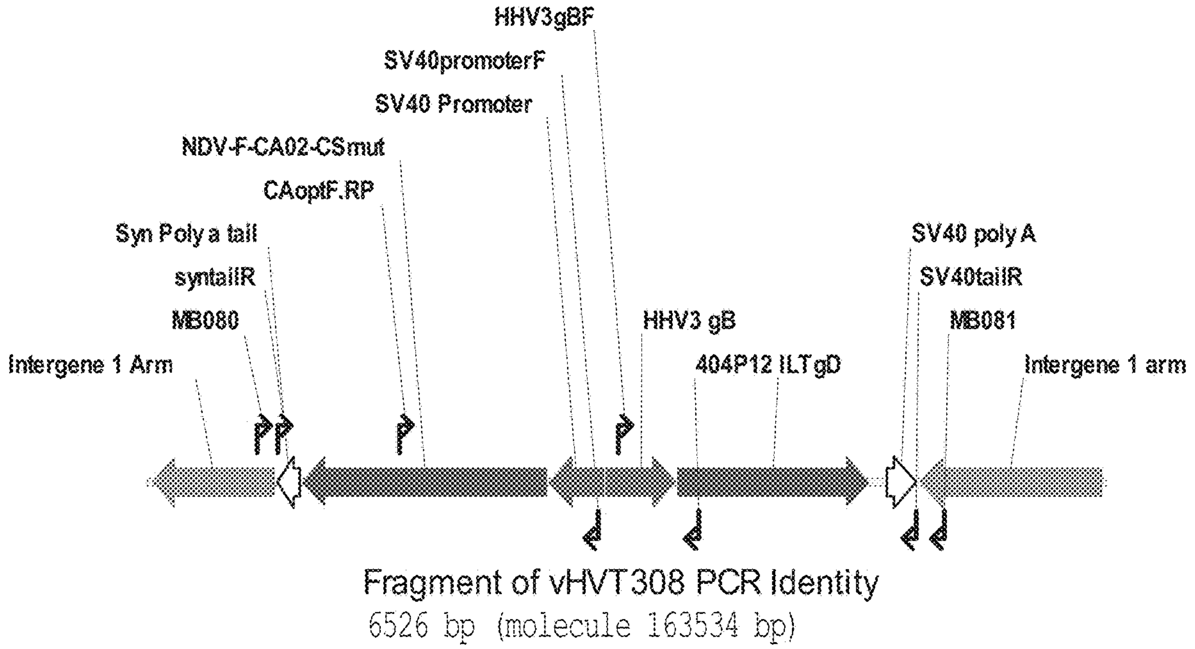
FIG. 24 depicts schematic representation of primer binding sites for vHVT308.
Figure 25:
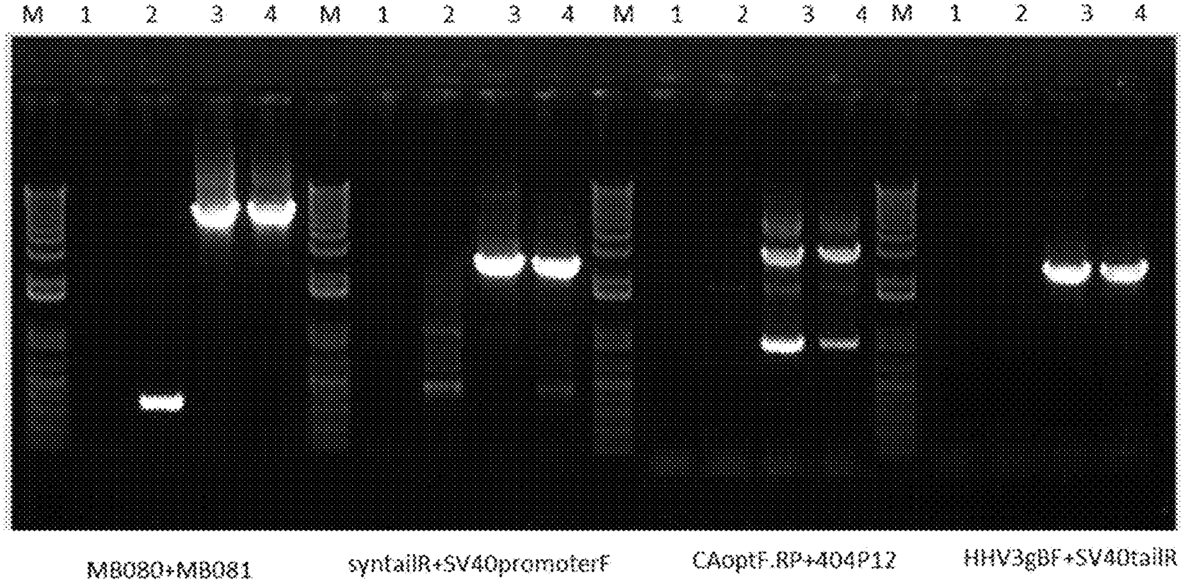
FIG. 25 depicts PCR identity result of vHVT308.

Purity of recombinant virus was verified by PCR using primer pairs that are specific to the HVT flanking arms, the promoters, the NDV-F and ILTV-gD genes, and the poly A tails. The PCR results demonstrate that recombinant virus vHVT308 carries the intended expression cassette and the virus stock is free from detectable amounts of parental HVT virus (Table 6.1 and FIGS. 24 and 25).

TABLE 6.1

Expected PCR bands using specific primer sets

| Primer set | HVT FC126 | vHVT308 |
|---|---|---|
| MB080 + MB081 | 323 bp | 4697 bp |
| syntailR + SV40promoterF | — | 2196 bp |
| CAoptF.RP + 404P12 | — | 2056 bp |
| HHV3gBF + SV40tailR | — | 2043 bp |

PCR reactions with all primer pairs resulted in the expected PCR products and banding patterns. As shown above, there is no evidence of parental HVT virus in vHVT308 and vHVT308 is stable at pre-MSV+13 passages.

Conclusion

Based on PCR testing and immunofluorescence analysis, vHVT308 is a recombinant HVT virus containing an NDV-F gene under the control of an SV40 promoter and an ILTV-gD gene under the control of an HHV3gB promoter. vHVT308 is free of any detectable parental HVT virus.

Example 1.9 Construction of Recombinant vHVT322 Expressing NDV-F and ILTV-gD

The objective of the study is to construct a recombinant HVT in which an expression cassette containing an mCMV promoter, Newcastle Disease virus fusion protein (NDV-F), internal ribosome entry site (IRES), Infectious Laryngotracheitis glycoprotein D (ILTV-gD), and Simian virus 40 poly A tail (SV40 poly A) will homologously recombine with the flanking arms in the intergenic region 1 (IG1) of vHVT13 (HVT+IBD).

Figure 26:
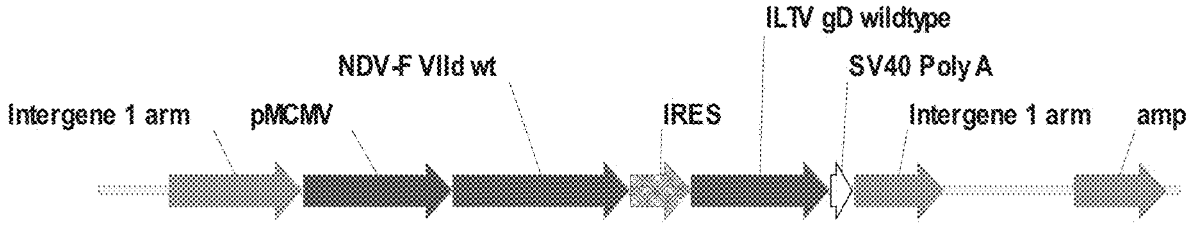
FIG. 26 depicts pFwtIRESgD plasmid map.

The parental virus used in the construct is vHVT13. A Newcastle disease virus Fusion Protein (NDV-F) corresponding to the wildtype genotype VIId sequence (SEQ ID NO:4 encoding SEQ ID NO:5) was chemically synthesized (GenScript). The F protein cleavage site of this synthetic gene was altered to match a lentogenic F cleavage site sequence and the resultant NDV-F gene sequence has 99% nucleotide as well as amino acid sequence identity to NDV-F sequence deposited in GenBank (AY337464). A synthetic wildtype ILTV glycoprotein D (SEQ ID NO:16 encoding SEQ ID NO:17) was chemically synthesized. Donor plasmid_pFwaRESgD contained the left flanking arm of IG1, mCMV (mouse CMV IE) promoter, NDV-F, IRES, ILTV-gD, SV40 poly A, and the right flanking arm of IG1 (see FIG. 26). Chicken embryo fibroblast cells (CEF) were used for in vitro recombination.

Recombinant Generation

The homologous recombination procedure as described in Example 1.1 was followed to make the recombinant vHVT322. Serial passaging was performed to pre-MSV+13.

Analysis of Recombinant by PCR

The PCR analysis procedure as described in Example 1.1 was performed to verify the recombinant vHVT322.

Expression Analysis

The expression analysis described in Example 1.1 was performed to analyze the expression of the recombinant vHVT322.

Results

The nucleotide and amino acid sequence of the donor plasmid pFwtIRESgD are assigned SEQ ID NO as shown in FIG. 1.

Recombinant Generation and Expression Analyses

Dual Immunofluorescent staining was performed using chicken anti-sera (Pab) and a monoclonal antibody (Mab) followed by a FITC labeled anti-chicken IgG and TRITC labeled Alex Fluor donkey anti-mouse. All examined TRITC positive plaques of vHVT322 were found to express NDV-F and ILTV-gD proteins.

PCR Analysis of vHVT322

Figure 27:
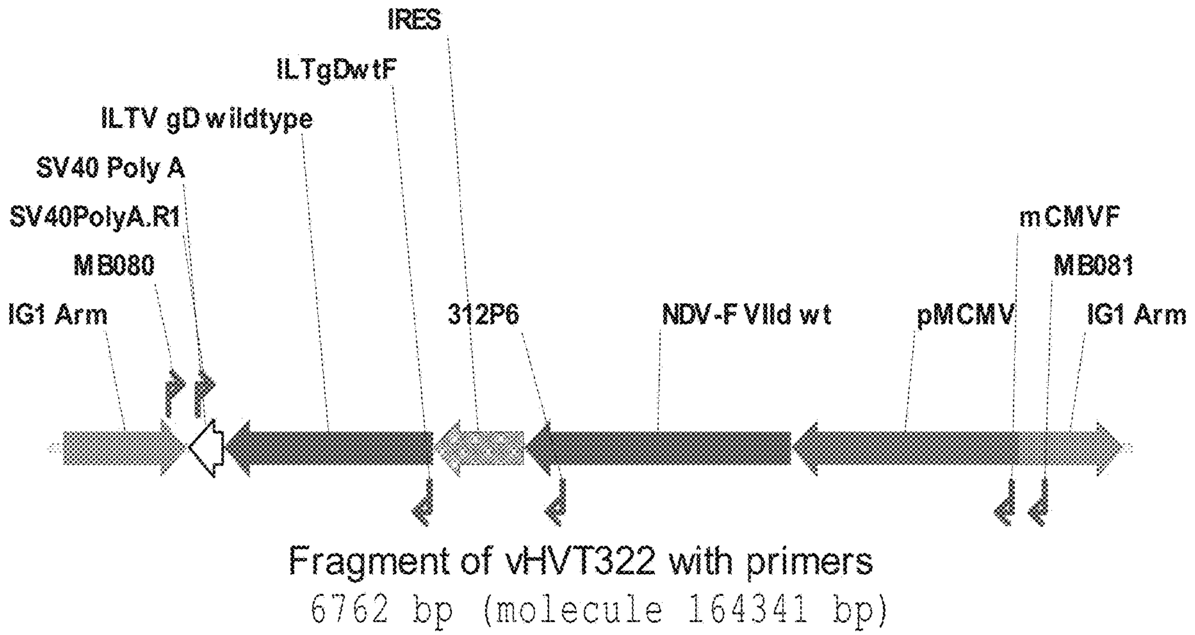
FIG. 27 depicts schematic representation of primer binding sites for vHVT322.
Figure 28:
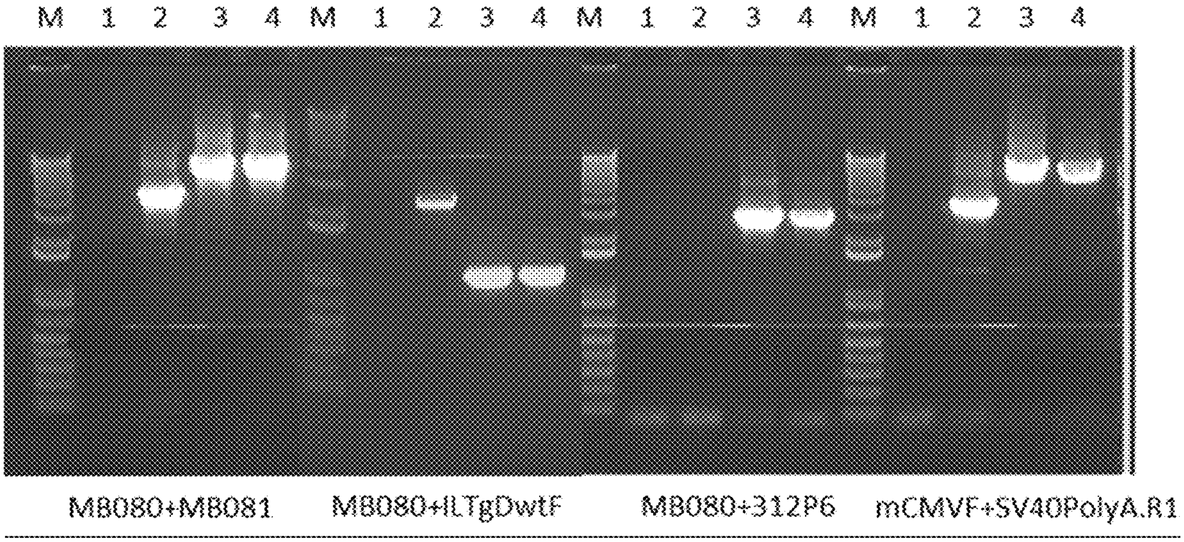
FIG. 28 depicts PCR identity result of vHVT322.

Purity of recombinant virus was verified by PCR using primer pairs that are specific to the HVT flanking arms, the promoter, the NDV-F and ILTV-gD genes, and the poly A tail. The PCR results demonstrate that recombinant virus vHVT322 carries the intended expression cassette and the virus stock is free from detectable amounts of parental vHVT13 (Table 6.2 and FIGS. 27 and 28).

TABLE 6.2

Expected PCR bands using specific primer sets

| Primer set | vHVT13 | vHVT322 |
|---|---|---|
| MB080 + MB081 | 3350 bp | 5804 bp |
| MB080 + ILTgDwtF | — | 1653 bp |
| MB080 + 312P6 | — | 2485 bp |
| mCMVF + SV40PolyA.R1 | 3021 bp | 5105 bp |

PCR reactions with all primer pairs resulted in the expected PCR products and banding patterns. As shown above, there is no evidence of parental vHVT13 virus in vHVT322.

Conclusion

Based on PCR testing and immunofluorescence analysis, vHVT322 is a recombinant HVT virus containing an NDV-F and ILTV-gD gene under the control of mCMV promoter. vHVT322 is free of any detectable parental vHVT13 virus.

Example 1.10 Construction of Recombinant vHVT406 Expressing ILT-gDwt

The objective of the study is to construct a recombinant HVT of which the SORF3-US2 site contains the SV40 promoter, Infectious Larygotracheitis gD, and synthetic poly A tail for homologous recombination into HVT FC126.

Figure 29:
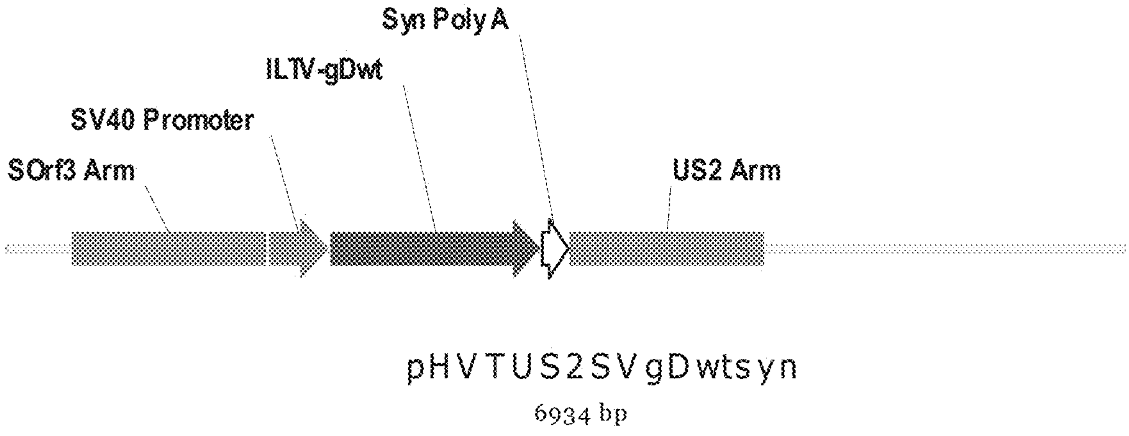
FIG. 29 depicts pHVTUS2SVgDwtsyn plasmid map.

The parental virus used in the construct is HVT FC126. A synthetic Infectious Laryngotracheitis Virus (ILTV) wild-type glycoprotein D (gDwt) was chemically synthesized. Donor plasmid pHVTUS2SVgDwtsyn contained the SORF3 and US2 arms of HVT FC126, SV40 promoter, ILTV gDwt (SEQ ID NO:16 encoding SEQ ID NO:17) and synthetic poly A (see FIG. 29). Chicken embryo fibroblast cells (CEF) were used for in vitro recombination.

Recombinant Generation

The homologous recombination procedure as described in Example 1.1 was followed to make the recombinant vHVT406. Serial passaging was performed to pre-MSV+13 (x+12).

Analysis of Recombinant by PCR

The PCR analysis procedure as described in Example 1.1 was performed to verify the recombinant vHVT406.

Expression Analysis

The expression analysis described in Example 1.1 was performed to analyze the expression of the recombinant vHVT406.

Results

The nucleotide and amino acid sequence of the donor plasmid pHVTUS2SVgDwtsyn are assigned SEQ ID NO as shown in FIG. 1.

Recombinant Generation and Expression Analyses

Genomic DNA of HVT virus was co-electroporated with pHVTUS2SVgDwtsyn donor plasmid to generate recombinant HVT using homologous recombination technique. Recombinant virus was separated from parental HVT virus by immunofluorescent positive well selection and PCR screening in multiple rounds of plaque purification. A plaque purified recombinant HVT virus expressing the ILTV-gD protein was designated vHVT406.

Recombinant vHVT406 viral plaques were visualized using both the TRITC and FITC filters for the dual staining. The FITC showed the ILTV-gDwt expression and the TRITC showed the HVT expression. Because of the small wells of the 96 well plates, each well was recorded with the plaques first counted with the TRITC filter and then recounted with the FITC filter. A combined 600+ plaques were counted between the pre-MSV and pre-MSV+13 passage. All the plaques were positive for both the FITC and TRITC for both passages.

PCR Analysis of vHVT406

Figure 30:
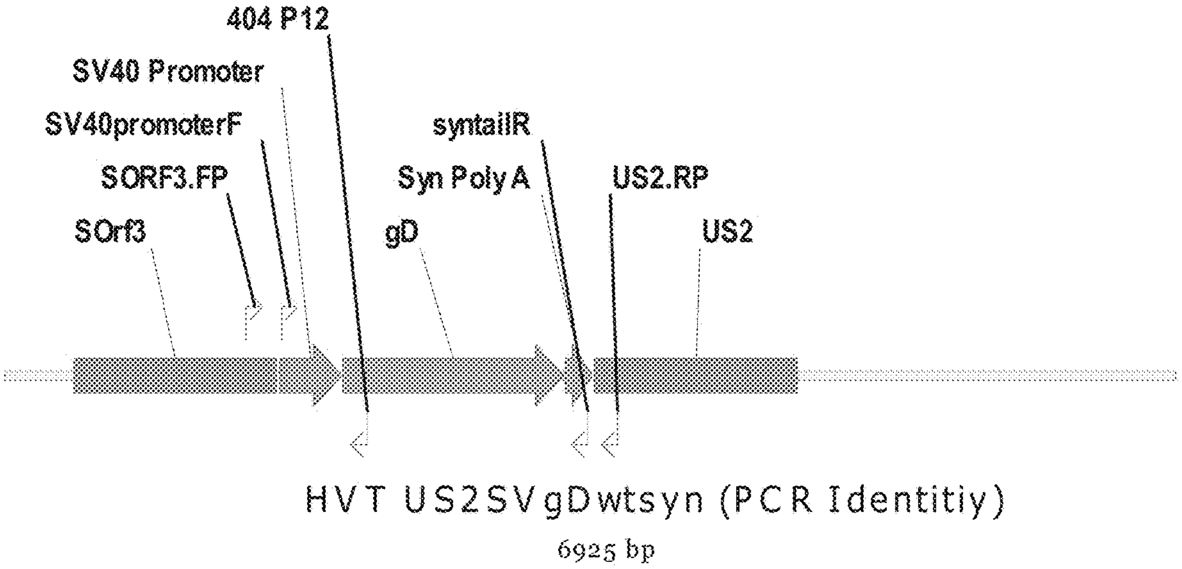
FIG. 30 depicts schematic representation of primer binding sites for vHVT406.
Figure 31:
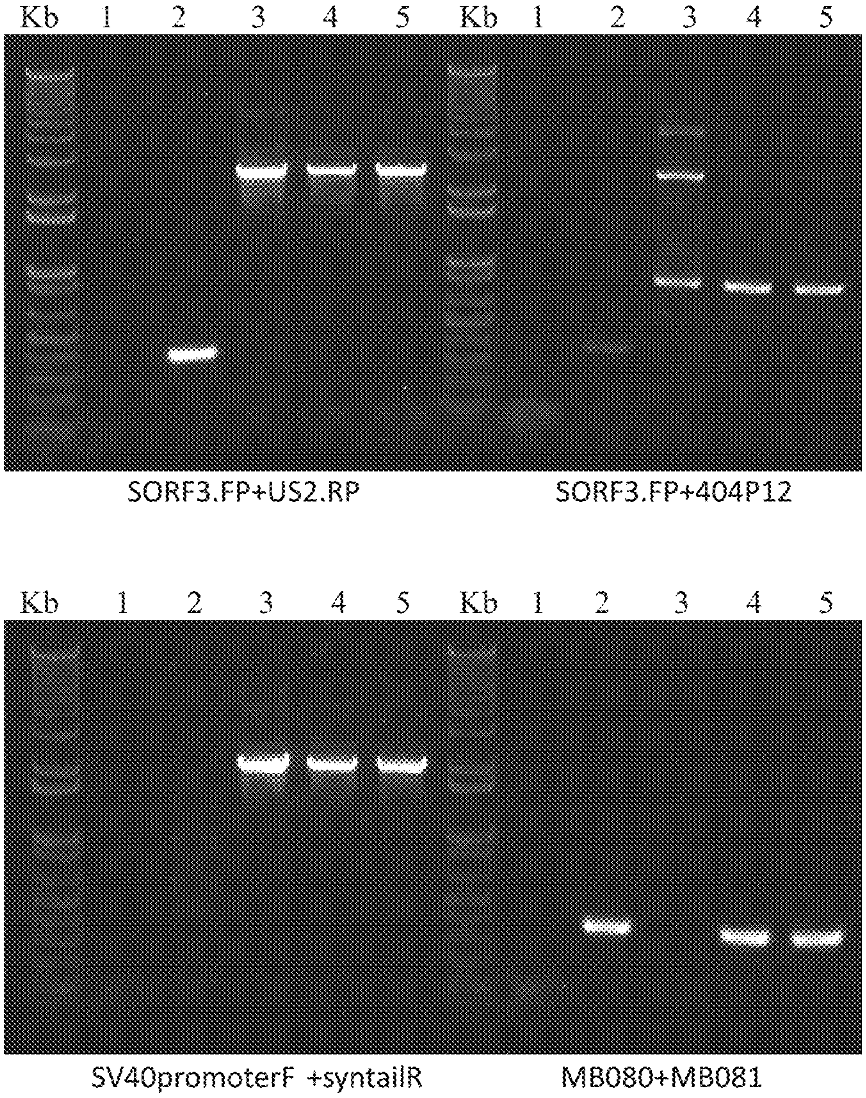
FIG. 31 depicts PCR identity result of vHVT406.

PCR analysis of vHVT406 was performed using the PCR primers listed in Table 6.3 (see FIG. 30). As shown in FIG. 31, the sizes of PCR products after gel electrophoresis correspond well with the expected sizes and the banding patterns. There is no evidence of the parental HVT FC126 virus in vHVT406.

TABLE 6.3

Expected PCR bands using specific primer sets

| primer | HVT FC126 | pHVTUS2SVgDwtsyn | vHVT406 |
|---|---|---|---|
| SORF3.FP + US2.RP | 0.334 | 2.218 | 2.218 |
| SORF3.FP + 404P12 | — | 0.733 | 0.733 |
| SV40promoterF + syntailR | — | 1.829 | 1.829 |
| MB080 + MB081 | 0.323 | — | 0.323 |
| **primer** | **SB-1** | **pHVTUS2SVgDwtsyn** | **vHVT406** |
| SB1SORF4 + SB1US2R | 0.989 | — | — |

Conclusion

Based on PCR testing and immunofluorescence analysis, vHVT406 is a recombinant HVT virus containing an SV40 promoter, ILTV-gDwt gene, and synthetic poly A tail in the SOrf3-US2 site. vHVT406 is free of any detectable parental HVT virus.

Example 1.11 In Vitro Stability Study of the HVT Vectors

The HVT vectors constructed above were tested for genomic/expression stability after multiple in vitro passages in Chicken embryo fibroblast cells (CEF). The HVT vectors expressing two genes were stable after multiple passages. Contrary to the common knowledge that HVT with multiple inserts are less stable, the results demonstrated surprisingly that the HVT vectors of the present invention are stable and express two genes efficiently.

Example 2 Newcastle Disease (ND) Efficacy Induced at D28 by vHVT306, vHVT309, vHVT310 & vHVT311 in SPF Chicks The aim of the study was to assess the efficacy of four HVT recombinant constructs (vHVT306, vHVT309, vHVT310 & vHVT311) expressing the IBDV VP2 gene and NDV F gene administered to one-day-old SPF chickens against Newcastle disease challenges (Texas GB strain) performed on D28.

The characteristics of these vaccine candidates are described in Table 7 below.

TABLE 7

Characteristics of the vectors used in the challenge study

| Name | Parental virus | gene | Promoter/ linker | Poly-A | Locus |
|---|---|---|---|---|---|
| vHVT306* | vHVT13** | IBDV VP2 | mCMV IE | SV40 Poly A | IG1 |
| | | NDV F | SV40 | Synthetic PolyA | SORF3-US2 |
| vHVT309 | vHVT13 | IBDV VP2 | mCMV IE | SV40 poly A | IG1 |
| | | NDV F | SV40 | Synthetic PolyA | IG1 |
| vHVT310 | vHVT13 | IBDV VP2 | mCMV IE | N/A | IG1 |
| | | NDV F | IRES | SV40 poly A | IG1 |
| vHVT311 | vHVT13 | IBDV VP2 | mCMV IE | N/A | IG1 |
| | | NDV F | P2A | SV40 poly A | IG1 |

vHVT306*: the vHVT vector expressing IBDV VP2 and NDV F (see U.S. Pat. No. 9,114,108), used as a control.

vHVT13** is the active ingredient of the licensed VAXXITEK HVT-IBD vaccine based on an HVT vector expressing the IBDV VP2 gene (described as vHVT17 in U.S. Pat. No. 5,980,906 and EP 0 719 864).

Ninety five one-day-old specific pathogen free (SPF) chicks were assigned to 5 groups as shown in Table 8. All birds from groups 1 to 4 (20 birds/group) were vaccinated by the subcutaneous (SC) route with 0.2 mL of different HVT-IBD+ND constructs at the dose indicated (see Table 8). The 15 birds from group 5 were left unvaccinated. Twenty eight (D28) days post-vaccination, the birds in each group were challenged with NDV Texas GB strain by the intramuscular (IM) route ($10^{4.0}$ egg infectious dose 50% (EID50) in 0.1 mL/bird). Birds were observed for clinical signs during 14 days after challenge. Birds that did not show any ND clinical signs (including central nervous, or respiratory signs and/or death) for up to 14 days post-challenge were considered as protected.

Results of protection are shown in Table 8. All control birds of group 5 died after the challenge. Protection in the vaccinated groups reached at least 90%.

TABLE 8

ND efficacy induced by different HVT-IBD + ND double constructs in SPF chicks

| Group | Vaccine | Dose (PFU) | ND protection after D 28 challenge |
|---|---|---|---|
| 1 | vHVT306* | 1580 | 95% (19/20) |
| 2 | vHVT309 | 1680 | 90% (18/20) |
| 3 | vHVT310 | 2840 | 95% (19/20) |
| 4 | vHVT311 | 2980 | 90% (18/20) |
| 5 | — | — | 0% (0/15) |

vHVT306*: used as a control

Example 3 IBD Efficacy Induced by vHVT309, vHVT310, vHVT311 and vHVT407 Against a Standard IBDV Challenge at D35

The aim of the study was to assess the efficacy of three HVT recombinant constructs (vHVT309, vHVT310 & vHVT311) expressing the IBDV VP2 gene and NDV F gene and one construct (vHVT407) expressing the IBDV VP2 gene and ILTV gD gene administered to one-day-old SPF chickens against standard IBDV challenge performed on D35.

One-day-old specific pathogen free (SPF) chicks were assigned to 4 groups as shown in Table 9. All birds from groups 1 to 4 (20 birds/group) were vaccinated by the subcutaneous (SC) route with 0.2 mL of different HVT-IBD+ND or HVT-IBD+ILT constructs at the dose indicated. The 20 birds from group 5 were left unvaccinated. Thirty five days after vaccination (at D35), all birds were challenged with the infectious bursal disease virus (IBDV) classical STC strain by the intraocular (TO) route ($10^{2.0}$ EID50 in 0.03 mL/bird). Four days post-challenge (at D39) all birds were terminated and necropsied to examine for gross bursal lesions.

Results of protection are shown in Table 9. All vaccinated birds (except two vHVT311-vaccinated birds) were protected against IBD, whereas none of the control birds were protected.

TABLE 9

IBD efficacy induced by different HVT-IBD + ND or HVT-IBD + ILT double constructs in SPF chicks after challenge at D 35 with STC IBDV strain

| Group | Vaccine | Dose (PFU) | IBD STC protection after D 35 challenge |
|---|---|---|---|
| 1 | vHVT309 | 2180 | 100% (20/20) |
| 2 | vHVT310 | 3980 | 100% (20/20) |
| 3 | vHVT311 | 3180 | 90% (18/20) |
| 4 | vHVT407 | 1220 | 100% (20/20) |
| 5 | — | — | 0% (0/20) |

Example 4 IBD Efficacy Induced by vHVT309, vHVT310, vHVT311 and vHVT407 Against a Variant IBDV Challenge at D35

The aim of the study was to assess the efficacy of three HVT recombinant constructs (vHVT309, vHVT310 & vHVT311) expressing the IBDV VP2 gene and NDV F gene and one construct (vHVT407) expressing the IBDV VP2 gene and ILTV gD gene administered to one-day-old SPF chickens against a variant (Delaware E) IBDV challenge performed on D35.

One-day-old specific pathogen free (SPF) chicks were assigned to 6 groups as shown in Table 10. All birds from groups 1 to 4 (19-20 birds/group) were vaccinated by the subcutaneous (SC) route with 0.2 mL of different HVT-IBD+ND or HVT-IBD+ILTconstructs at the dose indicated. Birds from group 5 (19 birds) and group 6 (18 birds) were left unvaccinated. At D35, all birds from groups 1 to 5 were challenged with the infectious bursal disease virus (IBDV) variant Delaware E strain by the intraocular (TO) route ($10^{3.0}$ EID50 in 0.03 mL/bird). Birds from group 6 were left unchallenged. At D46, body weight and bursal weight of all birds were measured. The B/B wt. ratios (bursa weight/body weight ratio×100) were calculated for all groups.

Results of protection are shown in Table 10. Vaccinated birds from groups 1 and 2 had a mean B/B wt. ratio similar as that of non-vaccinated non-challenged controls (group 6) and greater than those of non-vaccinated challenged controls (group 5). Birds of group 3 were not protected and birds of group 4 were partially protected. Surprisingly, vHVT310 which contains IRES provided better protection than vHVT311 which contains P2A.

TABLE 10

IBD efficacy induced by different HVT-IBD + ND or HVT-IBD + ILT double constructs in SPF chicks after challenge at D 35 with variant E IBDV strain

| Group | Vaccine | Dose (PFU) | Number of birds | IBDV challenge at D 35 | Mean B/B wt. ratio |
|---|---|---|---|---|---|
| 1 | vHVT309 | 2180 | 20 | Yes | 0.43 |
| 2 | vHVT310 | 3980 | 20 | Yes | 0.50 |
| 3 | vHVT311 | 3180 | 20 | Yes | 0.18 |
| 4 | vHVT407 | 1220 | 19 | Yes | 0.32 |
| 5 | — | — | 19 | Yes | 0.13 |
| 6 | — | — | 18 | No | 0.45 |

Example 5 IBD Efficacy Induced by vHVT306, vHVT309 & vHVT310 Against a vvIBDV Challenge at D28 in Broilers The aim of the study was to assess the efficacy of three HVT recombinant constructs (vHVT306, vHVT309 & vHVT310) expressing the IBDV VP2 gene and NDV F gene administered to one-day-old broiler chickens against vvIBDV challenge performed on D28.

Seventy one-day-old broiler chicks (Hubbard JA957 line) were assigned to 5 groups as shown in Table 11. All birds from groups 2 to 5 (about 15 birds/group) were vaccinated by the subcutaneous (SC) route with 0.2 mL of different HVT-IBD+ND constructs at the dose indicated. Ten birds from group 1 were left unvaccinated. Twenty eight days after vaccination (at D28), all birds were challenged with the very virulent IBDV (vvIBDV) 91-168 strain by the intraocular (TO) route ($10^{4.3}$ EID50 in 0.05 mL/bird). Ten days post-challenge (at D38) all birds were terminated and necropsied to examine for gross bursal lesions. Bursal and body were weighted and histopathology was performed on the bursa. Histological lesions of the bursa were scored from 0 to 5 according to the following scale: 0—No lesion, normal bursa; 1—1% to 25% of the follicles show lymphoid depletion (i.e., less than 50% of depletion in 1 affected follicle), influx of heterophils in lesions; 2—26% to 50% of the follicles show nearly complete lymphoid depletion (i.e., with more than 75% of depletion in 1 affected follicle), the affected follicles show necrosis lesions and severe influx of heterophils may be detected; 3—51% to 75% of the follicles show lymphoid depletion; affected follicles show necrosis lesions and a severe influx of heterophils is detected; 4—76% to 100% of the follicles show nearly complete lymphoid depletion; hyperplasia and cyst structures are detected; affected follicles show necrosis lesions and severe influx of heterophils is detected; and 5—100% of the follicles show nearly complete lymphoid depletion; complete loss of follicular structure; thickened and folded epithelium; fibrosis of bursal tissue. Birds were considered as protected if they did not show clinical signs post-challenge and if their histology score was ≤2.

There were some early mortalities in the first week in this batch of broilers likely due to colibacillosis. The dose of the tested vaccines was lower than expected (2000 PFU). Results of protection are shown in Table 11. Partial protection was induced by vaccination which shows vHVT310 being higher than vHVT306 and vHVT309.

TABLE 11

IBD efficacy induced by different HVT-IBD + ND double constructs in broiler chicks after challenge at D 28 with vvIBDV strain

| Group | Vaccine | Dose (PFU) | Mean Bursal/body weight ratio (*1000) | Protection based on histopathology score |
|---|---|---|---|---|
| 1 | — | — | 0.75 | 0% |
| 2 | vHVT306 | 955 | 1.07 | 20% |
| 3 | vHVT309 | 741 | 0.89 | 20% |
| 4 | vHVT310 | 708 | 1.38 | 53% |
| 5 | vHVT13* | 2000 | 1.99 | 80% |

vHVT13*: used as a control.

Example 6 ND Efficacy Induced by vHVT306, vHVT309 & vHVT310 Against a Velogenic NDV Challenge at D42 in Broilers The aim of the study was to assess the efficacy of three HVT recombinant constructs (vHVT306, vHVT309 & vHVT310) expressing the IBDV VP2 gene and NDV F gene administered to one-day-old broiler chickens against velogenic NDV challenge performed on D42.

One-day-old broiler chicks (Hubbard JA957 line) were assigned to 4 groups as shown in Table 12. All birds from groups 2 to 4 (16-20 birds/group) were vaccinated by the subcutaneous (SC) route with 0.2 mL of different HVT-IBD+ND constructs at the dose indicated. Twelve birds from group 1 were left unvaccinated. Forty two days after vaccination (at D42), all birds were challenged with the velogenic NDV Herts 33 strain by the intramuscular (IM) route ($10^{5.0}$ EID50 in 0.2 mL/bird). All birds were observed for clinical signs during 14 days post-challenge. Birds were considered as protected if they did not die or show ND clinical signs.

There were some early mortalities in the first week in this batch of broilers likely due to colibacillosis. The dose of the tested vaccines was lower than expected (2000 PFU). Results of protection are shown in Table 12. Best protections were induced by vaccination with vHVT309 & vHVT310, followed by vHVT306.

TABLE 12

ND efficacy induced by different HVT-IBD + ND double constructs in broiler chicks after challenge at D 42 with velogenic NDV strain

| Group | Vaccine | Dose (PFU) | Protection against mortality | Protection against mortality & morbidity |
|---|---|---|---|---|
| 1 | — | — | 8.3% | 0% |
| 2 | vHVT306 | 955 | 68.8% | 62.5% |
| 3 | vHVT309 | 741 | 85% | 85% |
| 4 | vHVT310 | 708 | 85% | 80% |

Example 7 ND Efficacy Induced by vHVT306, vHVT309 & vHVT310 Against a Velogenic NDV Challenge at D42 in Broilers The aim of the study was to re-assess the efficacy of three HVT recombinant constructs (vHVT306, vHVT309 & vHVT310) expressing the IBDV VP2 gene and NDV F gene administered to one-day-old broiler chickens against velogenic NDV challenge performed on D42.

One-day-old broiler chicks (Hubbard JA957 line) were assigned to 4 groups as shown in Table 13. All birds from groups 2 to 4 (16-20 birds/group) were vaccinated by the subcutaneous (SC) route with 0.2 mL of different HVT-IBD+ND constructs at 2000 PFU. Nineteen birds from group 1 were left unvaccinated. Forty two days after vaccination (at D42), all birds were challenged with the velogenic NDV Herts 33 strain by the intramuscular (IM) route ($10^{5.0}$ EID50 in 0.2 mL/bird). All birds were observed for clinical signs during 14 days post-challenge. Birds were considered as protected if they did not die or show ND clinical signs.

Results of protection are shown in Table 13. Overall, the levels of protection were higher than the previous study (see example 6), but they follow the same trend: best protections were induced by vaccination with vHVT309 & vHVT310, followed by vHVT306.

The results showed that vHVT309 is more efficacious than vHVT306 against ND challenges in SPF as well as broilers (Tables 12 &13), suggesting that inserting heterologous polynucleotides in one locus have less negative impact on the overall fitness of the virus than inserting in multiple loci.

TABLE 13

ND efficacy induced by different HVT-IBD + ND double constructs in broiler chicks after challenge at D 42 with velogenic NDV strain

| Group | Vaccine | Dose (PFU) | Protection against mortality | Protection against mortality & morbidity |
|---|---|---|---|---|
| 1 | — | — | 0% | 0% |
| 2 | vHVT306 | 955 | 75% | 75% |
| 3 | vHVT309 | 741 | 94% | 89% |
| 4 | vHVT310 | 708 | 94% | 94% |

Example 8 IBD Efficacy Induced by vHVT306, vHVT309 & vHVT310 Against a Standard IBDV Challenge at D14 in SPF Chicks The aim of the study was to assess the efficacy of three HVT recombinant constructs (vHVT306, vHVT309 & vHVT310) expressing the IBDV VP2 gene and NDV F gene administered to one-day-old SPF chickens against standard IBDV challenge performed at D14.

One-day-old specific pathogen free (SPF) chicks were assigned to 4 groups as shown in Table 14. All birds from groups 1 to 3 (21-22 birds/group) were vaccinated by the subcutaneous (SC) route with 0.2 mL of different HVT-IBD+ND constructs at the dose indicated. The 22 birds from group 4 were left unvaccinated. Fourteen days after vaccination (at D14), all birds were challenged with the infectious bursal disease virus (IBDV) classical STC strain by the intraocular (TO) route ($10^{1.4}$ EID50 in 0.03 mL/bird). Four days post-challenge (at D18) all birds were terminated and necropsied to examine for gross bursal lesions.

Results of protection are shown in Table 14 Similar levels of IBD protection were induced by the 3 experimental vaccines, whereas all but one control birds was infected.

TABLE 14

IBD efficacy induced by different HVT-IBD + ND double constructs in SPF chicks after challenge at D 14 with STC IBDV strain

| Group | Vaccine | Dose (PFU) | IBD STC protection after D 14 challenge (infected/total) |
|---|---|---|---|
| 1 | vHVT306 | 2061 | 68.2% (7/22) |
| 2 | vHVT309 | 1476 | 76.2% (5/21) |
| 3 | vHVT310 | 1970 | 68.2% (7/22) |
| 4 | — | — | 4.5% (21/22) |

Example 9 IBD Efficacy Induced by vHVT306, vHVT309 & vHVT310 in SPF Chicks after Variant IBD Challenge at D14

The aim of the study was to assess the efficacy of three HVT recombinant constructs (vHVT306, vHVT309 & vHVT310) expressing the IBDV VP2 gene and NDV F gene administered to one-day-old SPF chickens against variant IBDV challenge performed at D14.

One-day-old specific pathogen free (SPF) chicks were assigned to 5 groups as shown in Table 15. All birds from groups 1 to 3 (20 birds/group) were vaccinated by the subcutaneous (SC) route with 0.2 mL of different HVT-IBD+ND constructs at the dose indicated. Birds from group 4 and group 5 (19-20 birds/group) were left unvaccinated. At D14, all birds from groups 1 to 4 were challenged with the infectious bursal disease virus (IBDV) variant Delaware E strain by the intraocular (TO) route ($10^{2.2}$ EID50 in 0.03 mL/bird). Birds from group 5 were left unchallenged. At D25, body weight and bursal weight of all birds were measured. The B/B wt. ratios (bursa weight/body weight ratio×100) were calculated for all groups.

Results of protection are shown in Table 15. Partial protection was induced at D14 by the 3 vaccines, protection being higher for vHVT309 and vHVT310.

Recombinant vHVT306 and vHVT309 have two independent expression cassettes (two mRNAs). The constructs expressing two genes through an IRES or P2A (for example, vHVT310, vHVT317, vHVT311, vHVT316, vHVT322) are not only in one insertion site, but also the genes are expressed from a single mRNA. Comparing all the data presented in Tables 11 to 19, it shows that one insertion site recombinants vHVT309 and vHVT310 are more efficacious than two insertion site recombinant vHVT306, indicating that HVT recombinants carrying more than one heterologous polynucleotides in one insertion locus are biologically more fit than HVT recombinants carrying heterologous polynucleotides in multiple insertion loci. Furthermore, surprisingly, expressing more than one heterologous polynucleotides from a single mRNA expressed through an IRES has less negative impact on IBD efficacy, particularly in broilers (see results on Table 11).

TABLE 15

IBD efficacy induced by different HVT-IBD + ND double constructs in SPF chicks after challenge at D 14 with variant E IBDV strain

| Group | Vaccine | Dose (PFU) | Number of birds | IBDV challenge at D 14 | Mean B/B wt. ratio |
|---|---|---|---|---|---|
| 1 | vHVT306 | 2061 | 20 | Yes | 0.18 |
| 2 | vHVT309 | 1476 | 20 | Yes | 0.33 |
| 3 | vHVT310 | 1970 | 20 | Yes | 0.27 |
| 4 | — | — | 19 | Yes | 0.13 |
| 5 | — | — | 20 | No | 0.64 |

Example 10 IBD Efficacy Induced by vHVT306, vHVT309 & vHVT310 Against a Standard IBDV Challenge at D28 in SPF Chicks The aim of the study was to assess the efficacy of three HVT recombinant constructs (vHVT306, vHVT309 & vHVT310) expressing the IBDV VP2 gene and NDV F gene administered to one-day-old SPF chickens against standard IBDV challenge performed at D28.

One-day-old specific pathogen free (SPF) chicks were assigned to 4 groups as shown in Table 16. All birds from groups 1 to 3 (20-22 birds/group) were vaccinated by the subcutaneous (SC) route with 0.2 mL of different HVT-IBD+ND constructs at the dose indicated. The 22 birds from group 4 were left unvaccinated. Twenty eight days after vaccination (at D28), all birds were challenged with the infectious bursal disease virus (IBDV) classical STC strain by the intraocular (TO) route ($10^{2.0}$ EID50 in 0.03 mL/bird). Four days post-challenge (at D32) all birds were terminated and necropsied to examine for gross bursal lesions.

Results of protection are shown in Table 16. Full protection was induced by vHVT310 whereas only a few birds were not protected for the other vaccine candidates.

TABLE 16

IBD efficacy induced by different HVT-IBD + ND double constructs in SPF chicks after challenge at D 28 with STC IBDV strain

| Group | Vaccine | Dose (PFU) | IBD STC protection after D 28 challenge (infected/total |
|---|---|---|---|
| 1 | vHVT306 | 2061 | 86.4% (3/22) |
| 2 | vHVT309 | 1476 | 95.0% (1/20) |
| 3 | vHVT310 | 1970 | 100% (0/22) |
| 4 | — | — | 4.5% (21/22) |

Example 11 IBD Efficacy Induced by vHVT306, vHVT309 & vHVT310 in SPF Chicks after Variant IBD Challenge at D28

The aim of the study was to assess the efficacy of three HVT recombinant constructs (vHVT306, vHVT309 & vHVT310) expressing the IBDV VP2 gene and NDV F gene administered to one-day-old SPF chickens against variant IBDV challenge performed at D28.

One-day-old specific pathogen free (SPF) chicks were assigned to 5 groups as shown in Table 17. All birds from groups 1 to 3 (20 birds/group) were vaccinated by the subcutaneous (SC) route with 0.2 mL of different HVT-IBD+ND constructs at the dose indicated. Birds from group 4 and group 5 (18-19 birds/group) were left unvaccinated. At D28, all birds from groups 1 to 4 were challenged with the infectious bursal disease virus (IBDV) variant Delaware E strain by the intraocular (TO) route ($10^{2.2}$ EID50 in 0.03 mL/bird). Birds from group 5 were left unchallenged. At D39, body weight and bursal weight of all birds were measured. The B/B wt. ratios (bursa weight/body weight ratio×100) were calculated for all groups.

Results of protection are shown in Table 17. The B/B wt ratio for group 5 (unchallenged group) could not be obtained since this group was unexpectedly infected with the STC IBDV strain. Protection induced by vHVT310 was higher than that induced by vHVT306 and vHVT309.

TABLE 17

IBD efficacy induced by different HVT-IBD + ND double constructs in SPF chicks after challenge at D 28 with variant E IBDV strain

| Group | Vaccine | Dose (PFU) | Number of birds | IBDV challenge at D 28 | Mean B/B wt. ratio |
|---|---|---|---|---|---|
| 1 | vHVT306 | 2061 | 20 | Yes | 0.21 |
| 2 | vHVT309 | 1476 | 20 | Yes | 0.26 |
| 3 | vHVT310 | 1970 | 20 | Yes | 0.37 |
| 4 | — | — | 19 | Yes | 0.11 |
| 5 | — | — | 20 | No | ND* |

*Not done due to standard IBDV exposure in this group

Example 12 Newcastle Disease (ND) Efficacy Induced at D21 and D28 by vHVT306, vHVT309 & vHVT310 in SPF Chicks The aim of the study was to assess the efficacy of three HVT recombinant constructs (vHVT309, vHVT310 & vHVT311) expressing the IBDV VP2 gene and NDV F gene administered to one-day-old SPF chickens against Newcastle disease challenges (Texas GB strain) performed on D21 and D28.

One-day-old specific pathogen free (SPF) chicks were assigned to 4 groups as shown in Table 18. All birds from groups 1 to 3 (50 birds/group) were vaccinated by the subcutaneous (SC) route with 0.2 mL of different HVT-IBD+ND constructs at the dose indicated. The 30 birds from group 4 were left unvaccinated. Twenty one (D21) days post-vaccination, 20 birds from groups 1-3 and 15 birds from group 4 were challenged with NDV Texas GB strain by the intramuscular (IM) route ($10^{4.2}$ egg infectious dose 50% (EID50) in 0.1 mL/bird). Twenty eight (D28) days post-vaccination, 30 birds from groups 1-3 and 15 birds from group 4 were challenged with NDV Texas GB strain by the intramuscular (IM) route ($10^{4.3}$ egg infectious dose 50% (EID50) in 0.1 mL/bird). Birds were observed for clinical signs during 14 days after challenge. Birds that did not show any ND clinical signs (including central nervous, or respiratory signs and/or death) for up to 14 days post-challenge were considered as protected.

Results of protection are shown in Table 18. All control birds of group 4 died after the challenge. Protection induced by vHVT310 was the best followed by vHVT306 and vHVT309.

TABLE 18

ND efficacy at D 21 and D 28 induced by different HVT-IBD + ND double constructs in SPF chicks

| Group | Vaccine | Dose (PFU) | ND protection after D 21 challenge (protected/total) | ND protection after D 28 challenge (protected/total) |
|---|---|---|---|---|
| 1 | vHVT306* | 2248 | 80% (16/20) | 90% (27/30) |
| 2 | vHVT309 | 1765 | 60% (12/20) | 86.2% (25/29) |
| 3 | vHVT310 | 2106 | 85% (17/20) | 100% (29/29) |
| 4 | — | — | 0% (0/15) | 0% (0/15) |

vHVT306*: used as a control

Example 13 Marek's Disease (MD) Efficacy Induced by vHVT306, vHVT309 & vHVT310 in SPF Chicks The aim of the study was to assess the efficacy of three HVT recombinant constructs (vHVT309, vHVT310 & vHVT311) expressing the IBDV VP2 gene and NDV F gene administered to one-day-old SPF chickens against Marek's disease challenges (GA strain, 2 batches & 2 dilutions).

One-day-old specific pathogen free (SPF) chicks were assigned to 4 groups as shown in Table 19. All birds from groups 1 to 3 (20 birds/group) were vaccinated by the subcutaneous (SC) route with 0.2 mL of different HVT-IBD+ND constructs at the dose indicated. The 20 birds from group 4 were left unvaccinated. Four days post-vaccination (D4), 18-20 birds from groups 1-4 were challenged with two dilutions (1:5 and 1:640) of two different batches (#1 and #2) of the vMDV GA22 strain by the SC route. Birds were observed for clinical signs attributable to Marek's disease during 46-50 days post-hatch. At D46-D50, all remaining birds were necropsied and checked for Marek's disease lesions. Birds that did not show any MD clinical signs or lesions were considered as protected.

Results of protection are shown in Table 19. Infectivity in control birds of group 4 varied between 75-90%. Overall, protection induced by vHVT310 was the best followed closely by vHVT306 and then vHVT309.

TABLE 19

MD efficacy induced by different HVT-IBD + ND double constructs in SPF chicks against 2 different lots of GA22 challenge either diluted 1:5 or 1:640

| Group | Vaccine | Dose (PFU) | MD protect. GA22 lot #1 1:5 dil. | MD protect. GA22 lot #1 1:640 dil. | MD protect. GA22 lot #2 1:5 dil. | MD protect. GA22 lot #2 1:640 dil. |
|---|---|---|---|---|---|---|
| 1 | vHVT306* | 2420 | 75% (15/20) | 85% (17/20) | 26.3% (5/19) | 70% (14/20) |
| 2 | vHVT309 | 1893 | 50% (10/20) | 72.2% (13/18) | 55% (11/20) | 70% (14/20) |
| 3 | vHVT310 | 2127 | 80% (16/20) | 84.2% (16/19) | 40% (8/20) | 90% (18/20) |
| 4 | — | — | 25% (5/20) | 10% (2/20) | 10% (2/20) | 20% (4/20) |

vHVT306*: used as a control

Example 14 IBD Efficacy Induced by vHVT306 and vHVT407 Against a Classical IBDV Challenge at D21 in SPF Chicks The aim of the study was to assess the efficacy of two HVT recombinant constructs, one (vHVT306) expressing the IBDV VP2 gene and NDV F gene and the other (vHVT407) expressing the IBDV VP2 gene and ILTV gD gene administered to one-day-old SPF chickens against a classical IBDV challenge performed on D21.

Forty one-day-old SPF chicks (white Leghorn) were assigned to 3 groups as shown in Table 20. All birds from groups 2 & 3 (about 15 birds/group) were vaccinated by the subcutaneous (SC) route with 0.2 mL of vHVT306 or vHVT407 construct at the dose indicated. Ten birds from group 1 were left unvaccinated. Twenty one days after vaccination (at D21), all birds were challenged with the classical 52/70 Faragher IBDV strain by the intraocular (TO) route ($10^{2.0}$ EID50 in 0.05 mL/bird). Eleven days post-challenge (at D32) all birds were terminated and necropsied to examine for gross bursal lesions. Bursal and body were weighted to calculate the bursal on body weight ratio. Birds were considered as protected if they did not show clinical signs or bursal lesion post-challenge.

Results of protection are shown in Table 20. Complete IBD protection was induced by vaccination with vHVT306 or vHVT407.

TABLE 20

IBD efficacy induced by two HVT constructs expressing two genes in SPF chicks after challenge at D 21 with Faragher IBDV strain

| Group | Vaccine | Dose (log10 PFU) | Clinical signs #dead/ #sick/total | Mean Bursal/body weight ratio (*1000) | % with gross bursal lesion |
|---|---|---|---|---|---|
| 1 | — | — | 3/4/10 | 1.6 ± 0.7** | 100% |
| 2 | vHVT306* | 3.1 | 0/0/15 | 6.1 ± 1.1 | 0% |
| 3 | vHVT407 | 3.1 | 0/0/15 | 6.3 ± 1.1 | 0% |

vHVT306*: used as a control.
**mean ± standard deviation

Example 15 ILT Efficacy Induced by vHVT407 Against an ILTV Challenge at D21 in SPF Chicks The aim of the study was to assess the efficacy of two vHVT407 recombinant construct expressing the IBDV VP2 gene and the ILTV gD gene administered to one-day-old SPF chickens against an ILTV challenge performed on D21.

Twenty four one-day-old SPF chicks (white Leghorn) were assigned to 2 groups as shown in Table 21. All birds (about 12 birds/group) were vaccinated by the subcutaneous (SC) route with 0.2 mL of vHVT13 (used as a negative control) or vHVT407 construct at the dose indicated. Twenty one days after vaccination (at D21), all birds were challenged with the ILT-96-3 ILTV strain by the intratracheal (IT) route ($10^{3.6}$ EID50 in 0.5 mL/bird). The birds were observed for clinical signs for 11 days post-challenge. On Study Days 25-29 and 32 all the birds were observed for clinical signs including breathing pattern, conjunctivitis, depression and mortality. On Study Day 32, all the remaining birds were terminated. Birds were considered as protected if they did not show ILT clinical signs such as respiratory distress associated with coughing, sneezing, rales, depression, gasping and/or bloody mucous exudates, including mortality.

Results of protection are shown in Table 21. Significant ILT protection was induced by vaccination with vHVT407 in these challenge conditions.

TABLE 21

ILT efficacy induced by vHVT407 construct in SPF chicks after challenge at D 21 with ILT-96-3 ILTV strain

| Group | Vaccine | Dose (PFU) | Clinical signs #dead/#sick/total | Clinical Protection |
|---|---|---|---|---|
| 1 | vHVT13* | 3420 | 6/2/11 | 27% |
| 2 | vHVT407 | 2880 | 2/0/12 | 83% |

vHVT13*: used as a negative control.

Example 16 ILT Efficacy Induced by vHVT407, a Commercial HVT-ILT and a Commercial Chicken Embryo Origin (CEO) Vaccine Against an ILTV Challenge at D21 in Broiler Chicks The aim of the study was to assess the efficacy of vHVT407 recombinant construct expressing the IBDV VP2 gene and the ILTV gD gene administered to one-day-old broiler chickens compared to a commercial HVT-ILT vaccine (INNOVAX® ILT) against an ILTV challenge performed on D21.

Forty eight one-day-old commercial broiler chicks were assigned to 3 groups as shown in Table 22. All birds (about 12 birds/group) of groups 1-3 were vaccinated by the subcutaneous (SC) route with 0.2 mL of vHVT13 (used as a negative control), vHVT407 or INNOVAX® ILT (used as a positive control) constructs at the dose indicated. Twenty one days after vaccination (at D21), all birds were challenged with the ILT-96-3 ILTV strain by the intratracheal (IT) route ($10^{4.2}$ EID50 in 0.5 mL/bird). The birds were observed for clinical signs for 12 days post-challenge. On Study Days 25-29 and 32-33 all the birds were observed and scored for clinical signs including breathing pattern, conjunctivitis, depression and mortality. On Study Day 34, all the remaining birds were terminated. Birds were considered as protected if they did not show ILT clinical signs such as respiratory distress associated with coughing, sneezing, rales, depression, gasping and/or bloody mucous exudates, including mortality.

Results of protection are shown in Table 22. ILT protection was induced by vaccination with vHVT407, which was higher than that induced by INNOVAX ILT.

TABLE 22

ILT efficacy induced by vHVT407 and INNOVAX ILT constructs in broiler chicks after challenge at D 21 with ILT-96-3 ILTV strain

| Group | Vaccine | Dose | Clinical signs #dead/#sick/total | Clinical Protection |
|---|---|---|---|---|
| 1 | vHVT13* | 2200 PFU | 5/7/12 | 0% |
| 2 | vHVT407 | 1860 PFU | 1/4/11 | 55% |
| 3 | INNOVAX ILT** | 2240 PFU | 0/10/12 | 17% |

vHVT13*: used as a negative control.
**INNOVAX ® ILT used as a positive control

Example 17 Newcastle Disease (ND) Efficacy Induced at D14, D21 and D32 by vHVT310 & vHVT316 in SPF Chicks The aim of the study was to compare the onset of ND immunity of two HVT recombinant constructs (vHVT310 & vHVT316) expressing the IBDV VP2 gene and NDV F gene administered to one-day-old SPF chickens against Newcastle disease challenges (Texas GB strain) performed on D14, D21 and D32.

One-day-old specific pathogen free (SPF) chicks were assigned to 3 groups as shown in Table 23. All birds from groups 1 to 2 (59-70 birds/group; see table) were vaccinated by the subcutaneous (SC) route with 0.2 mL of different HVT-IBD+ND constructs at the dose indicated. The 45 birds from group 3 were left unvaccinated. At D14, D21 and D32, 15-30 birds (see table) from groups 1-3 were challenged with NDV Texas GB strain by the intramuscular (IM) route ($10^{4.0}$ EID50/bird) in 0.1 mL/bird). Birds were observed for clinical signs during 14 days after challenge. Birds that did not show any ND clinical signs (including central nervous, or respiratory signs and/or death) for up to 14 days post-challenge were considered as protected.

Results of protection are shown in Table 23. All control birds of group 3 died after the challenge. Protection levels induced by both vHVT310 and vHVT316 were similar, with a possible earlier onset of immunity induced by vHVT316.

TABLE 23

ND efficacy at D 14, D 21 and D 32 induced by different HVT-IBD + ND double constructs in SPF chicks

| Group | Vaccine | Dose (PFU) | ND protection after D 14 challenge (protected/total) | ND protection after D 21 challenge (protected/total) | ND protection after D 32 challenge (protected/total) |
|---|---|---|---|---|---|
| 1 | vHVT310 | 2473 | 30% (6/20) | 80% (16/20) | 97% (29/30) |
| 2 | vHVT316 | 2367 | 45% (9/20) | 80% (16/20) | 100% (19/19) |
| 3 | — | — | 0% (0/15) | 0% (0/15) | 0% (0/15) |

Example 18 ILTV Efficacy Induced by HVT Vectors Expressing ILTV gD and IBDV VP2 or Expressing ILTV gD and NDV F The aim of the study is to assess the efficacy of the HVT recombinant constructs expressing ILTV gD and IBDV VP2 (such as vHVT317 and vHVT407) or expressing ILTV gD and NDV F genes (such as vHVT308 and vHVT322) administered to chickens against ILTV challenges.

Chickens are assigned to different groups. Birds are vaccinated by the subcutaneous (SC) route with 0.2 mL of different HVT constructs. The birds from one group are left unvaccinated. Birds are challenged with ILTV by the intratracheal (IT) or the infraorbital sinus route. Birds are observed for clinical signs during 11-14 days after challenge. Birds that do not show any ILTV clinical signs (including respiratory distress associated with coughing, sneezing, rales, depression, gasping and/or bloody mucous exudates and/or death) for up to 14 days post-challenge are considered as protected.

The results show that the HVT vectors provide protection against ILTV infection.

Example 19 IBD Efficacy Induced by HVT Vectors Expressing ILTV gD and IBDV VP2

The aim of the study is to assess the efficacy of the HVT recombinant constructs expressing ILTV gD and IBDV VP2 (such as vHVT317 and vHVT407) administered to chickens against IBD challenges.

Chickens are assigned to different groups. Birds are vaccinated by the subcutaneous (SC) route with 0.2 mL of different HVT constructs. The birds from one group are left unvaccinated. Birds are challenged with IBD by the intraocular (TO) route. Birds are observed for clinical signs during 4 to 10 days after challenge. Birds that do not show any IBD clinical signs (including depression and/or death) and that do not show bursal lesions and/or atrophy for up to 10 days post-challenge are considered as protected.

The results show that the HVT vectors provide protection against IBD infection.

Example 20 NDV Efficacy Induced by HVT Vectors Expressing ILTV gD and NDV F

The aim of the study is to assess the efficacy of the HVT recombinant constructs expressing ILTV gD and NDV F genes (such as vHVT308 and vHVT322) administered to chickens against NDV challenges.

Chickens are assigned to different groups. Birds are vaccinated by the subcutaneous (SC) route with 0.2 mL of different HVT constructs. The birds from one group are left unvaccinated. Birds are challenged with NDV by the intramuscular (IM) route. Birds are observed for clinical signs during 14 days after challenge. Birds that do not show any ND clinical signs (including central nervous, or respiratory signs and/or death) for up to 14 days post-challenge are considered as protected.

The results show that the HVT vectors provide protection against NDV infection.

Example 21 IBD Efficacy Induced by vHVT316 & vHVT317 Against a Standard IBDV Challenge at D28 in SPF Chicks The aim of the study was to assess the efficacy of two HVT recombinant constructs (vHVT316 & vHVT317) expressing either the IBDV VP2 gene and NDV F gene (vHVT316) or the IBDV VP2 gene and ILTV gD gene (vHVT317) administered to one-day-old SPF chickens against standard IBDV challenge performed at D28.

One-day-old specific pathogen free (SPF) chicks were assigned to 3 groups as shown in Table 24. All birds from groups 1 & 2 (15 birds/group) were vaccinated by the subcutaneous (SC) route with 0.2 mL of vHVT316 & vHVT317 at the dose indicated. The 15 birds from group 3 were left unvaccinated. Twenty eight days after vaccination (at D28), all birds were challenged with the infectious bursal disease virus (IBDV) classical STC strain by the intraocular (TO) route ($10^{2.0}$ EID50 in 0.03 mL/bird). Four days post-challenge (at D32), all birds were terminated and necropsied to examine for gross bursal lesions.

Results of protection are shown in Table 24. 100% and 80% protection were induced by vHVT316 and vHVT317, respectively; however, the dose administered of vHVT317 was nearly 3 times lower than that of vHVT316.

TABLE 24

IBD efficacy induced by HVT-IBD + ND (vHVT316) and HVT-IBD + ILT (vHVT317) double constructs in SPF chicks after challenge at D 28 with STC IBDV strain

| Group | Vaccine | Dose (PFU) | IBD STC protection after D 28 challenge (infected/total) |
|---|---|---|---|
| 1 | vHVT316 | 2910 | 100% (0/15) |
| 2 | vHVT317 | 1030 | 80.0% (3/15) |
| 3 | — | — | 6.7% (14/15) |

Example 22 IBD Efficacy Induced by vHVT310, vHVT316 & vHVT317 in SPF Chicks after Variant IBD Challenge at D28

The aim of the study was to assess the efficacy of three HVT recombinant constructs (vHVT310, vHVT316 & vHVT317) expressing either the IBDV VP2 gene and NDV F gene (vHVT310 & vHVT316) or the IBDV VP2 gene and ILTV gD gene (vHVT317) administered to one-day-old SPF chickens against variant IBDV challenge performed at D28.

One-day-old specific pathogen free (SPF) chicks were assigned to 5 groups as shown in Table 25. All birds from groups 1 to 3 (15 birds/group) were vaccinated by the subcutaneous (SC) route with 0.2 mL of vHVT310, vHVT316 & vHVT317 at the dose indicated. Birds from group 4 and group 5 (15 birds/group) were left unvaccinated. At D28, all birds from groups 1 to 4 were challenged with the infectious bursal disease virus (IBDV) variant Delaware E strain by the intraocular (TO) route ($10^{3.0}$ EID50 in 0.03 mL/bird). Birds from group 5 were left unchallenged. At D39, body weight and bursal weight of all birds were measured. The B/B wt. ratios (bursa weight/body weight ratio×100) were calculated for all groups.

Results of protection are shown in Table 25. Protection was observed in all vaccinated groups. Protection with vHVT317 was slightly higher than that induced by vHVT310 and vHVT316 despite its lower dose.

TABLE 25

| IBD efficacy induced by different HVT constructs with double inserts in SPF chicks after challenge at D 28 with variant E IBDV strain | | | | | |
|---|---|---|---|---|---|
| Group | Vaccine | Dose (PFU) | Number of birds | IBDV challenge at D 28 | Mean B/B wt. ratio |
| 1 | vHVT310 | 2260 | 15 | Yes | 0.34 |
| 2 | vHVT316 | 2910 | 15 | Yes | 0.33 |
| 3 | vHVT317 | 1030 | 15 | Yes | 0.40 |
| 4 | — | — | 15 | Yes | 0.12 |
| 5 | — | — | 15 | No | 0.43 |

Example 23 ILT Efficacy Induced by vHVT317 Against a ILTV Challenge at D28 in SPF Chicks The aim of the study was to assess the efficacy of the vHVT317 recombinant construct expressing the IBDV VP2 gene and the ILTV gD gene administered to one-day-old SPF chickens against an ILTV challenge performed on D28.

Thirty six one-day-old SPF chicks (white Leghorn) were assigned to 2 groups as shown in Table 26. All birds (about 18 birds/group) were either vaccinated by the subcutaneous (SC) route with 0.2 mL of vHVT317 or left unvaccinated. Twenty eight days after vaccination (at D28), all birds were challenged with the ILT-96-3 ILTV strain by the intratracheal (IT) route ($10^{3.0}$ EID50 in 0.2 mL/bird). The birds were observed for clinical signs and mortality at D32, D36 & D39. Clinical signs included breathing pattern, conjunctivitis, depression and mortality. On Study Day 32, all the remaining birds were terminated. Evaluation of protection was used using 3 different criteria: (1) Any bird exhibiting any clinical signs for three consecutive days or that died after challenge is considered as ILT positive; (2) Any bird exhibiting any moderate or severe clinical signs in any category for any day or that died after challenge is considered as ILT positive; and (3) Any bird exhibiting any moderate or severe clinical signs in any category for two consecutive days or that died after challenge is considered as ILT positive.

Results of protection based on the 3 different criteria are shown in Table 26. The ILT challenge was severe since it killed (or birds were euthanized when they show very severe clinical signs for ethical reason) 86.7% of non-vaccinated birds. High levels of ILT protection were induced by vaccination with vHVT317 in these challenge conditions.

TABLE 26

| ILT efficacy induced by vHVT317 construct in SPF chicks after challenge at D 28 with ILT-96-3 ILTV strain | | | | | |
|---|---|---|---|---|---|
| Group | Vaccine | Dose (PFU) | Number of birds | % Mortality | % Protection based on criteria 1/2/3 |
| 1 | vHVT317 | 1030 | 15 | 0% | 100%/86.7%/100% |
| 2 | — | — | 15 | 86.7% | 6.7%/6.7%/6.7% |

Example 24 ILT Efficacy Induced by vHVT317, a Commercial HVT-ILT and a Commercial Chicken Embryo Origin (CEO) Vaccine Against an ILTV Challenge at D21 in Broiler Chicks The aim of the study was to assess the efficacy of vHVT317 recombinant construct expressing the IBDV VP2 gene and the ILTV gD gene administered to one-day-old broiler chickens compared to a commercial HVT-ILT vaccine (INNOVAX® ILT, Merck Animal Health) against an ILTV challenge performed on D28.

Fifty one one-day-old commercial broiler chicks were assigned to 3 groups as shown in Table 27. All birds (17 birds/group) were either vaccinated by the subcutaneous (SC) route with 0.2 mL of vHVT317 or INNOVAX® ILT (used as a positive control) at the dose indicated or left unvaccinated. At D26, the number of birds per group was reduced to 15 and each bird was weighed. Twenty eight days after vaccination (at D28), all birds were challenged with the 63140 ILTV strain by the infraorbital route ($10^{4.3}$ EID50 in 0.2 mL/bird). On Study Days 31 to 35, and Study Day 38, all birds were individually observed for clinical signs. On Study Day 38, all the remaining birds were individually weighed and terminated. Evaluation of protection was performed using 3 different criteria: (1) Any bird exhibiting any clinical signs for three consecutive days or that died after challenge is considered as ILT positive; (2) Any bird exhibiting any moderate or severe clinical signs in any category for any day or that died after challenge is considered as ILT positive; and (3) Any bird exhibiting any moderate or severe clinical signs in any category for two consecutive days or that died after challenge is considered as ILT positive. The body weight was also compared at D26 and D38.

Results of protection using the 3 criteria are shown in Table 27. All controls were considered non-protected for the 3 criteria. Both tested vaccines induced high and similar ILT protection. There were no significant difference between body weight at D26 (before challenge); however, after challenge, body weights of vaccinated birds were significantly ($p<0.0001$) higher than those of non-vaccinated birds indicating protection against weight loss.

TABLE 27

| ILT efficacy induced by vHVT317 and INNOVAX ILT (positive control) constructs in broiler chicks after challenge at D 28 with 63140 ILTV strain | | | | | | |
|---|---|---|---|---|---|---|
| Group | Vaccine | Dose (PFU) | Number of birds | % Protection based on criteria 1/2/3 | Body weight at D 26* | Body weight at D 38* |
| 1 | vHVT317 | 3820 | 15 | 86.7%/86.7%/86.7% | 1544 ± 61 | 2931 ± 63 |
| 1 | INNOVAX | 3700 | 15 | 100%/93.3%/93.3% | 1491 ± 61 | 2839 ± 61 |
| 2 | — | — | 15 | 0%/0%/0% | 1461 ± 61 | 2433 ± 63 |

*mean ± standard deviation in g

Example 25 IBD Efficacy Induced by the in Ovo Administration of vHVT317 after Variant IBD Challenge at 28 Day-of-Age in SPF Chicks The aim of the study was to assess the efficacy of vHVT317 expressing the IBDV VP2 gene and ILTV gD gene administered in ovo to 18-19 day-old embryos from SPF chickens against variant IBDV challenge performed at 28 day-of-age (31 days post-vaccination).

18-19 day-old embryos from specific pathogen free (SPF) chickens were assigned to 3 groups as shown in Table 28. All birds from groups 1 & 2 (about 30 eggs/group) were vaccinated by the in ovo (SC) route with 0.05 mL of vHVT317 at the dose indicated. Embryonated eggs from group 3 were sham-inoculated with 0.05 mL of Marek's vaccine diluent. At hatch, 22 chicks per group were kept and, before challenge, all 3 groups were reduced to 20 birds. Thirty one days after vaccination (at 28 day-of-age), birds from all 3 groups were challenged with the infectious bursal disease virus (IBDV) variant Delaware E strain by the intraocular (TO) route (target dose of $10^{3.0}$ EID50 in 0.03 mL/bird). Birds from group 5 were sham challenged with TPB (tryptose phosphate broth, 0.03 mL/bird). Eleven days post-challenge, body weight and bursal weight of all birds were measured. The B/B wt. ratios (bursa weight/body weight ratio×100) were calculated for all groups.

Results of protection are shown in Table 28. A clear bursal atrophy was observed in all non-vaccinated challenged birds. Protection was observed in vHVT317-vaccinated groups at the 2 tested doses.

TABLE 28

IBD efficacy induced by vHVT317 administered in ovo after challenge at 28 day-of-age with variant E IBDV strain in SPF chicks

| Group | Vaccine | Dose (PFU) | Number of birds | IBDV challenge | Mean B/B wt. ratio |
|---|---|---|---|---|---|
| 1 | vHVT317 | 2250 | 20 | Yes | 0.41 |
| 2 | vHVT317 | 3225 | 20 | Yes | 0.60 |
| 3 | — | — | 20 | Yes | 0.13 |
| 4 | — | — | 20 | No | 0.69 |

Example 26 ILT Efficacy Induced by vHVT317 Administered by the in Ovo Route Against a ILTV Challenge at D28 in SPF Chicks The aim of the study was to assess the efficacy of the vHVT317 recombinant construct expressing the IBDV VP2 gene and the ILTV gD gene administered by the in ovo route to 18-19 day-old embryos against an ILTV challenge performed on D28 (at 25 day-of-age) in SPF chickens.

18-19 day-old embryos from specific pathogen free (SPF) chickens were assigned to 2 groups as shown in Table 29. All birds from groups 1 (about 30 eggs/group) were vaccinated by the in ovo (SC) route with 0.05 mL of vHVT317 at the dose indicated. Embryonated eggs from group 2 were sham-inoculated with 0.05 mL of Marek's vaccine diluent. At hatch, 22 chicks per group were kept and, one day before challenge, both groups were reduced to 20 birds. Twenty five days after vaccination (at D28), birds from both groups were challenged with the 63140 ILTV strain administered in the infraorbital sinus ($10^{47}$ EID50 in 0.2 mL/bird). The birds were observed for clinical signs and mortality on D28 to D38. On Study Day 38, all the remaining birds were terminated. Efficacy against ILT challenge was determined by the absence of typical ILT clinical signs such as: depression, respiratory distress associated with coughing, sneezing, rales, gasping with extended neck, with or without bloody and/or mucous discharge; dyspnea and mouth breathing; infra-orbital sinuses swelling, with or without drainage; and/or swollen conjunctiva with partial or complete closure of the eyes. Any mortality post-challenge, except due to trauma, or any clear condition that excludes the bird from the study, were considered positive for ILT.

Results of ILT protection are shown in Table 29. The results showed that most vHVT317 vaccinated birds were protected.

TABLE 29

ILT efficacy induced by vHVT317 administered by the in ovo route after infraorbital sinus challenge at D 28 with 63140 ILTV strain in SPF chicks

| Group | Vaccine | Dose (PFU) | Number of birds | % Protection (number protected/total) |
|---|---|---|---|---|
| 1 | vHVT317 | 2300 | 20 | 85% (17/20) |
| 2 | — | — | 20 | 5% (1/20) |

Example 29 ND Efficacy Induced by vHVT309 & vHVT310 Against a Velogenic NDV Challenge at D21 in SPF Chickens The aim of the study was to assess the efficacy of two HVT recombinant constructs (vHVT309 & vHVT310) expressing the IBDV VP2 gene and NDV F gene administered to one-day-old SPF chickens against velogenic NDV challenge performed on D21.

One-day-old SPF chicks (white leghorn) were assigned to 3 groups of birds as shown in Table 30. All birds from groups 2 and 3 were vaccinated by the subcutaneous (SC) route with 0.2 mL of vHVT309 (14 birds; group 2) or vHVT310 (15 birds; group 3) at a target dose of 2000 PFU. Birds from group 1 (5 birds) were left unvaccinated. Two birds of group 2 died on D5 for unknown reason. Twenty one days after vaccination (at D21), the blood of 10 birds from group 3 was collected for serology; then, all birds from all 3 groups were challenged with the velogenic NDV Herts 33 strain by the intramuscular (IM) route ($10^{5.0}$ EID50 in 0.2 mL/bird). All birds were observed for clinical signs during 14 days post-challenge. Birds were considered as protected if they did not die or show ND clinical signs.

Results of protection are summarized in Table 30. All non-vaccinated birds of group 1 died after challenge; all vaccinated birds were protected. The vHVT310 construct induced significant anti-NDV (mean of 3.7±0.3 (standard deviation) log 10 by ELISA (ID Screen Newcastle Disease Indirect kit from ID-VET) and mean of 3.9±0.7 log 2 by HI test) and anti-IBDV (mean of 3.7 log 10±0.2 log 10 by ELISA (ProFLOK IBD Plus ELISA kit from Zoetis) antibodies in all the 10 G3-bird serums sampled on D21.

TABLE 30

ND efficacy induced by different HVT-IBD + ND double constructs in broiler chicks after challenge at D 21 with velogenic NDV strain

| Group | Vaccine | Dose (PFU) | Number of birds | Number of Dead & sick birds | Protection |
|---|---|---|---|---|---|
| 1 | — | — | 5 | 5 & 0 | 0% |
| 2 | vHVT309 | 2000 | 12 | 0 & 0 | 100% |
| 3 | vHVT310 | 2000 | 15 | 0 & 0 | 100% |

Example 28 IBD Efficacy Induced by vHVT309 and vHVT310 Against a Classical IBDV Challenge at D21 in SPF Chicks The aim of the study was to assess the efficacy of two HVT recombinant constructs (vHVT309 & vHVT310) expressing the IBDV VP2 gene and NDV F gene administered to one-day-old SPF chickens against a classical IBDV challenge performed on D21.

One-day-old SPF chicks (white Leghorn) were assigned to 3 groups as shown in Table 31. All birds from groups 2 & 3 (about 15 birds/group) were vaccinated by the subcutaneous (SC) route with 0.2 mL of vHVT309 (group 2) or vHVT310 (group 3) construct at a target dose of 2000 PFU. Ten birds from group 1 were left unvaccinated. Two unspecific early deaths were recorded in group 2. Twenty one days after vaccination (at D21), all birds were challenged with the classical 52/70 Faragher IBDV strain by the intraocular (TO) route ($10^{2.0}$ EID50 in 0.05 mL/bird). Eleven days post-challenge (at D32) all birds were terminated and necropsied to examine for gross bursal lesions. Bursal and body were weighted to calculate the bursal on body weight ratio. The bursa was then stored in formaldehyde for histology. Histological lesions of the bursa were scored according to the scale presented in Table 32. The severity of the challenge was validated if (1) at least 50% of the challenge controls died or showed characteristic signs of the disease, especially apathy/ruffled feathers during more than 2 days or prostration, and (2) 100% of the surviving challenge controls showed histology scores of the Bursa of Fabricius ≥3. The efficacy of the vaccine candidates was demonstrated if at least 90% of the chickens were protected. The chickens were considered protected if (1) they survived and did not show notable clinical signs of the disease, especially no apathy/ruffled feathers during more than 2 days or absence of prostration, and (2) they showed a histology score of the Bursa of Fabricius <3.

Results of protection are shown in Table 31. All controls were positive for IBD infection. Complete IBD protection was induced by vaccination with vHVT309 or vHVT310.

TABLE 31

IBD efficacy induced by two HVT constructs expressing two genes in SPF chicks after challenge at D 21 with Faragher IBDV strain

| Group | Vaccine | Dose (log10 PFU) | Clinical signs #dead/ #sick/total | Mean Bursal/body weight ratio (*1000) | Protection |
|---|---|---|---|---|---|
| 1 | — | — | 4/1/10 | 1.7 ± 0.6** | 0% |
| 2 | vHVT309 | 3.3 | 0/0/14 | 5.4 ± 1.2 | 100% |
| 3 | vHVT310 | 3.3 | 0/0/15 | 5.5 ± 0.7 | 100% |

**mean ± standard deviation

TABLE 32

Scoring scale of histological lesions of the bursa of Fabricius*

| Score | Histology observation/lesions |
|---|---|
| 0 | No lesion, normal bursa |
| 1 | 1% to 25% of the follicles show lymphoid depletion (i.e. less than 50% of depletion in 1 affected follicle), influx of heterophils in lesions |
| 2 | 26% to 50% of the follicles show nearly complete lymphoid depletion (i.e. more than 75% of depletion in 1 affected follicle), affected follicles show necrosis and severe influx of heterophils may be detected |
| 3 | 51% to 75% of the follicles show lymphoid depletion; affected follicles show necrosis lesions and a severe influx of heterophils is detected |
| 4 | 76% to 100% of the follicles show nearly complete lymphoid depletion; hyperplasia and cyst structures are detected; affected follicles show necrosis and severe influx of heterophils is detected |
| 5 | 100% of the follicles show nearly complete lymphoid depletion; complete loss of follicular structure, thickened and folded epithelium, fibrosis of bursal tissue |

*sourced from Monograph No. 04/2013: 0587 of European Pharmacopoeia "Avian Infectious Bursal Disease vaccine (live)

Example 29 Impact of in Ovo Administration of vHVT317 on Hatchability of SPF Chicks The aim of the study was to assess the safety of vHVT317 on hatchability when administered by the in ovo route.

The results are a compilation of data from several studies including those described in examples 23, 24, 25, and 26. Embryonated eggs at 18-19 days of incubation were inoculated either with vHVT317 at a target dose of 2000 or 3000 PFU or with Marek's disease vaccine diluent. The percentage of hatchability was evaluated for each group. Results are summarized in Table 33 and showed excellent levels of hatchability in vaccinated eggs.

TABLE 33

Hatchability after in ovo administration of vHVT317

| Group | Vaccine | Target Dose (PFU) | Number of vaccinated eggs | Number of eggs hatched | % hatchability |
|---|---|---|---|---|---|
| 1 | Diluent | — | 150 | 149 | 99.3% |
| 2 | vHVT317 | 2000 | 139 | 135 | 97.1% |
| 3 | vHVT317 | 3000 | 80 | 78 | 97.5% |

Example 30 ILT Efficacy Induced by vHVT406 Against ILTV Challenges

Example 30.1 ILT Efficacy Induced by vHVT406 Against an ILTV Challenge at D28

The aim of the study is to assess and compare the efficacy of vHVT406 recombinant construct expressing the ILTV gD gene and a commercial HVT-ILT vectored vaccine against ILT challenge.

Twelve (12) one-day-old SPF birds were assigned to each group. The birds in Groups 1-2 were vaccinated SQ with 0.2 ml per bird. After vaccination, all birds were placed into their respective units. On Day 28, all birds were challenged via the intratracheal (IT) route with Infectious Laryngotracheitis Virus (ILT), ILT-93-3 EP2. All birds were observed for 11 days post-challenge for clinical signs due to the challenge. On Day 32, tracheal and conjunctival swabs were collected from all remaining birds. Swabs were processed for q-PCR analysis. On Day 39, all remaining birds were terminated.

Results are shown in Table 34 below. The results showed that all vHVT406 vaccinated birds were protected. Surprisingly, the results also showed that good protection (100% protection) was achieved in vHVT406 group when lower dose (6,960 pfu/0.2 ml) was used when compared to the higher dose (10,340 pfu/0.2 ml) used for the commercial product Innovax HVT-ILT.

TABLE 34

Number of Birds Positive for ILT and Percent Positive by Group[1]

| Group | Vaccine | Dose/SQ[2] | # Birds | # Positive/ Total # Birds | % Protection (% Infection) | % Found Dead | % Total Mortality |
|---|---|---|---|---|---|---|---|
| 1 | vHVT406 | 6,960 pfu/ 0.2 ml HVT | 11[3] | 0/11 | 100 | 0 | 0 |
| 2 | Innovax HVT-ILT[4] | 10,340 pfu/ 0.2 ml HVT | 12 | 0/12 | 100 | 0 | 0 |

[1]Birds were considered positive if they showed clinical signs for three consecutive days, including mortality or mortality after swabbing.

[2]Plaque forming units (pfu)-Subcutaneous administration (SQ); 0.20 ml per dose.

[3]One bird in vHVT406 group was excluded from the study due to paralysis.

[4]Commercial product of MSD Animal Health

Example 30.2 ILT Efficacy Induced by vHVT406 Against an ILTV Challenge at D21

The goal of the study is to assess and compare the efficacy of the vHVT406 and two commercial HVT-ILT vectored vaccines against ILT challenge.

Twelve (12) one-day-old SPF birds were assigned to each group. The randomization also assigned the isolation units where the birds were placed (12 birds per unit, one unit per group). Birds in Groups 1-3 were vaccinated SQ with 0.2 ml per bird. On Day 21, all birds in Groups 1-2 were challenged via the intratracheal (IT) route with Infectious Laryngotracheitis Virus (ILT), ILT-96-3 EP2. The birds were observed for 11 days post-challenge for clinical signs due to the challenge. On Day 25, tracheal and conjunctival swabs were collected on all remaining birds. Swab samples were processed for q-PCR. On Day 32, all remaining birds were terminated.

Results are shown in Table 35 below. The results showed that all but one vHVT406 vaccinated birds were protected. Surprisingly, the results also showed that good protection (91.7% protection) was achieved in vHVT406 group when lower dose (810 pfu/0.2 ml) was used when compared to the higher dose (1590 pfu/0.2 ml) used for the commercial product Innovax HVT-ILT to achieve the same protection level (91.7%). Further, vHVT406 provided better protection (91.7%) when used at a lower dose than the commercial product Vectormune HVT-ILT which only provided 75% protection.

TABLE 35

Number of Birds Positive for ILT and Percent Positive by Group[1]

| Group | Vaccine | Dose/SQ[2] | # Birds | # Positive/ Total # Birds | % Protection (% Infection) | % Found Dead | % Total Mortality |
|---|---|---|---|---|---|---|---|
| 1 | vHVT406 | 810 pfu/ 0.2 ml | 12 | 1/12 | 91.7 | 0 | 0 |
| 2 | Innovax HVT-ILT | 1590 pfu/ 0.2 ml | 12 | 1/12 | 91.7 | 0 | 0 |
| 3 | Vectormune HVT-ILT[3] | 39,000 pfu/ 0.2 ml | 12 | 3/12 | 75 | 25 | 25 |

[1]Birds were considered positive if they showed clinical signs for three consecutive days, including mortality or mortality after swabbing.

[2]Plaque forming units (pfu)-Subcutaneous administration (SQ); 0.20 ml per dose.

[3]Commercial product of Ceva

Having thus described in detail preferred embodiments of the present invention, it is to be understood that the invention defined by the above examples is not to be limited to particular details set forth in the above description as many apparent variations thereof are possible without departing from the spirit or scope of the present invention.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What we claim is:

1. A vaccine comprising a recombinant herpesvirus of turkeys (HVT) vector, wherein the HVT vector comprises a first heterologous polynucleotide coding for and expressing an Infectious Bursal Disease Virus (IBDV) viral protein 2 (VP2) antigen and a second heterologous polynucleotide coding for and expressing a Newcastle Disease Virus Fusion Protein (NDV-F) antigen, wherein the IBDV VP2 antigen has at least 85% sequence identity to a polypeptide having the sequence as set forth in SEQ ID NO:2, and wherein the NDV-F antigen has at least 85% sequence identity to a polypeptide having the sequence as set forth in SEQ ID NO:5;

wherein the two heterologous polynucleotides are inserted into one locus in a non-essential region of the HVT genome selected from the group consisting of intergenic region 1 locus, intergenic region 2 locus, intergenic region 3 locus, UL43 locus, US10 locus, US2 locus, and SORF3/US2 locus;

wherein the two heterologous polynucleotides are linked by internal ribosome entry site (IRES); and wherein the expression of the two heterologous polynucleotides is driven by a mouse cytomegalovirus (mCMV) immediate early (IE) promoter or human cytomegalovirus (hCMV) IE promoter.

2. The vaccine of claim 1, wherein the first heterologous polynucleotide is operably linked to mCMV IE promoter at the 5' end, and the IRES at the 3' end.

3. The vaccine of claim 1, wherein the non-essential region is the IG1 locus of the HVT genome.

4. The vaccine of claim 1, wherein the IBDV VP2 antigen has at least 90%, 95%, 96%, 97%, 98% or 99% sequence identity to a polypeptide having the sequence as set forth in SEQ ID NO:2.

5. The vaccine of claim 1, wherein the IBDV VP2 antigen has the polypeptide sequence as set forth in SEQ ID NO: 2.

6. The vaccine of claim 1, wherein the first heterologous polynucleotide encoding the IBDV VP2 antigen has at least 70%, 75%, 80%, 85%, 90%, 95%, 96%, 97%, 98% or 99% sequence identity to a polynucleotide having the sequence as set forth in SEQ ID NO:1.

7. The vaccine of claim 1, wherein the first heterologous polynucleotide encoding the IBDV VP2 antigen has the sequence as set forth in SEQ ID NO: 1.

8. The vaccines of claim 1, wherein the NDV-F antigen has at least 90%, 95%, 96%, 97%, 98% or 99% sequence identity to a polypeptide having the sequence as set forth in SEQ ID NO:5.

9. The vaccines of claim 1, wherein the NDV-F antigen has the polypeptide sequence as set forth in SEQ ID NO: 5.

10. The vaccine of claim 1, wherein the second heterologous polynucleotide encoding the NDV-F antigen has at least 70%, 75%, 80%, 85%, 90%, 95%, 96%, 97%, 98% or 99% sequence identity to a polynucleotide having the sequence as set forth in SEQ ID NO:3.

11. The vaccine of claim 1, wherein the second heterologous polynucleotide encoding the NDV-F antigen has the sequence as set forth in SEQ ID NO: 3.

12. The vaccines of claim 1, wherein the expression of the NDV-F antigen is regulated by the Simian virus 40 (SV40) poly A signal having the sequence as set forth in SEQ ID NO: 8.

13. The vaccine of claim 1, wherein the IRES has the sequence as set forth in SEQ ID NO: 10.

14. The vaccine of claim 1, wherein the first heterologous polynucleotide has the sequence as set forth in SEQ ID NO:

1, and wherein the second heterologous polynucleotide has the sequence as set forth in SEQ ID NO: 3;

wherein the non-essential region is the IG1 locus of the HVT genome;

wherein the first heterologous polynucleotide is operably linked to a mCMV IE promoter at the 5' end, and the IRES at the 3' end, and wherein the IRES has the sequence as set forth in SEQ ID NO: 10; and wherein the expression of the NDV-F antigen is regulated by the SV40 poly A signal having the sequence as set forth in SEQ ID NO: 8.

15. The vaccine of claim 1, further comprising a pharmaceutically or veterinarily acceptable carrier, excipient, vehicle or adjuvant.

16. A method of inducing an immunological response in an animal against one or more antigens or a protective response in an animal against one or more avian pathogens, comprising inoculating the animal at least once with the vaccine of claim 15.

17. The method of claim 16, wherein the animal is an avian.

18. The method of claim 16, wherein the avian pathogen is selected from the group consisting of Newcastle Disease Virus (NDV) and Infectious Bursal Disease Virus (IBDV).

19. The method of claim 16, wherein the vaccine is administered to one-day old chicks subcutaneously or intramuscularly.

20. The method of claim 16, wherein the vaccine is administered to an avian in ovo in 17-19 day-old embryos.

* * * * *

SEQUENCE LISTING

```
Sequence total quantity: 27
SEQ ID NO: 1            moltype = DNA  length = 1359
FEATURE                 Location/Qualifiers
source                  1..1359
                        mol_type = other DNA
                        organism = synthetic construct
                        note = DNA encoding IBDV VP2
SEQUENCE: 1
atgacaaacc tgcaagatca aacccaacag attgttccgt tcatacggag ccttctgatg  60
ccaacaaccg gaccggcgtc cattccggac gacaccctgg agaagcacac tctcaggtca  120
gagacctcga cctacaattt gactgtgggg gacacagggt cagggctaat tgtctttttc  180
cctggattcc ctggctcaat tgtgggtgct cactacacac tgcagagcaa tgggaactac  240
aagttcgatc agatgctcct gactgcccag aacctaccgg ccagctacaa ctactgcaga  300
ctagtgagtc ggagtctcac agtgaggtca agcacactcc ctggtggcgt ttatgcacta  360
aacggcacca taaacgccgt gaccttccaa ggaagcctga gtgaactgac agatgttagc  420
tacaatgggt tgatgtctgc aacagccaac atcaacgaca aaattgggaa tgtcctggta  480
ggggaagggg tcactgtcct cagcctaccc acatcatatg atcttgggta tgtgaggctt  540
ggtgacccca ttcccgctat agggcttgac ccaaaaatgg tagctacatg cgacagcagt  600
gacaggccca gagtctacac cataactgca gccgatgatt accaattctc atcacagtac  660
caaccaggtg ggtaacaat cacactgttc tcagccaaca ttgatgctat cacaagcctc  720
agcattgggg gagagctcgt gtttcaaaca agcgtccaag gccttgtact gggcgccacc  780
atctacctta taggctttga tgggactgcg gtaatcacca gagctgtagc cgcagataat  840
gggctgacgg ccggcaccga caatcttatg ccattcaatc ttgtcattcc aaccaatgag  900
ataacccagc caatcacatc catcaaactg gagatagtga cctccaaaag tggtggtcag  960
gcaggggatc agatgtcatg gtcggcaagt gggagcctag cagtgacgat ccatggtggc  1020
aactatccag gggccctccg tcccgtcaca ctagtagcct acgaaagagt ggcaacagga  1080
tccgtcgtta cggtcgctgg ggtgagtaac ttcgagctga ttccaaatcc tgaactagca  1140
aagaacctgg ttacagaata cggccgattt gacccaggag ccatgaacta cacaaaattg  1200
atactgagtg agagggaccg tcttggcatc aagaccgtct ggccaacaag ggagtacact  1260
gattttcgtg agtacttcat ggaggtggcc gacctcaact ctcccctgaa gattgcagga  1320
gcatttggct tcaaagacat aatccgggct ataaggagg                          1359

SEQ ID NO: 2            moltype = AA  length = 453
FEATURE                 Location/Qualifiers
source                  1..453
                        mol_type = protein
                        organism = synthetic construct
                        note = IBDV VP2 protein
SEQUENCE: 2
MTNLQDQTQQ IVPFIRSLLM PTTGPASIPD DTLEKHTLRS ETSTYNLTVG DTGSGLIVFF  60
PGFPGSIVGA HYTLQSNGNY KFDQMLLTAQ NLPASYNYCR LVSRSLTVRS STLPGGVYAL  120
NGTINAVTFQ GSLSELTDVS YNGLMSATAN INDKIGNVLV GEGVTVLSLP TSYDLGYVRL  180
GDPIPAIGLD PKMVATCDSS DRPRVYTITA ADDYQFSSQY QPGGVTITLF SANIDAITSL  240
SIGGELVFQT SVQGLVLGAT IYLIGFDGTA VITRAVAADN GLTAGTDNLM PFNLVIPTNE  300
ITQPITSIKL EIVTSKSGGQ AGDQMSWSAS GSLAVTIHGG NYPGALRPVT LVAYERVATG  360
SVVTVAGVSN FELIPNPELA KNLVTEYGRF DPGAMNYTKL ILSERDRLGI KTVWPTREYT  420
DFREYFMEVA DLNSPLKIAG AFGFKDIIRA IRR                                453

SEQ ID NO: 3            moltype = DNA  length = 1659
FEATURE                 Location/Qualifiers
source                  1..1659
                        mol_type = other DNA
                        organism = synthetic construct
                        note = NDV-Fopt VIId of pFSV40VP2 and pFIRESVP2
SEQUENCE: 3
atgggcagca agcccagcac aagaatccca gcccccctga tgctgatcac ccgcatcatg  60
ctgatcctgg gctgcatcag acccacaagc tccctggatg gacgccccct ggccgctgcc  120
ggcatcgtgg tgaccggcga caaggccgtg aacgtgtaca ccagcagcca gaccggcagc  180
atcatcgtga agctgctgcc caacatgccc agagacaaag aggcctgcgc caaggccccc  240
ctggaagcct acaacagaac cctgaccacc ctgctgaccc ccctgggcga cagcatcaga  300
```

-continued

```
aagatccagg gctccgtgag cacaagcggc ggaggaaagc agggcagact gatcggcgcc  360
gtgatcggca gcgtggccct gggagtggct acagctgccc agattaccgc tgcagccgcc  420
ctgatccagg ccaaccagaa cgccgccaac atcctgagac tgaaagagag cattgccgcc  480
accaacgagg ccgtgcacga agtgaccgac ggcctgagcc agctgtccgt ggccgtgggc  540
aagatgcagc agttcgtgaa cgaccagttc aacaacaccg ccagagagct ggactgcatc  600
aagatcaccc agcaggtggg cgtggagctg aacctgtacc tgaccgagct gaccacagtg  660
ttcggccccc agatcacaag cccagccctg acacagctga ccatccaggc cctgtacaac  720
ctggctggcg gcaacatgga ctatctgctg acaaagctgg gaatcggcaa caaccagctg  780
tccagcctga tcggaagcgg cctgatcacc ggctacccca tcctgtacga cagccagaca  840
cagctgctgg gcatccaggt gaacctgccc agcgtgggca acctgaacaa catgcgcgcc  900
acctacctgg aaaccctgag cgtgtccacc accaagggct acgccagcgc cctggtgccc  960
aaggtggtga cacaggtggg cagcgtgatc gaggaactgg acaccagcta ctgcatcgag  1020
agcgacctgg acctgtactg caccagaatc gtgaccttcc caatgagccc cggcatctac  1080
agctgcctga gcggcaacac cagcgcctgc atgtacagca agaccgaagg cgcactgaca  1140
acaccctaca tggccctgaa gggaagcgtg atcgccaact gcaagatcac cacctgcaga  1200
tgcaccgacc ccccaggcat catcagccag aactacggcg aggccgtgag cctgatcgat  1260
cgccattcct gtaacgtgct gtccctggac ggcatcacac tgagactgag cggcgagttc  1320
gatgccacct accagaagaa catcagcatc ctggacagcc aggtgatcgt gaccggcaac  1380
ctggacatca gcaccgagct gggcaacgtg aataacagca tcagcaacgc cctggacaga  1440
ctggccgaga gcaacagcaa gctggaaaaa gtgaacgtgc gcctgacatc cacttccgct  1500
ctgatcacct acatcgtgct gaccgtgatc agcctggtgt tcggcgccct gagcctggtg  1560
ctggcctgct acctgatgta caagcagaag gcccagcaga aaccctgct gtggctgggc  1620
aacaacaccc tggaccagat gagagccacc accagagcc                         1659

SEQ ID NO: 4            moltype = DNA  length = 1659
FEATURE                 Location/Qualifiers
source                  1..1659
                        mol_type = other DNA
                        organism = synthetic construct
                        note = NDV-F wildtype VIId of pFP2AVP2
SEQUENCE: 4
atgggctcca aaccttctac caggatccca gcacctctga tgctgatcac ccggattatg  60
ctgatattgg gctgtatccg tccgacaagc tctcttgacg gcaggcctct tgcagctgca  120
ggaattgtag taacaggaga taaggcagtc aatgtataca cttcgtctca gacagggtca  180
atcatagtca agttgctccc gaatatgccc agggataagg aggcgtgtgc aaaagcccca  240
ttagaggcat ataacagaac actgactact ttgctcactc ctcttggcga ctccatccgc  300
aagatccaag ggtctgtgtc cacatctgga ggaggcaagc aaggccgcct gataggtgct  360
gttattggca gtgtagctct tggggttgca acagcggcac agataacagc agctgcggcc  420
ctaatacaag ccaaccagaa tgccgccaac atcctccggc ttaaggagag cattgctgca  480
accaatgaag ctgtgcatga agtcaccgac ggattatcac aactatcagt ggcagttggg  540
aagatgcagc agtttgtcaa tgaccagttt aataatacgg cgcgagaatt ggactgtata  600
aaaatcacac aacaggttgg tgtagaactc aacctatacc taactgaatt gactacagta  660
ttcgggccac agatcacctc ccctgcatta actcagctga ccatccaggc actttataat  720
ttagctggtg gcaatatgga ttacttatta actaagttag gtatagggaa caatcaactc  780
agctcgttaa ttggtagcgg cctgatcact ggttacccta tactgtatga ctcacagact  840
caactcttgg gcatacaagt gaatttaccc tcagtcggga acttaaataa tatgcgtgcc  900
acctatttgg agaccttatc tgtaagtaca accaaaggat atgcctcagc acttgtcccg  960
aaagtagtga cacaagtcgg ttccgtgata gaagagcttg acacctcata ctgtatagag  1020
tccgatctgg atttatattg tactagaata gtgacattcc ccatgtcccc aggtatttat  1080
tcctgtttga gcggcaacac atcagcttgc atgtattcaa agactgaagg cgcactcact  1140
acgccgtata tggcccttaa aggctcagtt attgccaatt gtaaaataac aacatgtaga  1200
tgtacagacc ctcctggtat catatcgcaa aattatggag aagctgtatc cctgatagat  1260
agacattcgt gcaatgtctt atcattagac gggataactc taaggctcag tggggaattt  1320
gatgcaactt atcaaaagaa catctcaata ctagattctc aagtcatcgt gacaggcaat  1380
cttgatatat caactgaact tggaaacgtc aacaattcaa tcagcaatgc cttggatagg  1440
ttggcagaaa gcaacagcaa gctagaaaaa gtcaatgtca gactaaccag cacatctgct  1500
ctcattacct atattgttct aactgtcatt tctctagttt tcggtgcact tagtctggtg  1560
ttagcgtgtt acctgatgta caaacagaag gcacaacaaa agaccttgct atggcttggg  1620
aataataccc tcgatcagat gagagccact acaagagca                         1659

SEQ ID NO: 5            moltype = AA  length = 553
FEATURE                 Location/Qualifiers
source                  1..553
                        mol_type = protein
                        organism = synthetic construct
                        note = NDV-F VIId
SEQUENCE: 5
MGSKPSTRIP APLMLITRIM LILGCIRPTS SLDGRPLAAA GIVVTGDKAV NVYTSSQTGS  60
IIVKLLPNMP RDKEACAKAP LEAYNRTLTT LLTPLGDSIR KIQGSVSTSG GGKQGRLIGA  120
VIGSVALGVA TAAQITAAAA LIQANQNAAN ILRLKESIAA TNEAVHEVTD GLSQLSVAVG  180
KMQQFVNDQF NNTARELDCI KITQQVGVEL NLYLTELTTV FGPQITSPAL TQLTIQALYN  240
LAGGNMDYLL TKLGIGNNQL SSLIGSGLIT GYPILYDSQT QLLGIQVNLP SVGNLNNMRA  300
TYLETLSVST TKGYASALVP KVVTQVGSVI EELDTSYCIE SDLDLYCTRI VTFPMSPGIY  360
SCLSGNTSAC MYSKTEGALT TPYMALKGSV IANCKITTCR CTDPPGIISQ NYGEAVSLID  420
RHSCNVLSLD GITLRLSGEF DATYQKNISI LDSQVIVTGN LDISTELGNV NNSISNALDR  480
LAESNSKLEK VNVRLTSTSA LITYIVLTVI SLVFGALSLV LACYLMYKQK AQQKTLLWLG  540
NNTLDQMRAT TRA                                                     553

SEQ ID NO: 6            moltype = DNA  length = 1391
```

```
FEATURE                Location/Qualifiers
source                 1..1391
                       mol_type = other DNA
                       organism = synthetic construct
                       note = mCMV IE promoter
SEQUENCE: 6
aactccgccc gttttatgac tagaaccaat agtttttaat gccaaatgca ctgaaatccc  60
ctaatttgca aagccaaacg cccccctatgt gagtaatacg gggacttttt acccaatttc  120
ccaagcggaa agccccctaa tacactcata tggcatatga atcagcacgg tcatgcactc  180
taatggcggc ccatagggac tttccacata gggggcgttc accatttccc agcatagggg  240
tggtgactca atggccttta cccaagtaca ttgggtcaat gggaggtaag ccaatgggtt  300
tttcccatta ctggcaagca cactgagtca aatgggactt tccactgggt tttgcccaag  360
tacattgggt caatgggagg tgagccaatg ggaaaaaccc attgctgcca agtacactga  420
ctcaataggg actttccaat gggtttttcc attgttggca agcatataag gtcaatgtgg  480
gtgagtcaat agggactttc cattgtattc tgcccagtac ataaggtcaa tagggggtga  540
atcaacagga aagtcccatt ggagccaagt acactgcgtc aatagggact ttccattggg  600
ttttgcccag tacataaggt caataggggga tgagtcaatg ggaaaaaccc attggagcca  660
agtacactga ctcaataggg actttccatt gggttttgcc cagtacataa ggtcaatagg  720
gggtgagtca acaggaaagt cccattggag ccaagtacat tgagtcaata gggactttcc  780
aatgggtttt gcccagtaca taaggtcaat gggaggtaag ccaatgggtt tttcccatta  840
ctggcacgta tactgagtca ttagggactt tccaatgggt tttgcccagt acataaggtc  900
aatagggggtg aatcaacagg aaagtcccat tggagccaag tacactgagt caatagggac  960
tttccattgg gttttgccca gtacaaaagg tcaatagggg gtgagtcaat gggtttttcc  1020
cattattggc acgtacataa ggtcaatagg ggtgagtcat tgggtttttc cagccaattt  1080
aattaaaacg ccatgtactt tcccaccatt gacgtcaatg ggctattgaa actaatgcaa  1140
cgtgaccttt aaacggtact ttcccatagc tgattaatgg gaaagtaccg ttctcgagcc  1200
aatacacgtc aatgggaagt gaaagggcag ccaaaacgta acaccgcccc ggttttcccc  1260
tggaaattcc atattggcac gcattctatt ggctgagctg cgttctacgt gggtataaga  1320
ggcgcgacca gcgtcggtac cgtcgcagtc ttcggtctga ccaccgtaga acgcagagct  1380
cctcgctgca g                                                       1391

SEQ ID NO: 7           moltype = DNA  length = 345
FEATURE                Location/Qualifiers
source                 1..345
                       mol_type = other DNA
                       organism = synthetic construct
                       note = SV40 Promoter for NDV F
SEQUENCE: 7
gctgtggaat gtgtgtcagt tagggtgtgg aaagtcccca ggctccccag caggcagaag  60
tatgcaaagc atgcatctca attagtcagc aaccaggtgt ggaaagtccc caggctcccc  120
agcaggcaga agtatgcaaa gcatgcatct caattagtca gcaaccatag tcccgcccct  180
aactccgccc atcccgcccc taactccgcc cagttccgcc cattctccgc cccatggctg  240
actaattttt tttatttatg cagaggccga ggccgcctcg gcctctgagc tattccagaa  300
gtagtgagga ggcttttttg gaggcctagg cttttgcaaa aagct                  345

SEQ ID NO: 8           moltype = DNA  length = 199
FEATURE                Location/Qualifiers
source                 1..199
                       mol_type = other DNA
                       organism = synthetic construct
                       note = SV40 Poly A
SEQUENCE: 8
ggggatccag acatgataag atacattgat gagtttggac aaaccacaac tagaatgcag  60
tgaaaaaaat gctttatttg tgaaatttgt gatgctattg ctttatttgt aaccattata  120
agctgcaata aacaagttaa caacaacaat tgcattcatt ttatgtttca ggttcagggg  180
gaggtgtggg aggtttttt                                               199

SEQ ID NO: 9           moltype = DNA  length = 154
FEATURE                Location/Qualifiers
source                 1..154
                       mol_type = other DNA
                       organism = synthetic construct
                       note = Synthetic Poly A
SEQUENCE: 9
aataaaatat ctttattttc attacatctg tgtgttggtt ttttgtgtga atcgatagta  60
ctaacatacg ctctccatca aaacaaaacg aaacaaaaca aactagcaaa ataggctgtc  120
cccagtgcaa gtgcaggtgc cagaacattt ctct                              154

SEQ ID NO: 10          moltype = DNA  length = 563
FEATURE                Location/Qualifiers
source                 1..563
                       mol_type = other DNA
                       organism = synthetic construct
                       note = IRES of pFIRESVP2
SEQUENCE: 10
cccccccccc taacgttact ggccgaagcc gcttggaata aggccggtgt gcgtttgtct  60
atatgttatt ttccaccata ttgccgtctt ttggcaatgt gagggcccgg aaacctggcc  120
ctgtcttctt gacgagcatt cctaggggtc tttcccctct cgccaaagga atgcaaggtc  180
tgttgaatgt cgtgaaggaa gcagttcctc tggaagcttc ttgaagacaa acaacgtctg  240
```

```
tagcgaccct ttgcaggcag cggaaccccc cacctggcga caggtgcctc tgcggccaaa  300
agccacgtgt ataagataca cctgcaaagg cggcacaacc ccagtgccac gttgtgagtt  360
ggatagttgt ggaaagagtc aaatggctct cctcaagcgt attcaacaag gggctgaagg  420
atgcccagaa ggtaccccat tgtatgggat ctgatctggg gcctcggtgc acatgcttta  480
catgtgttta gtcgaggtta aaaaacgtct aggccccccg aaccacgggg acgtggtttt  540
cctttgaaaa acacgatgat aat                                          563

SEQ ID NO: 11          moltype = DNA  length = 66
FEATURE                Location/Qualifiers
source                 1..66
                       mol_type = other DNA
                       organism = synthetic construct
                       note = P2A of pFP2AVP2
SEQUENCE: 11
ggctccggcg ccaccaactt ctccctgctc aagcaggccg gcgacgtgga ggagaaccct  60
ggacct                                                             66

SEQ ID NO: 12          moltype = DNA  length = 3807
FEATURE                Location/Qualifiers
source                 1..3807
                       mol_type = other DNA
                       organism = synthetic construct
                       note = pFSV40VP2 for vHVT309
misc_feature           1..1362
                       note = IBDV VP2
misc_feature           1383..1594
                       note = SV40 Poly A
misc_feature           1624..1968
                       note = SV40 Promoter
misc_feature           1981..3645
                       note = NDV-Fopt VIId
misc_feature           3654..3807
                       note = Synthetic Poly A
SEQUENCE: 12
atgacaaacc tgcaagatca aacccaacag attgttccgt tcatacggag ccttctgatg  60
ccaacaaccg gaccggcgtc cattccggac gacaccctgg agaagcacac tctcaggtca  120
gagacctcga cctacaattt gactgtgggg gacacagggt cagggctaat tgtctttttc  180
cctggattcc ctggctcaat tgtgggtgct cactacacac tgcagagcaa tgggaactac  240
aagttcgatc agatgctcct gactgcccag aacctaccgg ccagctacaa ctactgcaga  300
ctagtgagtc ggagtctcac agtgaggtca agcacactcc ctggtggcgt ttatgcacta  360
aacggcacca taaacgccgt gaccttccaa ggaagcctga gtgaactgac agatgttagc  420
tacaatgggt tgatgtctgc aacagccaac atcaacgaca aaattgggaa tgtcctggta  480
ggggaagggg tcactgtcct cagcctaccc acatcatatg atcttgggta tgtgaggctt  540
ggtgacccca ttcccgctat agggcttgac ccaaaaatgg tagctacatg cgacagcagt  600
gacaggccca gagtctacac cataactgca gccgatgatt accaattctc atcacagtac  660
caaccaggtg ggtaacaat cacactgttc tcagccaaca ttgatgctat cacaagcctc  720
agcattgggg gagagctcgt gtttcaaaca agcgtccaag gccttgtact gggcgccacc  780
atctacctta taggctttga tgggactgcg gtaatcacca gagctgtagc cgcagataat  840
gggctgacgg ccggcaccga caatcttatg ccattcaatc ttgtcattcc aaccaatgag  900
ataacccagc caatcacatc catcaaactg gagatagtga cctccaaaag tggtggtcag  960
gcaggggatc agatgtcatg gtcggcaagt gggagcctag cagtgacgat ccatggtggc  1020
aactatccag gggccctccg tcccgtcaca ctagtagcct acgaaagagt ggcaacagga  1080
tccgtcgtta cggtcgctgg ggtgagtaac ttcgagctga ttccaaatcc tgaactagca  1140
aagaacctgg ttacagaata cggccgattt gacccaggag ccatgaacta cacaaaattg  1200
atactgagtg agagggaccg tcttggcatc aagaccgtct ggccaacaag ggagtacact  1260
gattttcgtg agtacttcat ggaggtggcc gacctcaact ctcccctgaa gattgcagga  1320
gcatttggct tcaaagacat aatccgggct ataaggaggt aagcttgatc tagagcggcc  1380
gcggggatcc agacatgata agatacattg atgagtttgg acaaaccaca actagaatgc  1440
agtgaaaaaa atgctttatt tgtgaaattt gtgatgctat tgctttattt gtaaccatta  1500
taagctgcaa taaacaagtt aacaacaaca attgcattca ttttatgttt caggttcagg  1560
gggaggtgtg ggaggttttt tcggatcctc tagagtcgac gaattcgagc tcggtacagc  1620
ttggctgtgg aatgtgtgtc agttagggtg tggaaagtcc ccaggctccc cagcaggcag  1680
aagtatgcaa agcatgcatc tcaattagtc agcaaccagg tgtggaaagt ccccaggctc  1740
cccagcaggc agaagtatgc aaagcatgca tctcaattag tcagcaacca tagtcccgcc  1800
cctaactccg cccatcccgc ccctaactcc gcccagttcc gcccattctc cgccccatgg  1860
ctgactaatt ttttttattt atgcagaggc cgaggccgcc tcggcctctg agctattcca  1920
gaagtagtga ggaggctttt ttggaggcct aggcttttgc aaaaagctgc ggccgccacc  1980
atgggcagca agcccagcac aagaatccca gcccccctga tgctgatcac ccgcatcatg  2040
ctgatcctgg gctgcatcag acccacaagc tccctggatg gacgccccct ggccgctgcc  2100
ggcatcgtgg tgaccggcga caaggccgtg aacgtgtaca ccagcagcca gaccggcagc  2160
atcatcgtga agctgctgcc caacatgccc agagacaaag aggcctgcgc caaggccccc  2220
ctggaagcct acaacagaac cctgaccacc ctgctgaccc ccctgggcga cagcatcaga  2280
aagatccagg gctccgtgag cacaagcggc ggaggaaagc agggcagact gatcggcgcc  2340
gtgatcggca gcgtggccct gggagtggct acagctgccc agattaccgc tgcagccgcc  2400
ctgatccagg ccaaccagaa cgccgccaac atcctgagac tgaaagagag cattgccgcc  2460
accaacgagg ccgtgcacga agtgaccgac ggcctgagcc agctgtccgt ggccgtgggc  2520
aagatgcagc agttcgtgaa cgaccagttc aacaacaccg ccagagagct ggactgcatc  2580
aagatcaccc agcaggtggg cgtggagctg aacctgtacc tgaccgagct gaccacagtg  2640
ttcggccccc agatcacaag cccagccctg acacagctga ccatccaggc cctgtacaac  2700
```

```
ctggctggcg gcaacatgga ctatctgctg acaaagctgg gaatcggcaa caaccagctg  2760
tccagcctga tcggaagcgg cctgatcacc ggctacccca tcctgtacga cagccagaca  2820
cagctgctgg gcatccaggt gaacctgccc agcgtgggca acctgaacaa catgcgcgcc  2880
acctacctgg aaaccctgag cgtgtccacc accaagggct acgccagcgc cctggtgccc  2940
aaggtggtga cacaggtggg cagcgtgatc gaggaactgg acaccagcta ctgcatcgag  3000
agcgacctgg acctgtactg caccagaatc gtgaccttcc caatgagccc cggcatctac  3060
agctgcctga gcggcaacac cagcgcctgc atgtacagca agaccgaagg cgcactgaca  3120
acaccctaca tggccctgaa gggaagcgtg atcgccaact gcaagatcac cacctgcaga  3180
tgcaccgacc ccccaggcat catcagccag aactacggcg aggccgtgag cctgatcgat  3240
cgccattcct gtaacgtgct gtccctggac ggcatcacac tgagactgag cggcgagttc  3300
gatgccacct accagaagaa catcagcatc ctggacagcc aggtgatcgt gaccggcaac  3360
ctggacatca gcaccgagct gggcaacgtg aataacagca tcagcaacgc cctggacaga  3420
ctggccgaga gcaacagcaa gctggaaaaa gtgaacgtgc gcctgacatc cacttccgct  3480
ctgatcacct acatcgtgct gaccgtgatc agcctggtgt tcggcgccct gagcctggtg  3540
ctggcctgct acctgatgta caagcagaag gcccagcaga aaaccctgct gtggctgggc  3600
aacaacaccc tggaccagat gagagccacc accagagcct gatgagcggc cgcaataaaa  3660
tatctttatt ttcattacat ctgtgtgttg gtttttgtg tgaatcgata gtactaacat  3720
acgctctcca tcaaaacaaa acgaaacaaa acaaactagc aaaataggct gtccccagtg  3780
caagtgcagg tgccagaaca tttctct                                      3807
```

```
SEQ ID NO: 13           moltype = DNA  length = 3809
FEATURE                 Location/Qualifiers
source                  1..3809
                        mol_type = other DNA
                        organism = synthetic construct
                        note = pFIRESVP2 for vHVT310
misc_feature            1..1362
                        note = IBDV VP2
misc_feature            1363..1925
                        note = IRES
misc_feature            1929..3590
                        note = NDV-Fopt VIId
misc_feature            3611..3809
                        note = SV40 Poly A
SEQUENCE: 13
atgacaaacc tgcaagatca aacccaacag attgttccgt tcatacggag ccttctgatg  60
ccaacaaccg gaccggcgtc cattccggac gacaccctgg agaagcacac tctcaggtca  120
gagacctcga cctacaattt gactgtgggg gacacagggt cagggctaat tgtctttttc  180
cctggattcc ctggctcaat tgtgggtgct cactacacac tgcagagcaa tgggaactac  240
aagttcgatc agatgctcct gactgcccag aacctaccgg ccagctacaa ctactgcaga  300
ctagtgagtc ggagtctcac agtgaggtca agcacactcc ctggtggcgt ttatgcacta  360
aacggcacca taaacgccgt gaccttccaa ggaagcctga gtgaactgac agatgttagc  420
tacaatgggt tgatgtctgc aacagccaac atcaacgaca aaattgggaa tgtcctggta  480
ggggaagggg tcactgtcct cagcctaccc acatcatatg atcttgggta tgtgaggctt  540
ggtgacccca ttcccgctat agggcttgac ccaaaaatgg tagctacatg cgacagcagt  600
gacaggccca gagtctacac cataactgca gccgatgatt accaattctc atcacagtac  660
caaccaggtg ggtaacaat cacactgttc tcagccaaca ttgatgctat cacaagcctc  720
agcattgggg gagagctcgt gtttcaaaca agcgtccaag gccttgtact gggcgccacc  780
atctacctta taggctttga tgggactgcg gtaatcacca gagctgtagc cgcagataat  840
gggctgacgg ccggcaccga caatcttatg ccattcaatc ttgtcattcc aaccaatgag  900
ataacccagc caatcacatc catcaaactg gagatagtga cctccaaaag tggtggtcag  960
gcaggggatc agatgtcatg gtcggcaagt gggagcctag cagtgacgat ccatggtggc  1020
aactatccag ggccctccg tcccgtcaca ctagtagcct acgaaagagt ggcaacagga  1080
tccgtcgtta cggtcgctgg ggtgagtaac ttcgagctga ttccaaatcc tgaactagca  1140
aagaacctgg ttacagaata cggccgattt gacccaggag ccatgaacta cacaaaattg  1200
atactgagtg agagggaccg tcttggcatc aagaccgtct ggccaacaag ggagtacact  1260
gattttcgtg agtacttcat ggaggtggcc gacctcaact ctcccctgaa gattgcagga  1320
gcatttggct tcaaagacat aatccgggct ataaggaggt aacccccccc cctaacgtta  1380
ctggccgaag ccgcttggaa taaggccggt gtgcgtttgt ctatatgtta ttttccacca  1440
tattgccgtc ttttggcaat gtgagggccc ggaaacctgg ccctgtcttc ttgacgagca  1500
ttcctagggg tctttcccct ctcgccaaag gaatgcaagg tctgttgaat gtcgtgaagg  1560
aagcagttcc tctggaagct tcttgaagac aaacaacgtc tgtagcgacc ctttgcaggc  1620
agcggaaccc cccacctggc gacaggtgcc tctgcggcca aaagccacgt gtataagata  1680
cacctgcaaa ggcggcacaa ccccagtgcc acgttgtgag ttggatagtt gtggaaagag  1740
tcaaatggct ctcctcaagc gtattcaaca aggggctgaa ggatgcccag aaggtacccc  1800
attgtatggg atctgatctg gggcctcggt gcacatgctt tacatgtgtt tagtcgaggt  1860
taaaaaacgt ctaggccccc cgaaccacgg ggacgtggtt ttcctttgaa aaacacgatg  1920
ataataccat gggcagcaag cccagcacaa gaatcccagc cccctgatg ctgatcaccc  1980
gcatcatgct gatcctgggc tgcatcagac ccacaagctc cctggatgga cgcccctgg  2040
ccgctgccgg catcgtggtg accggcgaca aggccgtgaa cgtgtacacc agcagccaga  2100
ccggcagcat catcgtgaag ctgctgccca acatgcccag agacaaagag gcctgcgcca  2160
aggccccct ggaagcctac aacagaaccc tgaccaccct gctgaccccc ctgggcgaca  2220
gcatcagaaa gatccagggc tccgtgagca caagcggcgg aggaaagcag ggcagactga  2280
tcggcgccgt gatcggcagc gtggccctgg gagtggctac agctgcccag attaccgctg  2340
cagccgccct gatccaggcc aaccagaacg ccgccaacat cctgagactg aaagagagca  2400
ttgccgccac caacgaggcc gtgcacgaag tgaccgacgg cctgagccag ctgtccgtgg  2460
ccgtgggcaa gatgcagcag ttcgtgaacg accagttcaa caacaccgcc agagagctgg  2520
actgcatcaa gatcacccag caggtgggcg tggagctgaa cctgtacctg accgagctga  2580
ccacagtgtt cggcccccag atcacaagcc cagccctgac acagctgacc atccaggccc  2640
```

-continued

```
tgtacaacct ggctggcggc aacatggact atctgctgac aaagctggga atcggcaaca  2700
accagctgtc cagcctgatc ggaagcggcc tgatcaccgg ctaccccatc ctgtacgaca  2760
gccagacaca gctgctgggc atccaggtga acctgcccag cgtgggcaac ctgaacaaca  2820
tgcgcgccac ctacctggaa accctgagcg tgtccaccac caagggctac gccagcgccc  2880
tggtgcccaa ggtggtgaca caggtgggca gcgtgatcga ggaactggac accagctact  2940
gcatcgagag cgacctggac ctgtactgca ccagaatcgt gaccttccca atgagccccg  3000
gcatctacag ctgcctgagc ggcaacacca gcgcctgcat gtacagcaag accgaaggcg  3060
cactgacaac accctacatg gccctgaagg gaagcgtgat cgccaactgc aagatcacca  3120
cctgcagatg caccgacccc ccaggcatca tcagccagaa ctacggcgag gccgtgagcc  3180
tgatcgatcg ccattcctgt aacgtgctgt ccctggacgg catcacactg agactgagcg  3240
gcgagttcga tgccacctac cagaagaaca tcagcatcct ggacagccag gtgatcgtga  3300
ccggcaacct ggacatcagc accgagctgg gcaacgtgaa taacagcatc agcaacgccc  3360
tggacagact ggccgagagc aacagcaagc tggaaaaagt gaacgtgcgc ctgacatcca  3420
cttccgctct gatcacctac atcgtgctga ccgtgatcag cctggtgttc ggcgccctga  3480
gcctggtgct ggcctgctac ctgatgtaca agcagaaggc ccagcagaaa accctgctgt  3540
ggctgggcaa caacaccctg gaccagatga gagccaccac cagagcctga gcttgatcta  3600
gagcggccgc ggggatccag acatgataag atacattgat gagtttggac aaaccacaac  3660
tagaatgcag tgaaaaaaat gctttatttg tgaaatttgt gatgctattg ctttatttgt  3720
aaccattata agctgcaata aacaagttaa caacaacaat tgcattcatt ttatgtttca  3780
ggttcagggg gaggtgtggg aggtttttt                                   3809
```

```
SEQ ID NO: 14          moltype = DNA  length = 3309
FEATURE                Location/Qualifiers
source                 1..3309
                       mol_type = other DNA
                       organism = synthetic construct
                       note = pFP2AVP2 for vHVT311
misc_feature           1..1359
                       note = IBDV VP2
misc_feature           1360..1425
                       note = P2A
misc_feature           1426..3087
                       note = NDV-F wildtype VIId
misc_feature           3111..3309
                       note = SV40 Poly A
SEQUENCE: 14
atgacaaacc tgcaagatca aacccaacag attgttccgt tcatacggag ccttctgatg  60
ccaacaaccg gaccggcgtc cattccggac gacaccctgg agaagcacac tctcaggtca  120
gagacctcga cctacaattt gactgtgggg gacacagggt cagggctaat tgtctttttc  180
cctggattcc ctggctcaat tgtgggtgct cactacacac tgcagagcaa tgggaactac  240
aagttcgatc agatgctcct gactgcccag aacctaccgg ccagctacaa ctactgcaga  300
ctagtgagtc ggagtctcac agtgaggtca agcacactcc ctggtggcgt ttatgcacta  360
aacggcacca taaacgccgt gaccttccaa ggaagcctga gtgaactgac agatgttagc  420
tacaatgggt tgatgtctgc aacagccaac atcaacgaca aaattgggaa tgtcctggta  480
ggggaagggg tcactgtcct cagcctaccc acatcatatg atcttgggta tgtgaggctt  540
ggtgacccca ttcccgctat agggcttgac ccaaaaatgg tagctacatg cgacagcagt  600
gacaggccca gagtctacac cataactgca gccgatgatt accaattctc atcacagtac  660
caaccaggtg gggtaacaat cacactgttc tcagccaaca ttgatgctat cacaagcctc  720
agcattgggg gagagctcgt gtttcaaaca agcgtccaag gccttgtact gggcgccacc  780
atctacctta taggctttga tgggactgcg gtaatcacca gagctgtagc cgcagataat  840
gggctgacgg ccggcaccga caatcttatg ccattcaatc ttgtcattcc aaccaatgag  900
ataacccagc caatcacatc catcaaactg gagatagtga cctccaaaag tggtggtcag  960
gcaggggatc agatgtcatg gtcggcaagt gggagcctag cagtgacgat ccatggtggc  1020
aactatccag gggccctccg tcccgtcaca ctagtagcct acgaaagagt ggcaacagga  1080
tccgtcgtta cggtcgctgg ggtgagtaac ttcgagctga ttccaaatcc tgaactagca  1140
aagaacctgg ttacagaata cggccgattt gacccaggag ccatgaacta cacaaaattg  1200
atactgagtg agagggaccg tcttggcatc aagaccgtct ggccaacaag ggagtacact  1260
gattttcgtg agtacttcat ggaggtggcc gacctcaact ctcccctgaa gattgcagga  1320
gcatttggct tcaaagacat aatccgggct ataaggaggg gctccggcgc caccaacttc  1380
tccctgctca agcaggccgg cgacgtggag gagaaccctg gacctatggg ctccaaacct  1440
tctaccagga tcccagcacc tctgatgctg atcacccgga ttatgctgat attgggctgt  1500
atccgtccga caagctctct tgacggcagg cctcttgcag ctgcaggaat tgtagtaaca  1560
ggagataagg cagtcaatgt atacacttcg tctcagacag ggtcaatcat agtcaagttg  1620
ctcccgaata tgcccaggga taaggaggcg tgtgcaaaag ccccattaga ggcatataac  1680
agaacactga ctactttgct cactcctctt ggcgactcca tccgcaagat ccaagggtct  1740
gtgtccacat ctggaggagg caagcaaggc cgcctgatag gtgctgttat tggcagtgta  1800
gctcttgggg ttgcaacagc ggcacagata acagcagctg cggccctaat acaagccaac  1860
cagaatgccg ccaacatcct ccggcttaag gagagcattg ctgcaaccaa tgaagctgtg  1920
catgaagtca ccgacggatt atcacaacta tcagtggcag ttgggaagat gcagcagttt  1980
gtcaatgacc agtttaataa tacggcgcga gaattggact gtataaaaat cacacaacag  2040
gttggtgtag aactcaacct atacctaact gaattgacta cagtattcgg gccacagatc  2100
acctcccctg cattaactca gctgaccatc caggcacttt ataatttagc tggtggcaat  2160
atggattact tattaactaa gttaggtata gggaacaatc aactcagctc gttaattggt  2220
agcggcctga tcactggtta ccctatactg tatgactcac agactcaact cttgggcata  2280
caagtgaatt taccctcagt cgggaactta aataatatgc gtgccaccta tttggagacc  2340
ttatctgtaa gtacaaccaa aggatatgcc tcagcacttg tcccgaaagt agtgacacaa  2400
gtcggttccg tgatagaaga gcttgacacc tcatactgta tagagtccga tctggattta  2460
tattgtacta gaatagtgac attccccatg tccccaggta tttattcctg tttgagcggc  2520
aacacatcag cttgcatgta ttcaaagact gaaggcgcac tcactacgcc gtatatggcc  2580
```

```
cttaaaggct cagttattgc caattgtaaa ataacaacat gtagatgtac agaccctcct  2640
ggtatcatat cgcaaaatta tggagaagct gtatccctga tagatagaca ttcgtgcaat  2700
gtcttatcat tagacgggat aactctaagg ctcagtgggg aatttgatgc aacttatcaa  2760
aagaacatct caatactaga ttctcaagtc atcgtgacag gcaatcttga tatatcaact  2820
gaacttggaa acgtcaacaa ttcaatcagc aatgccttgg ataggttggc agaaagcaac  2880
agcaagctag aaaaagtcaa tgtcagacta accagcacat ctgctctcat tacctatatt  2940
gttctaactg tcatttctct agttttcggt gcacttagtc tggtgttagc gtgttacctg  3000
atgtacaaac agaaggcaca acaaaagacc ttgctatggc ttgggaataa taccctcgat  3060
cagatgagag ccactacaag agcatgataa gcttgatcta gagcggccgc ggggatccag  3120
acatgataag atacattgat gagtttggac aaaccacaac tagaatgcag tgaaaaaaat  3180
gctttatttg tgaaatttgt gatgctattg ctttatttgt aaccattata agctgcaata  3240
aacaagttaa caacaacaat tgcattcatt ttatgtttca ggttcagggg gaggtgtggg  3300
aggtttttt                                                          3309

SEQ ID NO: 15           moltype = DNA  length = 3440
FEATURE                 Location/Qualifiers
source                  1..3440
                        mol_type = other DNA
                        organism = synthetic construct
                        note = pVP2IRESgD for vHVT317
misc_feature            1..1362
                        note = IBDV VP2
misc_feature            1363..1925
                        note = IRES
misc_feature            1929..3233
                        note = ILTV-gD
misc_feature            3242..3440
                        note = SV40 Poly A
SEQUENCE: 15
atgacaaacc tgcaagatca aacccaacag attgttccgt tcatacggag ccttctgatg  60
ccaacaaccg gaccggcgtc cattccggac gacaccctgg agaagcacac tctcaggtca  120
gagacctcga cctacaattt gactgtgggg gacacagggt cagggctaat tgtctttttc  180
cctggattcc ctggctcaat tgtgggtgct cactacacac tgcagagcaa tgggaactac  240
aagttcgatc agatgctcct gactgcccag aacctaccgg ccagctacaa ctactgcaga  300
ctagtgagtc ggagtctcac agtgaggtca agcacactcc ctggtggcgt ttatgcacta  360
aacggcacca taaacgccgt gaccttccaa ggaagcctga gtgaactgac agatgttagc  420
tacaatgggt tgatgtctgc aacagccaac atcaacgaca aaattgggaa tgtcctggta  480
ggggaagggg tcactgtcct cagcctaccc acatcatatg atcttgggta tgtgaggctt  540
ggtgacccca ttcccgctat agggcttgac ccaaaaatgg tagctacatg cgacagcagt  600
gacaggccca gagtctacac cataactgca gccgatgatt accaattctc atcacagtac  660
caaccaggtg gggtaacaat cacactgttc tcagccaaca ttgatgctat cacaagcctc  720
agcattgggg gagagctcgt gtttcaaaca agcgtccaag gccttgtact gggcgccacc  780
atctacctta taggctttga tgggactgcg gtaatcacca gagctgtagc cgcagataat  840
gggctgacgg ccggcaccga caatcttatg ccattcaatc ttgtcattcc aaccaatgag  900
ataacccagc caatcacatc catcaaactg gagatagtga cctccaaaag tggtggtcag  960
gcaggggatc agatgtcatg gtcggcaagt gggagcctag cagtgacgat ccatggtggc  1020
aactatccag ggccctccg tcccgtcaca ctagtagcct acgaaagagt ggcaacagga  1080
tccgtcgtta cggtcgctgg ggtgagtaac ttcgagctga ttccaaatcc tgaactagca  1140
aagaacctgg ttacagaata cggccgattt gacccaggag ccatgaacta cacaaaattg  1200
atactgagtg agagggaccg tcttggcatc aagaccgtct ggccaacaag ggagtacact  1260
gattttcgtg agtacttcat ggaggtggcc gacctcaact ctcccctgaa gattgcagga  1320
gcatttggct tcaaagacat aatccgggct ataaggaggt aacccccccc cctaacgtta  1380
ctggccgaag ccgcttggaa taaggccggt gtgcgtttgt ctatatgtta ttttccacca  1440
tattgccgtc ttttggcaat gtgagggccc ggaaacctgg ccctgtcttc ttgacgagca  1500
ttcctagggg tctttcccct ctcgccaaag gaatgcaagg tctgttgaat gtcgtgaagg  1560
aagcagttcc tctggaagct tcttgaagac aaacaacgtc tgtagcgacc ctttgcaggc  1620
agcggaaccc cccacctggc gacaggtgcc tctgcggcca aaagccacgt gtataagata  1680
cacctgcaaa ggcggcacaa ccccagtgcc acgttgtgag ttggatagtt gtggaaagag  1740
tcaaatggct ctcctcaagc gtattcaaca aggggctgaa ggatgcccag aaggtacccc  1800
attgtatggg atctgatctg gggcctcggt gcacatgctt tacatgtgtt tagtcgaggt  1860
taaaaaacgt ctaggccccc cgaaccacgg ggacgtggtt ttcctttgaa aaacacgatg  1920
ataataccat gcaccgtcct catctcagac ggcactcgcg ttactacgcg aaaggagagg  1980
tgcttaacaa acacatggat tgcggtggaa aacggtgctg ctcaggcgca gctgtattca  2040
ctcttttctg gacttgtgtc aggattatgc gggagcatat ctgctttgta cgcaacgcta  2100
tggaccgcca tttatttttg aggaatgctt tttggactat cgtactgctt tcttccttcg  2160
ctagccagag caccgccgcc gtcacgtacg actacatttt aggccgtcgc gcgctcgacg  2220
cgctaaccat accggcggtt ggcccgtata acagatacct cactagggta tcaagaggct  2280
gcgacgttgt cgagctcaac ccgatttcta acgtggacga catgatatcg gcggccaaag  2340
aaaaagagaa ggggggccct ttcgaggcct ccgtcgtctg gttctacgtg attaagggcg  2400
acgacggcga ggacaagtac tgtccaatct atagaaaaga gtacagggaa tgtggcgacg  2460
tacaactgct atctgaatgc gccgttcaat ctgcacagat gtgggcagtg gactatgttc  2520
ctagcaccct tgtatcgcga aatggcgcgg gactgactat attctccccc actgctgcgc  2580
tctctggcca atacttgctg accctgaaaa tcgggagatt tgcgcaaaca gctctcgtaa  2640
ctctagaagt taacgatcgc tgtttaaaga tcgggtcgca gcttaacttt ttaccgtcga  2700
aatgctggac aacagaacag tatcagactg gatttcaagg cgaacacctt tatccgatcg  2760
cagacaccaa tacacgacac gcggacgacg tatatcgggg atacgaagat attctgcagc  2820
gctggaataa tttgctgagg aaaaagaatc ctagcgcgcc agaccctcgt ccagatagcg  2880
tcccgcaaga aattcccgct gtaaccaaga aagcggaagg gcgcaccccg gacgcagaaa  2940
gcagcgaaaa gaaggcccct ccagaagact cggaggacga catgcaggca gaggcttctg  3000
```

-continued

```
gagaaaatcc tgccgccctc cccgaagacg acgaagtccc cgaggacacc gagcacgatg  3060
atccaaactc ggatcctgac tattacaatg acatgcccgc cgtgatcccg gtggaggaga  3120
ctactaaaag ttctaatgcc gtctccatgc ccatattcgc ggcgttcgta gcctgcgcgg  3180
tcgcgctcgt ggggctactg gtttggagca tcgtaaaatg cgcgcgtagc taagcggccg  3240
cggggatcca gacatgataa gatacattga tgagtttgga caaaccacaa ctagaatgca  3300
gtgaaaaaaa tgctttattt gtgaaatttg tgatgctatt gctttatttg taaccattat  3360
aagctgcaat aaacaagtta acaacaacaa ttgcattcat tttatgtttc aggttcaggg  3420
ggaggtgtgg gaggtttttt                                              3440

SEQ ID NO: 16          moltype = DNA  length = 1302
FEATURE                Location/Qualifiers
source                 1..1302
                       mol_type = other DNA
                       organism = synthetic construct
                       note = Polynucleotide encoding ILTV gD
SEQUENCE: 16
atgcaccgtc ctcatctcag acggcactcg cgttactacg cgaaaggaga ggtgcttaac  60
aaacacatgg attgcggtgg aaaacggtgc tgctcaggcg cagctgtatt cactcttttc  120
tggacttgtg tcaggattat gcgggagcat atctgctttg tacgcaacgc tatggaccgc  180
catttatttt tgaggaatgc tttttggact atcgtactgc tttcttcctt cgctagccag  240
agcaccgccg ccgtcacgta cgactacatt ttaggccgtc gcgcgctcga cgcgctaacc  300
ataccggcgg ttggcccgta taacagatac ctcactaggg tatcaagagg ctgcgacgtt  360
gtcgagctca acccgatttc taacgtggac gacatgatat cggcggccaa agaaaaagag  420
aaggggggcc ctttcgaggc ctccgtcgtc tggttctacg tgattaaggg cgacgacggc  480
gaggacaagt actgtccaat ctatagaaaa gagtacaggg aatgtggcga cgtacaactg  540
ctatctgaat gcgccgttca atctgcacag atgtgggcag tggactatgt tcctagcacc  600
cttgtatcgc gaaatggcgc gggactgact atattctccc ccactgctgc gctctctggc  660
caatacttgc tgaccctgaa aatcgggaga tttgcgcaaa cagctctcgt aactctagaa  720
gttaacgatc gctgtttaaa gatcgggtcg cagcttaact ttttaccgtc gaaatgctgg  780
acaacagaac agtatcagac tggatttcaa ggcgaacacc tttatccgat cgcagacacc  840
aatacacgac acgcggacga cgtatatcgg ggatacgaag atattctgca gcgctggaat  900
aatttgctga ggaaaaagaa tcctagcgcg ccagaccctc gtccagatag cgtcccgcaa  960
gaaattcccg ctgtaaccaa gaaagcggaa gggcgcaccc cggacgcaga aagcagcgaa  1020
aagaaggccc ctccagaaga ctcggaggac gacatgcagg cagaggcttc tggagaaaat  1080
cctgccgccc tccccgaaga cgacgaagtc cccgaggaca ccgagcacga tgatccaaac  1140
tcggatcctg actattacaa tgacatgccc gccgtgatcc cggtggagga gactactaaa  1200
agttctaatg ccgtctccat gcccatattc gcggcgttcg tagcctgcgc ggtcgcgctc  1260
gtggggctac tggtttggag catcgtaaaa tgcgcgcgta gc                     1302

SEQ ID NO: 17          moltype = AA  length = 434
FEATURE                Location/Qualifiers
source                 1..434
                       mol_type = protein
                       organism = synthetic construct
                       note = ILTV gD protein
SEQUENCE: 17
MHRPHLRRHS RYYAKGEVLN KHMDCGGKRC CSGAAVFTLF WTCVRIMREH ICFVRNAMDR  60
HLFLRNAFWT IVLLSSFASQ STAAVTYDYI LGRRALDALT IPAVGPYNRY LTRVSRGCDV  120
VELNPISNVD DMISAAKEKE KGGPFEASVV WFYVIKGDDG EDKYCPIYRK EYRECGDVQL  180
LSECAVQSAQ MWAVDYVPST LVSRNGAGLT IFSPTAALSG QYLLTLKIGR FAQTALVTLE  240
VNDRCLKIGS QLNFLPSKCW TTEQYQTGFQ GEHLYPIADT NTRHADDVYR GYEDILQRWN  300
NLLRKKNPSA PDPRPDSVPQ EIPAVTKKAE GRTPDAESSE KKAPPEDSED DMQAEASGEN  360
PAALPEDDEV PEDTEHDDPN SDPDYYNDMP AVIPVEETTK SSNAVSMPIF AAFVACAVAL  420
VGLLVWSIVK CARS                                                    434

SEQ ID NO: 18          moltype = DNA  length = 3804
FEATURE                Location/Qualifiers
source                 1..3804
                       mol_type = other DNA
                       organism = synthetic construct
                       note = pFwtSV40VP2 for vHFT313
misc_feature           1..1362
                       note = VP2
misc_feature           1383..1594
                       note = SV40 Poly A
misc_feature           1624..1968
                       note = SV40 Promoter
misc_feature           1981..3642
                       note = NDV-Fwt VIId
misc_feature           3651..3804
                       note = Synthetic Poly A
SEQUENCE: 18
atgacaaacc tgcaagatca aacccaacag attgttccgt tcatacggag ccttctgatg  60
ccaacaaccg gaccggcgtc cattccggac gacaccctgg agaagcacac tctcaggtca  120
gagacctcga cctacaattt gactgtgggg gacacagggt cagggctaat tgtctttttc  180
cctggattcc ctggctcaat tgtgggtgct cactacacac tgcagagcaa tgggaactac  240
aagttcgatc agatgctcct gactgcccag aacctaccgg ccagctacaa ctactgcaga  300
ctagtgagtc ggagtctcac agtgaggtca agcacactcc ctggtggcgt ttatgcacta  360
aacggcacca taaacgccgt gaccttccaa ggaagcctga gtgaactgac agatgttagc  420
```

-continued

```
tacaatgggt tgatgtctgc aacagccaac atcaacgaca aaattgggaa tgtcctggta  480
ggggaagggg tcactgtcct cagcctaccc acatcatatg atcttgggta tgtgaggctt  540
ggtgacccca ttcccgctat agggcttgac ccaaaaatgg tagctacatg cgacagcagt  600
gacaggccca gagtctacac cataactgca gccgatgatt accaattctc atcacagtac  660
caaccaggtg gggtaacaat cacactgttc tcagccaaca ttgatgctat cacaagcctc  720
agcattgggg gagagctcgt gtttcaaaca agcgtccaag gccttgtact gggcgccacc  780
atctacctta taggctttga tgggactgcg gtaatcacca gagctgtagc cgcagataat  840
gggctgacgg ccggcaccga caatcttatg ccattcaatc ttgtcattcc aaccaatgag  900
ataacccagc caatcacatc catcaaactg gagatagtga cctccaaaag tggtggtcag  960
gcaggggatc agatgtcatg gtcggcaagt gggagcctag cagtgacgat ccatggtggc  1020
aactatccag ggccctccg tcccgtcaca ctagtagcct acgaaagagt ggcaacagga  1080
tccgtcgtta cggtcgctgg ggtgagtaac ttcgagctga ttccaaatcc tgaactagca  1140
aagaacctgg ttacagaata cggccgattt gacccaggag ccatgaacta cacaaaattg  1200
atactgagtg agagggaccg tcttggcatc aagaccgtct ggccaacaag ggagtacact  1260
gattttcgtg agtacttcat ggaggtggcc gacctcaact ctcccctgaa gattgcagga  1320
gcatttggct tcaaagacat aatccgggct ataaggaggt aagcttgatc tagagcggcc  1380
gcggggatcc agacatgata agatacattg atgagtttgg acaaaccaca actagaatgc  1440
agtgaaaaaa atgctttatt tgtgaaattt gtgatgctat tgctttattt gtaaccatta  1500
taagctgcaa taaacaagtt aacaacaaca attgcattca ttttatgttt caggttcagg  1560
gggaggtgtg ggaggttttt tcggatcctc tagagtcgac gaattcgagc tcggtacagc  1620
ttggctgtgg aatgtgtgtc agttagggtg tggaaagtcc ccaggctccc cagcaggcag  1680
aagtatgcaa agcatgcatc tcaattagtc agcaaccagg tgtggaaagt ccccaggctc  1740
cccagcaggc agaagtatgc aaagcatgca tctcaattag tcagcaacca tagtcccgcc  1800
cctaactccg cccatcccgc ccctaactcc gcccagttcc gcccattctc cgccccatgg  1860
ctgactaatt ttttttattt atgcagaggc cgaggccgcc tcggcctctg agctattcca  1920
gaagtagtga ggaggctttt ttggaggcct aggcttttgc aaaaagctgc ggccgccacc  1980
atgggctcca aaccttctac caggatccca gcacctctga tgctgatcac ccggattatg  2040
ctgatattgg gctgtatccg tccgacaagc tctcttgacg gcaggcctct tgcagctgca  2100
ggaattgtag taacaggaga taaggcagtc aatgtataca cttcgtctca gacagggtca  2160
atcatagtca agttgctccc gaatatgccc agggataagg aggcgtgtgc aaaagcccca  2220
ttagaggcat ataacagaac actgactact ttgctcactc ctcttggcga ctccatccgc  2280
aagatccaag ggtctgtgtc cacatctgga ggaggcaagc aaggccgcct gataggtgct  2340
gttattggca gtgtagctct tggggttgca acagcggcac agataacagc agctgcggcc  2400
ctaatacaag ccaaccagaa tgccgccaac atcctccggc ttaaggagag cattgctgca  2460
accaatgaag ctgtgcatga agtcaccgac ggattatcac aactatcagt ggcagttggg  2520
aagatgcagc agtttgtcaa tgaccagttt aataatacgg cgcgagaatt ggactgtata  2580
aaaatcacac aacaggttgg tgtagaactc aacctatacc taactgaatt gactacagta  2640
ttcgggccac agatcacctc ccctgcatta actcagctga ccatccaggc actttataat  2700
ttagctggtg gcaatatgga ttacttatta actaagttag gtatagggaa caatcaactc  2760
agctcgttaa ttggtagcgg cctgatcact ggttacccta tactgtatga ctcacagact  2820
caactcttgg gcatacaagt gaatttaccc tcagtcggga acttaaataa tatgcgtgcc  2880
acctatttgg agaccttatc tgtaagtaca accaaaggat atgcctcagc acttgtcccg  2940
aaagtagtga cacaagtcgg ttccgtgata gaagagcttg acacctcata ctgtatagag  3000
tccgatctgg atttatattg tactagaata gtgacattcc ccatgtcccc aggtatttat  3060
tcctgtttga gcggcaacac atcagcttgc atgtattcaa agactgaagg cgcactcact  3120
acgccgtata tggcccttaa aggctcagtt attgccaatt gtaaaataac aacatgtaga  3180
tgtacagacc ctcctggtat catatcgcaa aattatggag aagctgtatc cctgatagat  3240
agacattcgt gcaatgtctt atcattagac gggataactc taaggctcag tggggaattt  3300
gatgcaactt atcaaaagaa catctcaata ctagattctc aagtcatcgt gacaggcaat  3360
cttgatatat caactgaact tggaaacgtc aacaattcaa tcagcaatgc cttggatagg  3420
ttggcagaaa gcaacagcaa gctagaaaaa gtcaatgtca gactaaccag cacatctgct  3480
ctcattacct atattgttct aactgtcatt tctctagttt tcggtgcact tagtctggtg  3540
ttagcgtgtt acctgatgta caaacagaag gcacaacaaa agaccttgct atggcttggg  3600
aataataccc tcgatcagat gagagccact acaagagcat gagcggccgc aataaaatat  3660
ctttattttc attacatctg tgtgttggtt ttttgtgtga atcgatagta ctaacatacg  3720
ctctccatca aaacaaaacg aaacaaaaca aactagcaaa ataggctgtc cccagtgcaa  3780
gtgcaggtgc cagaacattt ctct                                         3804
```

```
SEQ ID NO: 19          moltype = DNA  length = 3797
FEATURE                Location/Qualifiers
source                 1..3797
                       mol_type = other DNA
                       organism = synthetic construct
                       note = pVP2IRESFwt for vHVT316
misc_feature           1..1362
                       note = VP2
misc_feature           1363..1925
                       note = IRES
misc_feature           1929..3590
                       note = NDV-Fwt VIId
misc_feature           3599..3797
                       note = SV40 Poly A
SEQUENCE: 19
atgacaaacc tgcaagatca aacccaacag attgttccgt tcatacggag ccttctgatg  60
ccaacaaccg gaccggcgtc cattccggac gacaccctgg agaagcacac tctcaggtca  120
gagacctcga cctacaattt gactgtgggg gacacagggt cagggctaat tgtctttttc  180
cctggattcc ctggctcaat tgtgggtgct cactacacac tgcagagcaa tgggaactac  240
aagttcgatc agatgctcct gactgcccag aacctaccgg ccagctacaa ctactgcaga  300
ctagtgagtc ggagtctcac agtgaggtca agcacactcc ctggtggcgt ttatgcacta  360
```

-continued

```
aacggcacca taaacgccgt gaccttccaa ggaagcctga gtgaactgac agatgttagc  420
tacaatgggt tgatgtctgc aacagccaac atcaacgaca aaattgggaa tgtcctggta  480
ggggaagggg tcactgtcct cagcctaccc acatcatatg atcttgggta tgtgaggctt  540
ggtgacccca ttcccgctat agggcttgac ccaaaaatgg tagctacatg cgacagcagt  600
gacaggccca gagtctacac cataactgca gccgatgatt accaattctc atcacagtac  660
caaccaggtg gggtaacaat cacactgttc tcagccaaca ttgatgctat cacaagcctc  720
agcattgggg gagagctcgt gtttcaaaca agcgtccaag gccttgtact gggcgccacc  780
atctacctta taggctttga tgggactgcg gtaatcacca gagctgtagc cgcagataat  840
gggctgacgg ccggcaccga caatcttatg ccattcaatc ttgtcattcc aaccaatgag  900
ataacccagc caatcacatc catcaaactg gagatagtga cctccaaaag tggtggtcag  960
gcaggggatc agatgtcatg gtcggcaagt gggagcctag cagtgacgat ccatggtggc  1020
aactatccag gggccctccg tcccgtcaca ctagtagcct acgaaagagt ggcaacagga  1080
tccgtcgtta cggtcgctgg ggtgagtaac ttcgagctga ttccaaatcc tgaactagca  1140
aagaacctgg ttacagaata cggccgattt gacccaggag ccatgaacta cacaaaattg  1200
atactgagtg agagggaccg tcttggcatc aagaccgtct ggccaacaag ggagtacact  1260
gattttcgtg agtacttcat ggaggtggcc gacctcaact ctcccctgaa gattgcagga  1320
gcatttggct tcaaagacat aatccgggct ataaggaggt aacccccccc cctaacgtta  1380
ctggccgaag ccgcttggaa taaggccggt gtgcgtttgt ctatatgtta ttttccacca  1440
tattgccgtc ttttggcaat gtgagggccc ggaaacctgg ccctgtcttc ttgacgagca  1500
ttcctagggg tctttcccct ctcgccaaag gaatgcaagg tctgttgaat gtcgtgaagg  1560
aagcagttcc tctggaagct tcttgaagac aaacaacgtc tgtagcgacc ctttgcaggc  1620
agcggaaccc cccacctggc gacaggtgcc tctgcggcca aaagccacgt gtataagata  1680
cacctgcaaa ggcggcacaa ccccagtgcc acgttgtgag ttggatagtt gtggaaagag  1740
tcaaatggct ctcctcaagc gtattcaaca aggggctgaa ggatgcccag aaggtacccc  1800
attgtatggg atctgatctg gggcctcggt gcacatgctt tacatgtgtt tagtcgaggt  1860
taaaaaacgt ctaggccccc cgaaccacgg ggacgtggtt ttcctttgaa aaacacgatg  1920
ataataccat gggctccaaa ccttctacca ggatcccagc acctctgatg ctgatcaccc  1980
ggattatgct gatattgggc tgtatccgtc cgacaagctc tcttgacggc aggcctcttg  2040
cagctgcagg aattgtagta acaggagata aggcagtcaa tgtatacact tcgtctcaga  2100
cagggtcaat catagtcaag ttgctcccga atatgcccag ggataaggag gcgtgtgcaa  2160
aagccccatt agaggcatat aacagaacac tgactacttt gctcactcct cttggcgact  2220
ccatccgcaa gatccaaggg tctgtgtcca catctggagg aggcaagcaa ggccgcctga  2280
taggtgctgt tattggcagt gtagctcttg ggggttgcaac agcggcacag ataacagcag  2340
ctgcggccct aatacaagcc aaccagaatg ccgccaacat cctccggctt aaggagagca  2400
ttgctgcaac caatgaagct gtgcatgaag tcaccgacgg attatcacaa ctatcagtgg  2460
cagttgggaa gatgcagcag tttgtcaatg accagtttaa taatacggcg cgagaattgg  2520
actgtataaa aatcacacaa caggttggtg tagaactcaa cctataccta actgaattga  2580
ctacagtatt cgggccacag atcacctccc ctgcattaac tcagctgacc atccaggcac  2640
tttataattt agctggtggc aatatggatt acttattaac taagttaggt atagggaaca  2700
atcaactcag ctcgttaatt ggtagcggcc tgatcactgg ttaccctata ctgtatgact  2760
cacagactca actcttgggc atacaagtga atttaccctc agtcgggaac ttaaataata  2820
tgcgtgccac ctatttggag accttatctg taagtacaac caaaggatat gcctcagcac  2880
ttgtcccgaa agtagtgaca caagtcggtt ccgtgataga agagcttgac acctcatact  2940
gtatagagtc cgatctggat ttatattgta ctagaatagt gacattcccc atgtccccag  3000
gtatttattc ctgtttgagc ggcaacacat cagcttgcat gtattcaaag actgaaggcg  3060
cactcactac gccgtatatg gcccttaaag gctcagttat tgccaattgt aaaataacaa  3120
catgtagatg tacagaccct cctggtatca tatcgcaaaa ttatggagaa gctgtatccc  3180
tgatagatag acattcgtgc aatgtcttat cattagacgg gataactcta aggctcagtg  3240
gggaatttga tgcaacttat caaaagaaca tctcaatact agattctcaa gtcatcgtga  3300
caggcaatct tgatatatca actgaacttg gaaacgtcaa caattcaatc agcaatgcct  3360
tggataggtt ggcagaaagc aacagcaagc tagaaaaagt caatgtcaga ctaaccagca  3420
catctgctct cattacctat attgttctaa ctgtcatttc tctagttttc ggtgcactta  3480
gtctggtgtt agcgtgttac ctgatgtaca aacagaaggc acaacaaaag accttgctat  3540
ggcttgggaa taataccctc gatcagatga gagccactac aagagcatga ggcgcgccgg  3600
ggatccagac atgataagat acattgatga gtttggacaa accacaacta gaatgcagtg  3660
aaaaaaatgc tttatttgtg aaatttgtga tgctattgct ttatttgtaa ccattataag  3720
ctgcaataaa caagttaaca acaacaattg cattcatttt atgtttcagg ttcaggggga  3780
ggtgtgggag gtttttt                                                  3797

SEQ ID NO: 20          moltype = DNA  length = 1834
FEATURE                Location/Qualifiers
source                 1..1834
                       mol_type = other DNA
                       organism = synthetic construct
                       note = HVT US2SVgDwtsyn for vHVT407
misc_feature           1..345
                       note = SV40 Promoter
misc_feature           362..1666
                       note = ILTV gDwt
misc_feature           1681..1834
                       note = synthetic poly A
SEQUENCE: 20
gctgtggaat gtgtgtcagt tagggtgtgg aaagtcccca ggctccccag caggcagaag  60
tatgcaaagc atgcatctca attagtcagc aaccaggtgt ggaaagtccc caggctcccc  120
agcaggcaga agtatgcaaa gcatgcatct caattagtca gcaaccatag tcccgcccct  180
aactccgccc atcccgcccc taactccgcc cagttccgcc cattctccgc cccatggctg  240
actaattttt tttatttatg cagaggccga ggccgcctcg gcctctgagc tattccagaa  300
gtagtgagga ggcttttttg gaggcctagg cttttgcaaa aagctgcggc cggccgccac  360
catgcaccgt cctcatctca gacggcactc gcgttactac gcgaaaggag aggtgcttaa  420
```

-continued

```
caaacacatg gattgcggtg gaaaacggtg ctgctcaggc gcagctgtat tcactctttt  480
ctggacttgt gtcaggatta tgcgggagca tatctgcttt gtacgcaacg ctatggaccg  540
ccatttattt ttgaggaatg ctttttggac tatcgtactg ctttcttcct tcgctagcca  600
gagcaccgcc gccgtcacgt acgactacat tttaggccgt cgcgcgctcg acgcgctaac  660
cataccggcg gttggcccgt ataacagata cctcactagg gtatcaagag gctgcgacgt  720
tgtcgagctc aacccgattt ctaacgtgga cgacatgata tcggcggcca aagaaaaaga  780
gaaggggggc cctttcgagg cctccgtcgt ctggttctac gtgattaagg gcgacgacgg  840
cgaggacaag tactgtccaa tctatagaaa agagtacagg gaatgtggcg acgtacaact  900
gctatctgaa tgcgccgttc aatctgcaca gatgtgggca gtggactatg ttcctagcac  960
ccttgtatcg cgaaatggcg cgggactgac tatattctcc cccactgctg cgctctctgg  1020
ccaatacttg ctgaccctga aaatcgggag atttgcgcaa acagctctcg taactctaga  1080
agttaacgat cgctgtttaa agatcgggtc gcagcttaac tttttaccgt cgaaatgctg  1140
gacaacagaa cagtatcaga ctggatttca aggcgaacac ctttatccga tcgcagacac  1200
caatacacga cacgcggacg acgtatatcg gggatacgaa gatattctgc agcgctggaa  1260
taatttgctg aggaaaaaga atcctagcgc gccagaccct cgtccagata gcgtcccgca  1320
agaaattccc gctgtaacca agaaagcgga agggcgcacc ccggacgcag aaagcagcga  1380
aaagaaggcc cctccagaag actcggagga cgacatgcag gcagaggctt ctggagaaaa  1440
tcctgccgcc ctccccgaag acgacgaagt ccccgaggac accgagcacg atgatccaaa  1500
ctcggatcct gactattaca atgacatgcc cgccgtgatc ccggtggagg agactactaa  1560
aagttctaat gccgtctcca tgcccatatt cgcggcgttc gtagcctgcg cggtcgcgct  1620
cgtggggcta ctggtttgga gcatcgtaaa atgcgcgcgt agctaatcga gcctagaggc  1680
aataaaatat ctttattttc attacatctg tgtgttggtt ttttgtgtga atcgatagta  1740
ctaacatacg ctctccatca aaacaaaacg aaacaaaaca aactagcaaa ataggctgtc  1800
cccagtgcaa gtgcaggtgc cagaacattt ctct                              1834
```

```
SEQ ID NO: 21          moltype = DNA  length = 1659
FEATURE                Location/Qualifiers
source                 1..1659
                       mol_type = other DNA
                       organism = synthetic construct
                       note = Polynucleotide encoding NDV-F of genotype V,
                        codon-optimized in pHVTIG1gDCaFopt (vHVT308)
SEQUENCE: 21
atgggcagca agcccagcac ctggatcagc gtgaccctga tgctgatcac cagaaccatg  60
ctgatcctga gctgcatctg ccccacaagc agcctggacg gcagacccct ggccgctgcc  120
ggcatcgtgg tgaccggcga caaggccgtg aacatctaca ccagcagcca gaccggcagc  180
atcatcatca agctgctgcc caacatgccc aaggacaaag aggcctgcgc caaggccccc  240
ctggaagcct acaacagaac cctgaccacc ctgctgaccc ccctgggcga cagcatcaga  300
agaatccagg gcagcgccac cacaagcggc ggaggaaagc agggcagact ggtgggcgct  360
atcatcggga gcgtggccct gggcgtggcc acagctgccc agattaccgc tgcagccgcc  420
ctgattcagg ccaatcagaa cgccgccaac atcctgagac tgaaagagag cattgccgcc  480
accaacgacg ccgtgcacga agtgacaaac ggactgtccc agctggctgt cgctgtcggc  540
aagatgcagc agttcgtgaa caaccagttc aacaacaccg ccagagagct ggactgcatc  600
aagatcgccc agcaggtggg cgtggagctg aacctgtacc tgaccgagct gaccacagtg  660
ttcggccccc agatcacaag ccccgctctg acccagctga caatccaggc cctgtacaac  720
ctggctggcg gcaacatgga ctatctgctg actaagctgg gagtgggcaa caaccagctg  780
tccagcctga tcgggtccgg gctgatcaca ggcaacccca tcctgtacga cagccagaca  840
cagctgctgg gcatccagat caacctgcca tccgtgggaa gcctgaacaa catgagagcc  900
acctacctgg aaaccctgag cgtgtccacc accaagggct tcgccagcgc cctggtgccc  960
aaggtggtga cacaggtggg cagcgtgatc gaggaactgg acaccagcta ctgcatcgag  1020
agcgacatcg acctgtactg caccagagtg gtgaccttcc caatgagccc cggcatctac  1080
agctgcctga gcggcaacac cagcgcctgc atgtacagca agaccgaagg agcactgaca  1140
acaccctaca tggccctgaa gggaagcgtg atcgccaact gcaagatgac cacctgcaga  1200
tgcgccgacc ccccaggcat catcagccag aactacggcg aggccgtgag cctgatcgac  1260
aaacattcct gtagcgtgct gtccctggat ggcatcacac tgagactgag cggcgagttc  1320
gacgccacct accagaagaa catcagcatc ctggacagcc aggtgatcgt gaccggcaac  1380
ctggacatca gcaccgagct gggcaacgtg aacaacagca tcagcagcac cctggacaag  1440
ctggccgagt ccaacaacaa gctgaacaaa gtgaacgtga acctgaccag cacaagcgcc  1500
ctgatcacct acatcgtgct ggccatcgtg tccctggcct tcggcgtgat cagcctggtg  1560
ctggcctgct acctgatgta caagcagaga gcccagcaga aaccctgct gtggctgggc  1620
aataacaccc tggaccagat gagggccacc accagaacc                          1659
```

```
SEQ ID NO: 22          moltype = AA  length = 553
FEATURE                Location/Qualifiers
source                 1..553
                       mol_type = protein
                       organism = synthetic construct
                       note = NDV-F of genotype V (vHVT308)
SEQUENCE: 22
MGSKPSTWIS VTLMLITRTM LILSCICPTS SLDGRPLAAA GIVVTGDKAV NIYTSSQTGS  60
IIIKLLPNMP KDKEACAKAP LEAYNRTLTT LLTPLGDSIR RIQGSATTSG GGKQGRLVGA  120
IIGSVALGVA TAAQITAAAA LIQANQNAAN ILRLKESIAA TNDAVHEVTN GLSQLAVAVG  180
KMQQFVNNQF NNTARELDCI KIAQQVGVEL NLYLTELTTV FGPQITSPAL TQLTIQALYN  240
LAGGNMDYLL TKLGVGNNQL SSLIGSGLIT GNPILYDSQT QLLGIQINLP SVGSLNNMRA  300
TYLETLSVST TKGFASALVP KVVTQVGSVI EELDTSYCIE SDIDLYCTRV VTFPMSPGIY  360
SCLSGNTSAC MYSKTEGALT TPYMALKGSV IANCKMTTCR CADPPGIISQ NYGEAVSLID  420
KHSCSVLSLD GITLRLSGEF DATYQKNISI LDSQVIVTGN LDISTELGNV NNSISSTLDK  480
LAESNNKLNK VNVNLTSTSA LITYIVLAIV SLAFGVISLV LACYLMYKQR AQQKTLLWLG  540
NNTLDQMRAT TRT                                                     553
```

-continued

```
SEQ ID NO: 23           moltype = DNA  length = 476
FEATURE                 Location/Qualifiers
source                  1..476
                        mol_type = other DNA
                        organism = synthetic construct
                        note = HHV3gB promoter (reverse direction)
SEQUENCE: 23
cccgggttat atcttctgat tgtgtgggct ctacttgtaa actctcaaaa aacgagcttg  60
gagagaccga cacaaccgcc gtaacaaaca aagaaaatat gcataaaaag cataaccaca  120
cccccgtaac ggatgttatg aaaacgccgg gtccgttgaa tccggagcca gccgctgcat  180
tagggtgtat agaagagaaa aaacgtctga atcgtagatt acgacggtat tctggtcgat  240
ccctgtttct ccactttgaa taatagccac aaggggacat gtttcttcgt acgttaaata  300
aatgccgtct aagggtccgt gggaactgcc tataccttta ggttgagacg tgcacccgcg  360
tggatcctta cctagacggt caacgcgaca taaccgcacc tccccacaat ggaaaacaga  420
ggtgaatagt gtggttgcaa acacaagctc cctaatatat ttccaggcaa gtctct      476

SEQ ID NO: 24           moltype = DNA  length = 476
FEATURE                 Location/Qualifiers
source                  1..476
                        mol_type = other DNA
                        organism = synthetic construct
                        note = HHV3gB promoter
SEQUENCE: 24
agagacttgc ctggaaatat attagggagc ttgtgtttgc aaccacacta ttcacctctg  60
ttttccattg tggggaggtg cggttatgtc gcgttgaccg tctaggtaag gatccacgcg  120
ggtgcacgtc tcaacctaaa ggtataggca gttcccacgg acccttagac ggcatttatt  180
taacgtacga agaaacatgt ccccttgtgg ctattattca aagtggagaa acagggatcg  240
accagaatac cgtcgtaatc tacgattcag acgtttttc tcttctatac accctaatgc  300
agcggctggc tccggattca acggacccgg cgttttcata acatccgtta cgggggtgtg  360
gttatgcttt ttatgcatat tttctttgtt tgttacggcg gttgtgtcgg tctctccaag  420
ctcgtttttt gagagtttac aagtagagcc cacacaatca gaagatataa cccggg      476

SEQ ID NO: 25           moltype = DNA  length = 4347
FEATURE                 Location/Qualifiers
source                  1..4347
                        mol_type = other DNA
                        organism = synthetic construct
                        note = Plasmid pHVTIG1gDCaFopt for vHVT308
misc_feature            1..199
                        note = SV40 Poly A in reverse direction
misc_feature            318..1622
                        note = ILTgD  in reverse direction
misc_feature            1635..2110
                        note = HHV3gB promoter  in reverse direction
misc_feature            2129..2496
                        note = SV40 promoter
misc_feature            2515..4179
                        note = NDV-F-CA02
misc_feature            4194..4347
                        note = Syn Poly A
SEQUENCE: 25
aaaaaacctc ccacacctcc ccctgaacct gaaacataaa atgaatgcaa ttgttgttgt  60
taacttgttt attgcagctt ataatggtta caaataaagc aatagcatca caaatttcac  120
aaataaagca tttttttcac tgcattctag ttgtggtttg tccaaactca tcaatgtatc  180
ttatcatgtc tggatccccg cggcctatgc gcttttcgaa cgtcccaatg aataggcatt  240
ggtatgctat tccatgtgat ttatattatg agcgtgaggc gtggcatgta ggaagaaacc  300
acctattcta ggctcgatta gctacgcgcg cattttacga tgctccaaac cagtagcccc  360
acgagcgcga ccgcgcaggc tacgaacgcc gcgaatatgg gcatggagac ggcattagaa  420
cttttagtag tctcctccac cgggatcacg gcgggcatgt cattgtaata gtcaggatcc  480
gagtttggat catcgtgctc ggtgtcctcg gggacttcgt cgtcttcggg gagggcggca  540
ggattttctc cagaagcctc tgcctgcatg tcgtcctccg agtcttctgg aggggccttc  600
ttttcgctgc tttctgcgtc cggggtgcgc ccttccgctt tcttggttac agcgggaatt  660
tcttgcggga cgctatctgg acgagggtct ggcgcgctag gattcttttt cctcagcaaa  720
ttattccagc gctgcagaat atcttcgtat ccccgatata cgtcgtccgc gtgtcgtgta  780
ttggtgtctg cgatcggata aaggtgttcg ccttgaaatc cagtctgata ctgttctgtt  840
gtccagcatt tcgacggtaa aaagttaagc tgcgacccga tctttaaaca gcgatcgtta  900
acttctagag ttacgagagc tgtttgcgca aatctcccga ttttcagggt cagcaagtat  960
tggccagaga gcgcagcagt gggggagaat atagtcagtc ccgcgccatt tcgcgataca  1020
agggtgctag gaacatagtc cactgcccac atctgtgcag attgaacggc gcattcagat  1080
agcagttgta cgtcgccaca ttccctgtac tcttttctat agattggaca gtacttgtcc  1140
tcgccgtcgt cgcccttaat cacgtagaac cagacgacgg aggcctcgaa agggcccccc  1200
ttctcttttt ctttggccgc cgatatcatg tcgtccacgt tagaaatcgg gttgagctcg  1260
acaacgtcgc agcctcttga taccctagtg aggtatctgt tatacgggcc aaccgccggt  1320
atggttagcg cgtcgagcgc gcgacggcct aaaatgtagt cgtacgtgac ggcggcggtg  1380
ctctggctag cgaaggaaga aagcagtacg atagtccaaa aagcattcct caaaaataaa  1440
tggcggtcca tagcgttgcg tacaaagcag atatgctccc gcataatcct gacacaagtc  1500
cagaaaagag tgaatacagc tgcgcctgag cagcaccgtt ttccaccgca atccatgtgt  1560
ttgttaagca cctctccttt cgcgtagtaa cgcgagtgcc gtctgagatg aggacggtgc  1620
```

-continued

```
atggtggcgg ccgccccggg ttatatcttc tgattgtgtg ggctctactt gtaaactctc  1680
aaaaaacgag cttggagaga ccgacacaac cgccgtaaca aacaaagaaa atatgcataa  1740
aaagcataac cacacccccg taacggatgt tatgaaaacg ccgggtccgt tgaatccgga  1800
gccagccgct gcattagggt gtatagaaga gaaaaaacgt ctgaatcgta gattacgacg  1860
gtattctggt cgatccctgt ttctccactt tgaataatag ccacaagggg acatgtttct  1920
tcgtacgtta aataaatgcc gtctaagggt ccgtgggaac tgcctatacc tttaggttga  1980
gacgtgcacc cgcgtggatc cttacctaga cggtcaacgc gacataaccg cacctcccca  2040
caatggaaaa cagaggtgaa tagtgtggtt gcaaacacaa gctccctaat atatttccag  2100
gcaagtctct gaattaattc cctcgaccca attcgagctc ggtacagctt ggctgtggaa  2160
tgtgtgtcag ttagggtgtg gaaagtcccc aggctcccca gcaggcagaa gtatgcaaag  2220
catgcatctc aattagtcag caaccaggtg tggaaagtcc ccaggctccc cagcaggcag  2280
aagtatgcaa agcatgcatc tcaattagtc agcaaccata gtcccgcccc taactccgcc  2340
catcccgccc ctaactccgc ccagttccgc ccattctccg ccccatggct gactaatttt  2400
ttttatttat gcagaggccg aggccgcctc ggcctctgag ctattccaga agtagtgagg  2460
aggctttttt ggaggcctag gcttttgcaa aaagctcccg ggcggccgc caccatgggc  2520
agcaagccca gcacctggat cagcgtgacc ctgatgctga tcaccagaac catgctgatc  2580
ctgagctgca tctgccccac aagcagcctg gacggcagac ccctggccgc tgccggcatc  2640
gtggtgaccg gcgacaaggc cgtgaacatc tacaccagca gccagaccgg cagcatcatc  2700
atcaagctgc tgcccaacat gcccaaggac aaagaggcct gcgccaaggc ccccctggaa  2760
gcctacaaca gaaccctgac caccctgctg acccccctgg gcgacagcat cagaagaatc  2820
cagggcagcg ccaccacaag cggcggagga aagcagggca gactggtggg cgctatcatc  2880
gggagcgtgg ccctgggcgt ggccacagct gcccagatta ccgctgcagc cgccctgatt  2940
caggccaatc agaacgccgc caacatcctg agactgaaag agagcattgc cgccaccaac  3000
gacgccgtgc acgaagtgac aaacggactg tcccagctgg ctgtcgctgt cggcaagatg  3060
cagcagttcg tgaacaacca gttcaacaac accgccagag agctggactg catcaagatc  3120
gcccagcagg tgggcgtgga gctgaacctg tacctgaccg agctgaccac agtgttcggc  3180
ccccagatca caagccccgc tctgacccag ctgacaatcc aggccctgta caacctggct  3240
ggcggcaaca tggactatct gctgactaag ctgggagtgg gcaacaacca gctgtccagc  3300
ctgatcgggt ccgggctgat cacaggcaac cccatcctgt acgacagcca gacacagctg  3360
ctgggcatcc agatcaacct gccatccgtg ggaagcctga acaacatgag agccacctac  3420
ctggaaaccc tgagcgtgtc caccaccaag ggcttcgcca gcgccctggt gcccaaggtg  3480
gtgacacagg tgggcagcgt gatcgaggaa ctggacacca gctactgcat cgagagcgac  3540
atcgacctgt actgcaccag agtggtgacc ttcccaatga gccccggcat ctacagctgc  3600
ctgagcggca acaccagcgc ctgcatgtac agcaagaccg aaggagcact gacaacaccc  3660
tacatggccc tgaagggaag cgtgatcgcc aactgcaaga tgaccacctg cagatgcgcc  3720
gacccccccag gcatcatcag ccagaactac ggcgaggccg tgagcctgat cgacaaacat  3780
tcctgtagcg tgctgtccct ggatggcatc acactgagac tgagcggcga gttcgacgcc  3840
acctaccaga agaacatcag catcctggac agccaggtga tcgtgaccgg caacctggac  3900
atcagcaccg agctgggcaa cgtgaacaac agcatcagca gcaccctgga caagctggcc  3960
gagtccaaca acaagctgaa caaagtgaac gtgaacctga ccagcacaag cgccctgatc  4020
acctacatcg tgctggccat cgtgtccctg gccttcggcg tgatcagcct ggtgctggcc  4080
tgctacctga tgtacaagca gagagcccag cagaaaaccc tgctgtggct gggcaataac  4140
accctggacc agatgagggc caccaccaga acctgatgag cggccgcgat atcaataaaa  4200
tatctttatt ttcattacat ctgtgtgttg gttttttgtg tgaatcgata gtactaacat  4260
acgctctcca tcaaaacaaa acgaaacaaa acaaactagc aaaataggct gtccccagtg  4320
caagtgcagg tgccagaaca tttctct                                       4347

SEQ ID NO: 26           moltype = DNA  length = 5149
FEATURE                 Location/Qualifiers
source                  1..5149
                        mol_type = other DNA
                        organism = synthetic construct
                        note = Plasmid pFwtIRESgD for vHVT322
misc_feature            1..1391
                        note = mCMV promoter
misc_feature            1400..3061
                        note = NDV-Fwt VIId
misc_feature            3072..3634
                        note = IRES
misc_feature            3638..4942
                        note = ILTgD
misc_feature            4951..5149
                        note = SV40 Poly A
SEQUENCE: 26
aactccgccc gttttatgac tagaaccaat agtttttaat gccaaatgca ctgaaatccc  60
ctaatttgca aagccaaacg cccccctatgt gagtaatacg ggacttttt acccaatttc  120
ccacgcggaa agccccctaa tacactcata tggcatatga atcagcacgg tcatgcactc  180
taatggcggc ccatagggac tttccacata gggggcgttc accatttccc agcataggg  240
tggtgactca atggccttta cccaagtaca ttgggtcaat gggaggtaag ccaatgggtt  300
tttcccatta ctggcaagca cactgagtca aatgggactt tccactgggt tttgcccaag  360
tacattgggt caatgggagg tgagccaatg ggaaaaaccc attgctgcca agtacactga  420
ctcaataggg actttccaat gggtttttcc attgttggca agcatataag gtcaatgtgg  480
gtgagtcaat agggactttc cattgtattc tgcccagtac ataaggtcaa tagggggtga  540
atcaacagga aagtcccatt ggagccaagt acactgcgtc aatagggact ttccattggg  600
ttttgcccag tacataaggt caatagggga tgagtcaatg ggaaaaaccc attggagcca  660
agtacactga ctcaataggg actttccatt gggttttgcc cagtacataa ggtcaatagg  720
gggtgagtca acaggaaagt tccattggag ccaagtacat tgagtcaata gggactttcc  780
aatgggtttt gcccagtaca taaggtcaat gggaggtaag ccaatgggtt tttcccatta  840
ctggcacgta tactgagtca ttagggactt tccaatgggt tttgcccagt acataaggtc  900
```

-continued

```
aataggggtg aatcaacagg aaagtcccat tggagccaag tacactgagt caatagggac  960
tttccattgg gttttgccca gtacaaaagg tcaatagggg gtgagtcaat gggtttttcc  1020
cattattggc acgtacataa ggtcaatagg ggtgagtcat tgggtttttc cagccaattt  1080
aattaaaacg ccatgtactt tcccaccatt gacgtcaatg ggctattgaa actaatgcaa  1140
cgtgaccttt aaacggtact ttcccatagc tgattaatgg gaaagtaccg ttctcgagcc  1200
aatacacgtc aatgggaagt gaaagggcag ccaaaacgta acaccgcccc ggttttcccc  1260
tggaaattcc atattggcac gcattctatt ggctgagctg cgttctacgt gggtataaga  1320
ggcgcgacca gcgtcggtac cgtcgcagtc ttcggtctga ccaccgtaga acgcagagct  1380
cctcgctgca ggcggccgca tgggctccaa accttctacc aggatcccag cacctctgat  1440
gctgatcacc cggattatgc tgatattggg ctgtatccgt ccgacaagct ctcttgacgg  1500
caggcctctt gcagctgcag gaattgtagt aacaggagat aaggcagtca atgtatacac  1560
ttcgtctcag acagggtcaa tcatagtcaa gttgctcccg aatatgccca gggataagga  1620
ggcgtgtgca aaagccccat tagaggcata taacagaaca ctgactactt tgctcactcc  1680
tcttggcgac tccatccgca agatccaagg gtctgtgtcc acatctggag gaggcaagca  1740
aggccgcctg ataggtgctg ttattggcag tgtagctctt ggggttgcaa cagcggcaca  1800
gataacagca gctgcggccc taatacaagc caaccagaat gccgccaaca tcctccggct  1860
taaggagagc attgctgcaa ccaatgaagc tgtgcatgaa gtcaccgacg gattatcaca  1920
actatcagtg gcagttggga agatgcagca gtttgtcaat gaccagttta ataatacggc  1980
gcgagaattg gactgtataa aaatcacaca acaggttggt gtagaactca acctatacct  2040
aactgaattg actacagtat tcgggccaca gatcacctcc cctgcattaa ctcagctgac  2100
catccaggca ctttataatt tagctggtgg caatatggat tacttattaa ctaagttagg  2160
tatagggaac aatcaactca gctcgttaat tggtagcggc ctgatcactg gttaccctat  2220
actgtatgac tcacagactc aactcttggg catacaagtg aatttaccct cagtcgggaa  2280
cttaaataat atgcgtgcca cctatttgga gaccttatct gtaagtacaa ccaaaggata  2340
tgcctcagca cttgtcccga aagtagtgac acaagtcggt tccgtgatag aagagcttga  2400
cacctcatac tgtatagagt ccgatctgga tttatattgt actagaatag tgacattccc  2460
catgtcccca ggtatttatt cctgtttgag cggcaacaca tcagcttgca tgtattcaaa  2520
gactgaaggc gcactcacta cgccgtatat ggcccttaaa ggctcagtta ttgccaattg  2580
taaaataaca acatgtagat gtacagaccc tcctggtatc atatcgcaaa attatggaga  2640
agctgtatcc ctgatagata gacattcgtg caatgtctta tcattagacg ggataactct  2700
aaggctcagt ggggaatttg atgcaactta tcaaaagaac atctcaatac tagattctca  2760
agtcatcgtg acaggcaatc ttgatatatc aactgaactt ggaaacgtca acaattcaat  2820
cagcaatgcc ttggataggt tggcagaaag caacagcaag ctagaaaaag tcaatgtcag  2880
actaaccagc acatctgctc tcattaccta tattgttcta actgtcattt ctctagtttt  2940
cggtgcactt agtctggtgt tagcgtgtta cctgatgtac aaacagaagg cacaacaaaa  3000
gaccttgcta tggcttggga ataataccct cgatcagatg agagccacta caagagcatg  3060
agcggccgcc cccccccccc ctaacgttac tggccgaagc cgcttggaat aaggccggtg  3120
tgcgtttgtc tatatgttat tttccaccat attgccgtct tttggcaatg tgagggcccg  3180
gaaacctggc cctgtcttct tgacgagcat tcctaggggt ctttcccctc tcgccaaagg  3240
aatgcaaggt ctgttgaatg tcgtgaagga agcagttcct ctggaagctt cttgaagaca  3300
aacaacgtct gtagcgaccc tttgcaggca gcggaacccc ccacctggcg acaggtgcct  3360
ctgcggccaa aagccacgtg tataagatac acctgcaaag gcggcacaac cccagtgcca  3420
cgttgtgagt tggatagttg tggaaagagt caaatggctc tcctcaagcg tattcaacaa  3480
ggggctgaag gatgcccaga aggtacccca ttgtatggga tctgatctgg ggcctcggtg  3540
cacatgcttt acatgtgttt agtcgaggtt aaaaaacgtc taggcccccc gaaccacggg  3600
gacgtggttt tcctttgaaa aacacgatga taataccatg caccgtcctc atctcagacg  3660
gcactcgcgt tactacgcga aaggagaggt gcttaacaaa cacatggatt gcggtggaaa  3720
acggtgctgc tcaggcgcag ctgtattcac tcttttctgg acttgtgtca ggattatgcg  3780
ggagcatatc tgctttgtac gcaacgctat ggaccgccat ttatttttga ggaatgcttt  3840
ttggactatc gtactgcttt cttccttcgc tagccagagc accgccgccg tcacgtacga  3900
ctacatttta ggccgtcgcg cgctcgacgc gctaaccata ccggcggttg gcccgtataa  3960
cagatacctc actagggtat caagaggctg cgacgttgtc gagctcaacc cgatttctaa  4020
cgtggacgac atgatatcgg cggccaaaga aaaagagaag gggggccctt tcgaggcctc  4080
cgtcgtctgg ttctacgtga ttaagggcga cgacggcgag gacaagtact gtccaatcta  4140
tagaaaagag tacagggaat gtggcgacgt acaactgcta tctgaatgcg ccgttcaatc  4200
tgcacagatg tgggcagtgg actatgttcc tagcaccctt gtatcgcgaa atggcgcggg  4260
actgactata ttctccccca ctgctgcgct ctctggccaa tacttgctga ccctgaaaat  4320
cgggagattt gcgcaaacag ctctcgtaac tctagaagtt aacgatcgct gtttaaagat  4380
cgggtcgcag cttaactttt taccgtcgaa atgctggaca acagaacagt atcagactgg  4440
atttcaaggc gaacaccttt atccgatcgc agacaccaat acacgacacg cggacgacgt  4500
atatcgggga tacgaagata ttctgcagcg ctggaataat ttgctgagga aaaagaatcc  4560
tagcgcgcca gaccctcgtc cagatagcgt cccgcaagaa attcccgctg taaccaagaa  4620
agcggaaggg cgcaccccgg acgcagaaag cagcgaaaag aaggcccctc cagaagactc  4680
ggaggacgac atgcaggcag aggcttctgg agaaaatcct gccgccctcc ccgaagacga  4740
cgaagtcccc gaggacaccg agcacgatga tccaaactcg gatcctgact attacaatga  4800
catgcccgcc gtgatcccgg tggaggagac tactaaaagt tctaatgccg tctccatgcc  4860
catattcgcg gcgttcgtag cctgcgcggt cgcgctcgtg gggctactgg tttggagcat  4920
cgtaaaatgc gcgcgtagct aagcggccgc ggggatccag acatgataag atacattgat  4980
gagtttggac aaaccacaac tagaatgcag tgaaaaaaat gctttatttg tgaaatttgt  5040
gatgctattg ctttatttgt aaccattata agctgcaata aacaagttaa caacaacaat  5100
tgcattcatt ttatgtttca ggttcagggg gaggtgtggg aggtttttt             5149
```

```
SEQ ID NO: 27           moltype = DNA  length = 1857
FEATURE                 Location/Qualifiers
source                  1..1857
                        mol_type = other DNA
                        organism = synthetic construct
                        note = plasmid pHVTUS2SvgDwtsyn for vHVT406
misc_feature            1..362
```

-continued

```
                        note = SV40 promoter
misc_feature            379..1683
                        note = ILTV gD
misc_feature            1695..1857
                        note = Syn Poly A
SEQUENCE: 27
gagctcggta cagcttggct gtggaatgtg tgtcagttag ggtgtggaaa gtccccaggc  60
tccccagcag gcagaagtat gcaaagcatg catctcaatt agtcagcaac caggtgtgga  120
aagtccccag gctccccagc aggcagaagt atgcaaagca tgcatctcaa ttagtcagca  180
accatagtcc cgcccctaac tccgcccatc ccgcccctaa ctccgcccag ttccgcccat  240
tctccgcccc atggctgact aattttttt atttatgcag aggccgaggc cgcctcggcc  300
tctgagctat tccagaagta gtgaggaggc ttttttggag gcctaggctt ttgcaaaaag  360
ctgcggccgg ccgccaccat gcaccgtcct catctcagac ggcactcgcg ttactacgcg  420
aaaggagagg tgcttaacaa acacatggat tgcggtggaa aacggtgctg ctcaggcgca  480
gctgtattca ctcttttctg gacttgtgtc aggattatgc gggagcatat ctgctttgta  540
cgcaacgcta tggaccgcca tttatttttg aggaatgctt tttggactat cgtactgctt  600
tcttccttcg ctagccagag caccgccgcc gtcacgtacg actacatttt aggccgtcgc  660
gcgctcgacg cgctaaccat accggcggtt ggcccgtata acagatacct cactagggta  720
tcaagaggct gcgacgttgt cgagctcaac ccgatttcta acgtggacga catgatatcg  780
gcggccaaag aaaaagagaa ggggggccct ttcgaggcct ccgtcgtctg gttctacgtg  840
attaagggcg acgacggcga ggacaagtac tgtccaatct atagaaaaga gtacagggaa  900
tgtggcgacg tacaactgct atctgaatgc gccgttcaat ctgcacagat gtgggcagtg  960
gactatgttc ctagcaccct tgtatcgcga aatggcgcgg gactgactat attctccccc  1020
actgctgcgc tctctggcca atacttgctg accctgaaaa tcgggagatt tgcgcaaaca  1080
gctctcgtaa ctctagaagt taacgatcgc tgtttaaaga tcgggtcgca gcttaacttt  1140
ttaccgtcga aatgctggac aacagaacag tatcagactg gatttcaagg cgaacacctt  1200
tatccgatcg cagacaccaa tacacgacac gcggacgacg tatatcgggg atacgaagat  1260
attctgcagc gctggaataa tttgctgagg aaaaagaatc ctagcgcgcc agaccctcgt  1320
ccagatagcg tcccgcaaga aattcccgct gtaaccaaga aagcggaagg gcgcaccccg  1380
gacgcagaaa gcagcgaaaa gaaggcccct ccagaagact cggaggacga catgcaggca  1440
gaggcttctg gagaaaatcc tgccgccctc cccgaagacg acgaagtccc cgaggacacc  1500
gagcacgatg atccaaactc ggatcctgac tattacaatg acatgcccgc cgtgatcccg  1560
gtggaggaga ctactaaaag ttctaatgcc gtctccatgc ccatattcgc ggcgttcgta  1620
gcctgcgcgg tcgcgctcgt ggggctactg gtttggagca tcgtaaaatg cgcgcgtagc  1680
taatcgagcc tagaggcaat aaaatatctt tattttcatt acatctgtgt gttggttttt  1740
tgtgtgaatc gatagtacta acatacgctc tccatcaaaa caaaacgaaa caaaacaaac  1800
tagcaaaata ggctgtcccc agtgcaagtg caggtgccag aacatttctc tctcgag     1857
```